US008613930B2

(12) United States Patent
Chari et al.

(10) Patent No.: US 8,613,930 B2
(45) Date of Patent: Dec. 24, 2013

(54) CROSS-LINKERS AND THEIR USES

(75) Inventors: Ravi V. J. Chari, Newton, MA (US);
Robert Yongxin Zhao, Lexington, MA (US); Yelena Kovtun, Stow, MA (US);
Rajeeva Singh, Framingham, MA (US);
Wayne Charles Widdison, Belmont, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 13/542,126

(22) Filed: Jul. 5, 2012

(65) Prior Publication Data

US 2013/0011419 A1  Jan. 10, 2013

Related U.S. Application Data

(62) Division of application No. 12/433,604, filed on Apr. 30, 2009, now Pat. No. 8,236,319.

(60) Provisional application No. 61/049,291, filed on Apr. 30, 2008, provisional application No. 61/147,966, filed on Jan. 28, 2009.

(51) Int. Cl.
*A61K 39/00* (2006.01)
*A61K 36/04* (2006.01)
*C07K 16/06* (2006.01)

(52) U.S. Cl.
USPC ............... 424/181.1; 530/331; 530/391.9; 530/330

(58) Field of Classification Search
USPC ............... 424/181.1; 530/330, 331, 391.9
See application file for complete search history.

(56) References Cited

U.S. PATENT DOCUMENTS

| 5,219,564 | A | | 6/1993 | Zalipsky et al. |
| 5,738,846 | A | | 4/1998 | Greenwald et al. |
| 6,153,655 | A | * | 11/2000 | Martinez et al. ............ 514/772.3 |
| 6,251,382 | B1 | | 6/2001 | Greenwald et al. |
| 6,395,266 | B1 | * | 5/2002 | Martinez et al. ............ 424/78.3 |
| 2004/0001838 | A1 | | 1/2004 | Zhao et al. |
| 2004/0192900 | A1 | | 9/2004 | Kunz et al. |
| 2005/0158370 | A1 | | 7/2005 | Flinn et al. |
| 2006/0127407 | A1 | | 6/2006 | Chen et al. |
| 2006/0233814 | A1 | | 10/2006 | Goldmakher et al. |
| 2007/0092940 | A1 | | 4/2007 | Eigenbrot et al. |

FOREIGN PATENT DOCUMENTS

| EP | 0457250 A2 | 11/1991 |
| EP | 1514561 A1 | 3/2005 |
| GB | 2029825 A | 3/1980 |
| WO | 98/13059 A1 | 4/1998 |
| WO | 2005/009369 A2 | 2/2005 |

OTHER PUBLICATIONS

Dubowchik et al. Pharmacology & Therapeutics, 1999, 83, 67-123.*
Ravi V.J. Chari et al., "Targeted delivery of chemotherapeutics: tumor-activated prodrug therapy", Advanced Drug Delivery Reviews, 1998, 31: 89-104.
Gene M. Dubowchik et al., "Receptor-mediated and enzyme-dependent targeting of cytotoxic anticancer drugs", Pharmacology and Therapeutics, 1999, 83: 67-123.
Examination Report dated Apr. 13, 2011, issued in New Zealand Patent Application No. 588884 (in the name of Immunogen, Inc.
Martin C. Garnett, "Targeted drug conjugates: principles and progress", Advanced Drug Delivery Reviews, 2001, 53: 171-216.
Sajid Malik et al., "Preparation of (RS)-5-Amino-3-Carboxypentanoic Acid (1)", Synthetic Communications, 1993, 23(8): 1047-1051.
Barbara M. Mueller et al., "Antibody Conjugates with Morpholinodoxorubicin and Acid-Cleavable Linkers", Bioconjugate Chem., 1990, 1: 325-330.
Wayne C. Widdison et al., "Semisynthetic Maytansine Analogues for the Targeted Treatment of Cancer", J. Med. Chem., 2006, 49: 4392-4408.
Extended European Search Report issued in corresponding EP Application No. 09739779.8 on Aug. 20, 2012.
Guillaume Clavé et al., "A novel heterotrifunctional peptide-based cross-linking reagent for facile access to bioconjugates. Applications to peptide fluorescent labelling and immobilisation", Organic & Biomolecular Chemistry, 2008, 6: 3065-3078.
Olivier Ploux et al., "A New Modified Amino Acid: 2-Amino-3-mercapto-3-phenylpropionic Acid (3-Mercaptophenylalanine). Synthesis of Derivatives, Separation of Stereoisomers, and Assignment of Absolute Configuration", J. Org. Chem., 1988, 53: 3154-3158.
Gerhard Sengle et al., "Synthesis, Incorporation Efficiency, and Stability of Disulfide Bridged Functional Groups at RNA 5'-Ends", Bioorganic & Medicinal Chemistry, 2000, 8: 1317-1329.
Yashveer Singh et al., "A novel heterobifunctional linker for facile access to bioconjugates", Organic & Biomolecular Chemistry, 2006, 4: 1413-1419.
Jane J. Zara et al., "A Carbohydrate-Directed Heterobifunctional Cross-Linking Reagent for the Synthesis of Immunoconjugates", Analytical Biochemistry, 1991, 194: 156-162.
Office Action issued in corresponding Russian Application No. 2010148743 on Nov. 1, 2011 (in the name of Immunogen, Inc.).

* cited by examiner

*Primary Examiner* — Nizal Chandrakumar
(74) *Attorney, Agent, or Firm* — McCarter & English, LLP; Steven G. Davis; Yu Lu

(57) ABSTRACT

Charged or pro-charged cross-linking moieties and conjugates of cell binding agents and drugs comprising the charged or pro-charged cross-linking moieties and method of making the same.

26 Claims, 48 Drawing Sheets hydrolysis in target cell
(Cleavage between two alpha amino acids)

Hydrolysis in target cell (Cleavage between two alpha amino acids)

Figure 57(A)  Cytotoxicity of anti-CD56(huN901) antibody-maytansinoid conjugates
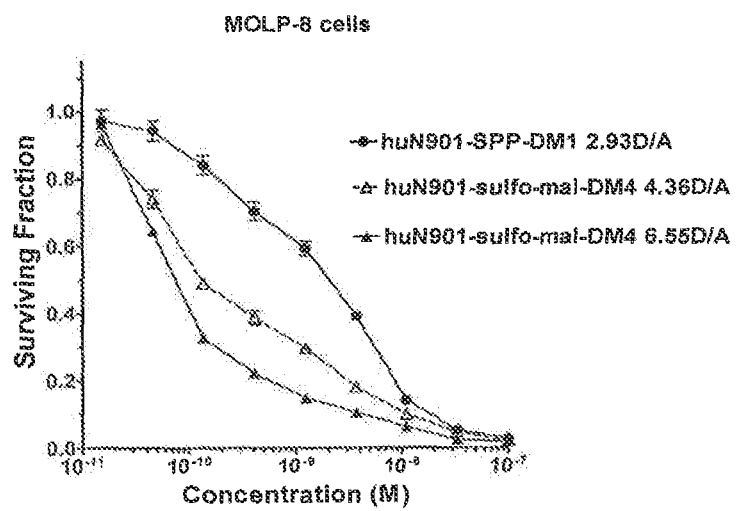
Figure 57(B)  Cytotoxicity of anti-CD56(huN901) antibody-maytansinoid conjugates
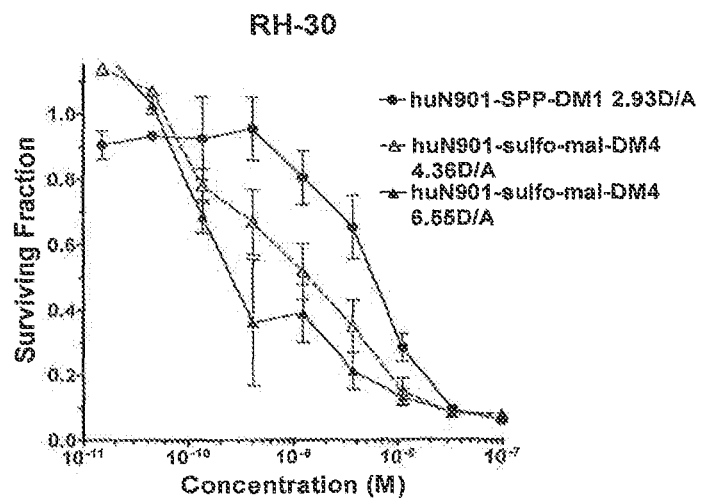

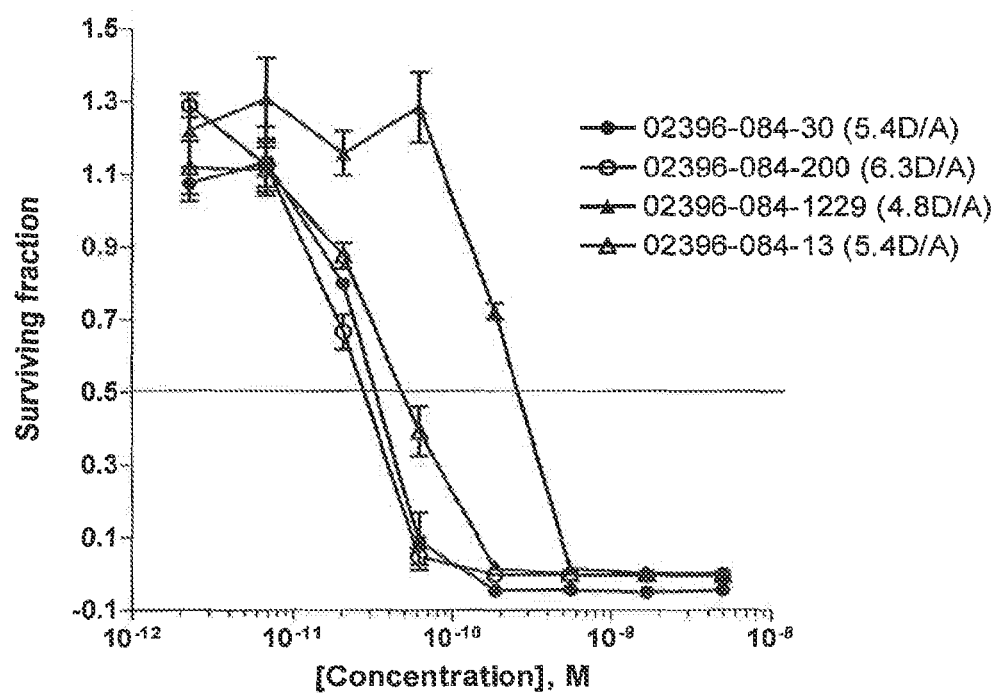
Figure 57(C) Cytotoxicity of anti-CD56(huN901) antibody-maytansinoid conjugates

CROSS-LINKERS AND THEIR USES

CROSS-LINKERS AND THEIR USES

This is a Divisional Application of U.S. patent application Ser. No. 12/433,604, filed Apr. 30, 2009, which claims priority to U.S. Provisional Application No. 61/049,291, filed Apr. 30, 2008 and to U.S. Provisional Application No. 61/147,966, filed Jan. 28, 2009, the contents of all of which are incorporated herein by reference in their entirety.

FIELD OF THE INVENTION

The present invention relates to the synthesis of novel charged cross linkers and cross linkers which can be processed by a target cell to give charged moieties. The present invention also relates to methods of making cell-binding agent-drug conjugates comprising modification of cell-binding agents with these cross-linkers, followed by reaction with drugs, or modification of the drugs with these crosslinkers, followed by reaction with cell-binding agents. The improved method of making conjugates provides the ability to link a higher number of drug molecules per cell-binding agent resulting in greater potency and providing greater aqueous solubility to the conjugates.

BACKGROUND OF THE INVENTION

The bifunctional modification reagent N-succinimidyl 3-(2-pyridyldithio) propionate (SPDP) has been used to link two proteins together through a disulfide bond. The reagent is reacted with the first protein to introduce an active disulfide-containing group in the modification step. A second protein, which contains a free thiol group, is then added to form a disulfide bond between the two proteins in the conjugation step. Many derivatives of SPDP and imide versions of SPDP have been described (U.S. Pat. No. 4,563,304; J. Carlsson et al. 173 *Biochem. J.* 723-737 (1978); Goff D. A., Carroll, S. F. 1 BioConjugate Chem. 381-386 (1990); L. Delprino et al. 82 *J. Pharm. Sci.* 506-512 (1993); S. Arpicco et al., 8 *BioConjugate Chem* 327-337 (1997)).

Conjugates of cell-binding agents with highly cytotoxic drugs have been described (U.S. Pat. Nos. 5,208,020, 5,416,064; 5,475,092, 5,585,499, 6,436,931, 6,372,738 and 6,340,701; R. V. J. Chari et al., 52 *Cancer Res.* 127-131 (1992)). In these conjugates, the cell-binding agents are first modified with a bifunctional agent such as SPDP, SPP or SMCC to introduce an active disulfide or a maleimido moiety. Reaction with a thiol-containing cytotoxic drug provides a conjugate in which the cell-binding agent, such as a monoclonal antibody, and drug are linked via disulfide bonds or thioether bonds.

Heterobifunctional cross-linkers comprising a nitropyridyldithio, dinitropyridyldithio, N,N-dialkylcarboxamidopyridyldithio or di-(N,N-dialkylcarboxamido) pyridyldithio group and a reactive carboxylic ester group such as a N-succinimidyl ester group or a N-sulfosuccinimidyl ester group have been described (U.S. Pat. No. 6,913,748). The presence of a N-sulfosuccinimidyl group was claimed to provide higher aqueous solubility to these cross-linkers. However, once the cell-binding agent has been reacted with these cross-linkers, the N-sulfosuccinimidyl group is displaced and the solubility advantage is lost, both for the modified cell-binding agent and its drug conjugate. Since cytotoxic drugs used in cell-binding agent-drug conjugates are often only sparingly soluble in aqueous solutions, it is often difficult to link a sufficient number of drug molecules to the cell-binding agent and still maintain aqueous solubility. In addition, reactions have to be conducted in dilute solutions, which are cumbersome to scale up because of the need to use large volumes of solution.

SUMMARY OF THE INVENTION

The present invention provides charged linkers, wherein the charges are retained both after modification of the cell-binding agent and in the resulting drug conjugate. More specifically, the present invention relates to the use of charged linkers to link drugs to a cell-binding agent (e.g., an antibody). In one aspect of the invention, the charged linkers are used to modify cell-binding agents and link them to drugs. In another aspect of the invention, the charged linkers are used to modify drugs and link them to cell-binding agents. In yet another aspect of the invention, the charged linkers are used to simultaneously link drugs and the cell-binding agents. In all instances, the preferred end result is a drug-charged linker-cell-binding agent conjugate, which can be represented by the formula, CB-(-L$^c$-D)$_q$, wherein CB is a cell-binding agent, L$^c$ is a charged linker, D is a drug molecule, and q is an integer from 1 to 20. The presence of a charged group(s) in the linker in the cell-binding agent-drug conjugate provides several advantages, such as i) greater water solubility of the final product, ii) ability to operate at a higher concentration in aqueous solutions, iii) ability to link a greater number of drug molecules per molecule of cell-binding agent, resulting in higher potency, iv) potential for the charged conjugate species to be retained inside the target cell, resulting in higher potency, and v) improved sensitivity of multidrug resistant cells, which would be unable to export the charged drug species from the cell. The invention also describes linkers, which can be coupled to a drug and a cell binding agent to give a conjugate which can be metabolized in a cell to produce a drug metabolite containing one or more charged moieties. These linkers will be referred to as pro-charged linkers. Moieties of the linker which will become charged after cell processing will be referred to as pro-charged moieties.

In one aspect of the present invention, the charged or pro-charged cross linker is represented by formula (I) wherein Y' can react with a cell-binding agent and Q can react with a cytotoxic drug:

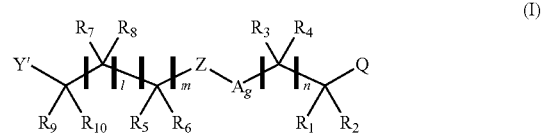

(I)

wherein:

Y' represents a functional group that enables reaction with a cell-binding agent;

Q represents a functional group that enables linkage of a cytotoxic drug via a disulfide, thioether, thioester, peptide, hydrazone, ether, ester, carbamate or amide bond;

$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, $X-SO_3^-$, $OPO_3^{2-}$, $X-OPO_3^{2-}$, $PO_3^{2-}$, $X-PO_3^{2-}$, $CO_2^-$, and cations, such as but not limited to, a nitrogen containing heterocycle, $N^+R_{11}R_{12}R_{13}$ or $X-N^+R_{11}R_{12}R_{13}$, or a phenyl, wherein:

$R_{11}$, $R_{12}$ and $R_{13}$ are the same or different and are H, linear alkyl having from 1 to 6 carbon atoms, or branched or cyclic alkyl having from 3 to 6 carbon atoms and X represents phenyl or a linear alkyl having from 1 to 6 carbon atoms, or a branched or cyclic alkyl having from 3 to 6 carbon atoms;

l, m and n are 0 or an integer from 1 to 4; and

A is a phenyl or a substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$, $X—SO_3^-$, $OPO_3^{2-}$, $X—OPO_3^{2-}$, $PO_3^{2-}$, $X—PO_3^{2-}$, $CO_2^-$, and cations, such as but not limited to, a nitrogen containing heterocycle, $N^+R_{11}R_{12}R_{13}$ or $X—N^+R_{11}R_{12}R_{13}$, wherein X has the same definition as above, and wherein g is 0 or 1;

Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or $NR_{14}$, wherein $R_{14}$ is H, a linear alkyl having from 1-6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent.

In another aspect, the present invention provides a cell-binding agent-drug conjugate of formula (II), in which the cell-binding agent, CB, and the drug, D, have reacted at the two ends of the charged or pro-charged cross linker:

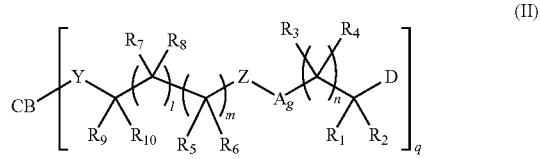

(II)

wherein:

CB represents a cell-binding agent;

D represents the drug linked to the cell-binding agent by a disulfide, thioether, thioester, peptide, hydrazone, ether, ester, carbamate, or amide bond;

$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, $X—SO_3^-$, $OPO_3^{2-}$, $X—OPO_3^{2-}$, $PO_3^{2-}$, $X—PO_3^{2-}$, $CO_2^-$, cations, such as but limited to, a nitrogen containing heterocycle, $N^+R_{11}R_{12}R_{13}$ or $X—N^+R_{11}R_{12}R_{13}$, or a phenyl, wherein:

$R_{11}$, $R_{12}$ and $R_{13}$ are the same or different and are H, linear alkyl having from 1 to 6 carbon atoms, branched or cyclic alkyl having from 3 to 6 carbon atoms and X represents phenyl or a linear alkyl having from 1 to 6 carbon atoms, or a branched or cyclic alkyl having from 3 to 6 carbon atoms;

l, m and n are 0 or an integer from 1 to 4; and

A is a phenyl or substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$, $X—SO_3^-$, $OPO_3^{2-}$, $X—OPO_3^{2-}$, $PO_3^{2-}$, $X—PO_3^{2-}$, $CO_2—$, cations, such as but not limited to, a nitrogen containing heterocycle, $N^+R_{11}R_{12}R_{13}$ or $X—N^+R_{11}R_{12}R_{13}$, wherein X has the same definition as above, and wherein g is 0 or 1;

Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or $NR_{14}$, wherein $R_{14}$ is H, a linear alkyl having from 1-6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent;

Y represents a carbonyl, thioether, amide, disulfide, or hydrazone group; and q represents an integer from 1 to 20.

In a further aspect, the present invention provides a modified cell-binding agent of formula (III), in which the cell-binding agent, CB, has reacted with the cross linker, which still has Q, a group capable of reacting with a cytotoxic drug:

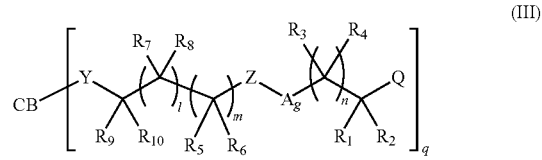

(III)

wherein the substituents are as defined above.

In an even further aspect, the present invention provides a modified drug of formula (IV), in which the drug, D, has reacted with the cross linker, which still has Y', a group capable of reacting with the cell-binding agent:

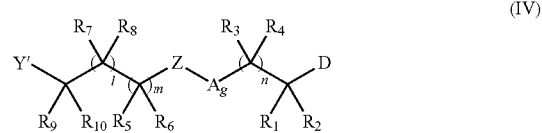

(IV)

wherein the substituents are as defined above.

The present invention further relates to a method of making a cell-binding agent drug conjugate of formula (II), wherein the drug is linked to a cell-binding agent via a charged or pro-charged linker.

The present invention also relates to a method of making a modified cell-binding agent of formula (III), wherein the cell-binding agent is reacted with the charged or pro-charged linker.

The present invention also relates to a method of making a modified drug of formula (IV), wherein the drug is reacted with the charged or pro-charged linker.

The present invention includes a composition (e.g., a pharmaceutical composition) comprising conjugates or derivatives thereof (and/or solvates, hydrates and/or salts thereof) and a carrier (a pharmaceutically acceptable carrier). The present invention also includes a composition (e.g., a pharmaceutical composition) comprising conjugates or derivatives thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human).

The present invention includes a method of inhibiting abnormal cell growth or treating a proliferative disorder in a mammal (e.g., human) comprising administering to said mammal a therapeutically effective amount of the conjugates or derivatives thereof, (and/or solvates and salts thereof) or a composition thereof, alone or in combination with a second therapeutic agent.

The compounds of this invention, derivatives thereof, or conjugates thereof, and compositions comprising them, are useful for treating or lessening the severity of disorders, such as, characterized by abnormal growth of cells (e.g., cancer). Other applications for compounds or conjugates of this invention include, but are not limited to, treating osteoporosis, depression, anxiety, stress, phobias, panic, dysphoria, psychiatric disorders, and pain or as antiepileptics, antibacterials, diuretics and hypotensives, hypolipidemics, and anti-depressants.

BRIEF DESCRIPTION OF THE DRAWINGS

FIG. 57 shows the in vitro potency of cell-binding agent-drug conjugates in which a charged crosslinker is incorporated.

In FIGS. 1-71, where applicable, n represents 0 or an integer from 1 to 10, and m represents 0 or an integer from 1 to 2000.

DETAILED DESCRIPTION OF THE INVENTION

The novel conjugates disclosed herein use charged or pro-charged cross-linkers. Examples of some suitable cross-linkers and their synthesis are shown in FIGS. 1 to 10. Preferably, the charged or pro-charged cross-linkers are those containing sulfonate, phosphate, carboxyl or quaternary amine substituents that significantly increase the solubility of the modified cell-binding agent and the cell-binding agent-drug conjugates, especially for monoclonal antibody-drug conjugates with 2 to 20 drugs/antibody linked. Conjugates prepared from linkers containing a pro-charged moiety would produce one or more charged moieties after the conjugate is metabolized in a cell.

Cross-Linkers

Figure 13:
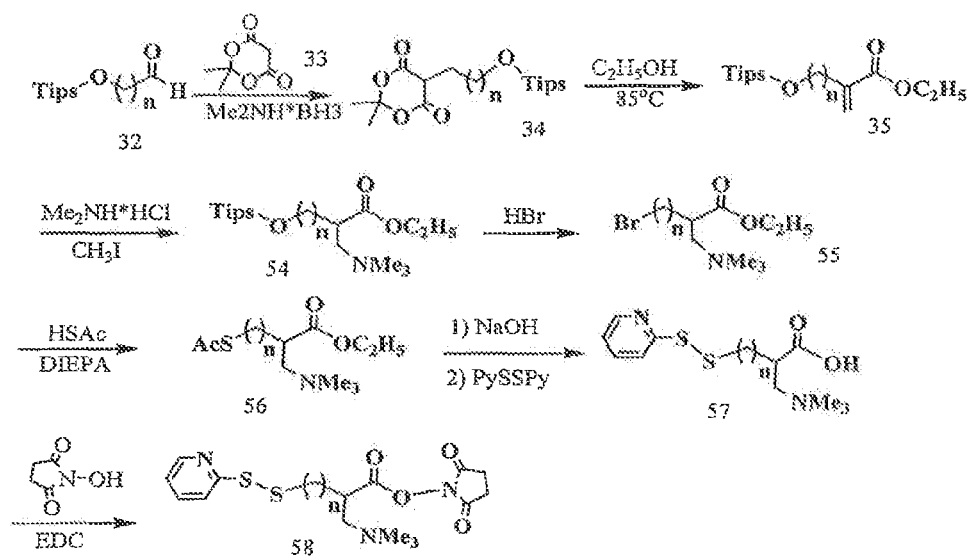
FIG. 13 shows the synthesis of quartenary amine-containing cross-linking reagents that contain a pyridyldisulfide group and a reactive carboxylic acid ester.
Figure 14:
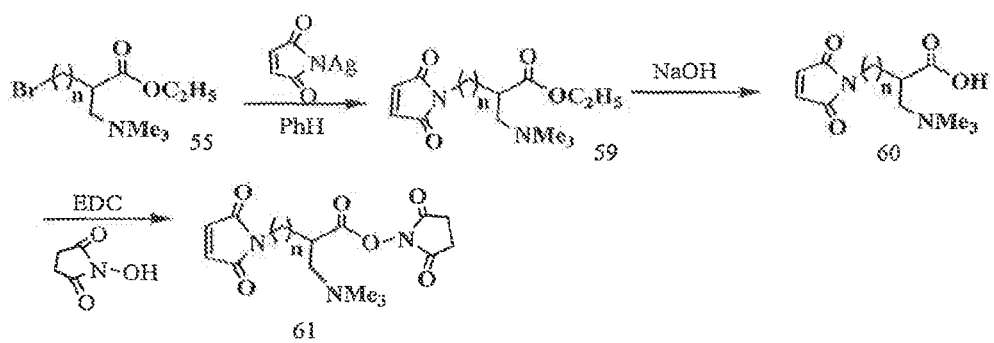
FIG. 14 shows the synthesis of quartenary amine cross-linking agents bearing a reactive carboxylic acid ester and maleimido substituent, enabling linkage via thioether bonds.
Figure 15:
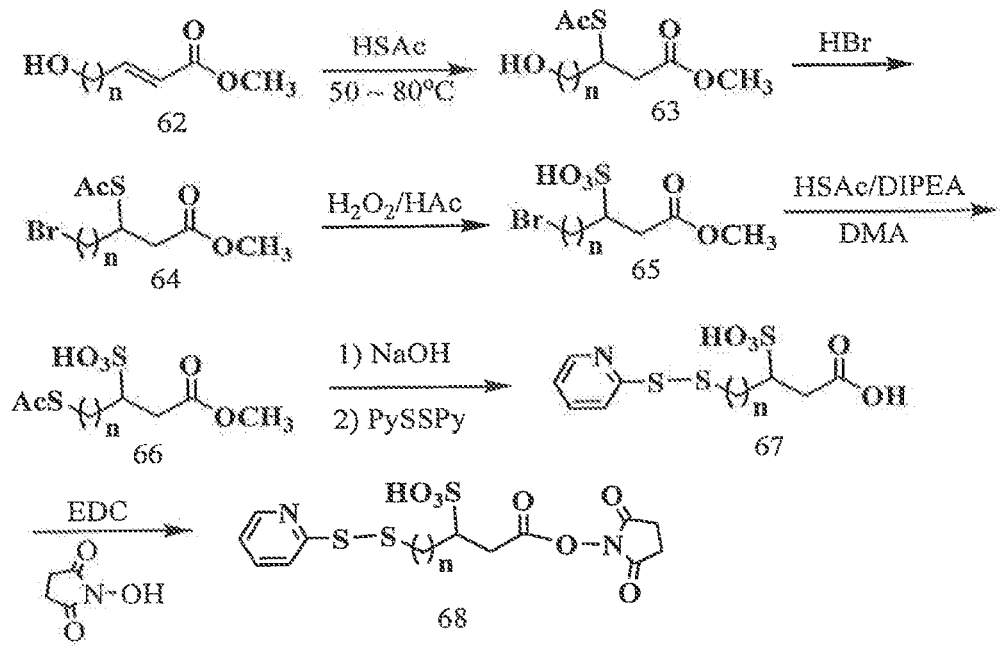
FIG. 15 shows the synthesis of sulfonic acid-containing cross-linking reagents that contain a pyridyldisulfide group and a reactive carboxylic acid ester. In these compounds, the sulfonate substituent is on the carbon atom on the position β to the carboxyl ester.
Figure 16:
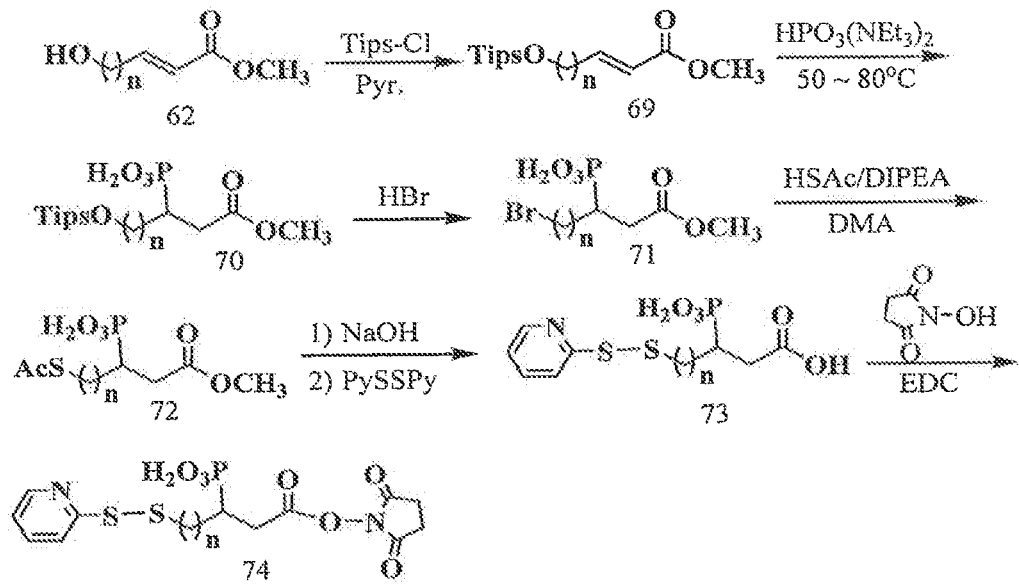
FIG. 16 shows the synthesis of phosphate-containing cross-linking reagents that contain a pyridyldisulfide group and a reactive carboxylic acid ester. In these compounds, the phosphate substituent is on the β-position relative to the carboxyl ester.
Figure 17:
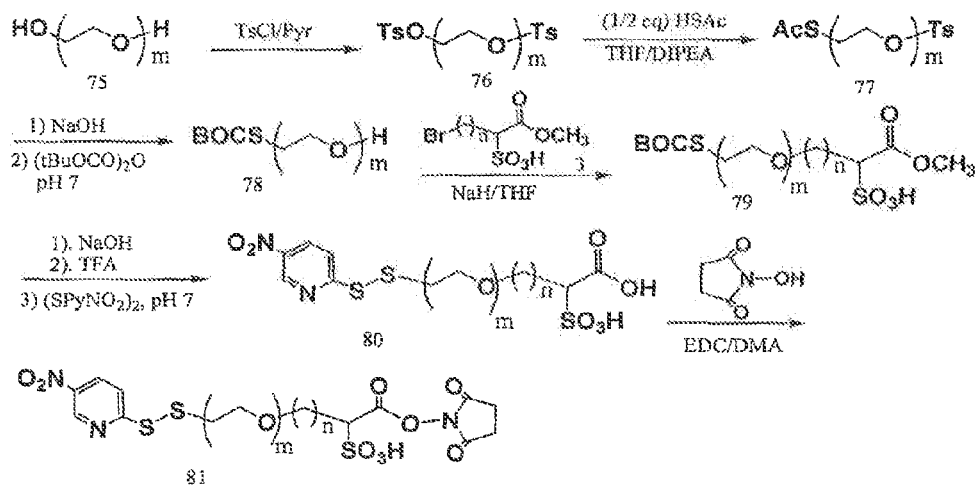
FIGS. 17, 18 and 19 show the synthesis of various sulfonic acid-containing cross-linking reagents that contain a polyethyleneglycol (PEG) chain, along with a nitropyridyldisulfide group and a reactive carboxylic acid ester.
Figure 18:
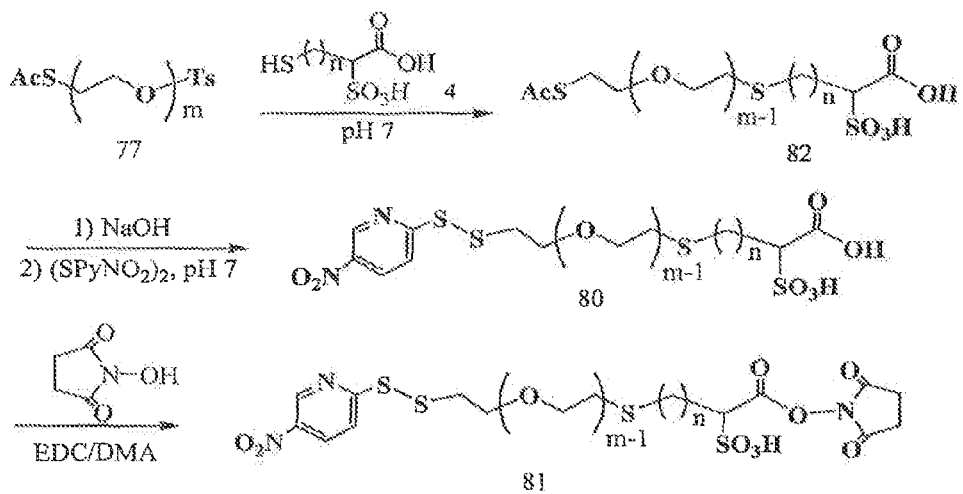
Figure 19:
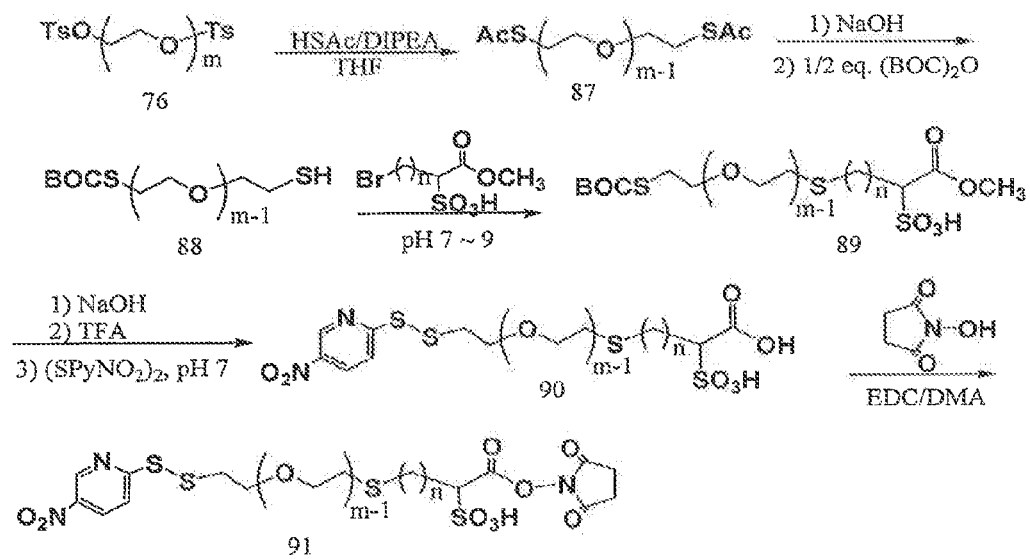
Figure 20:
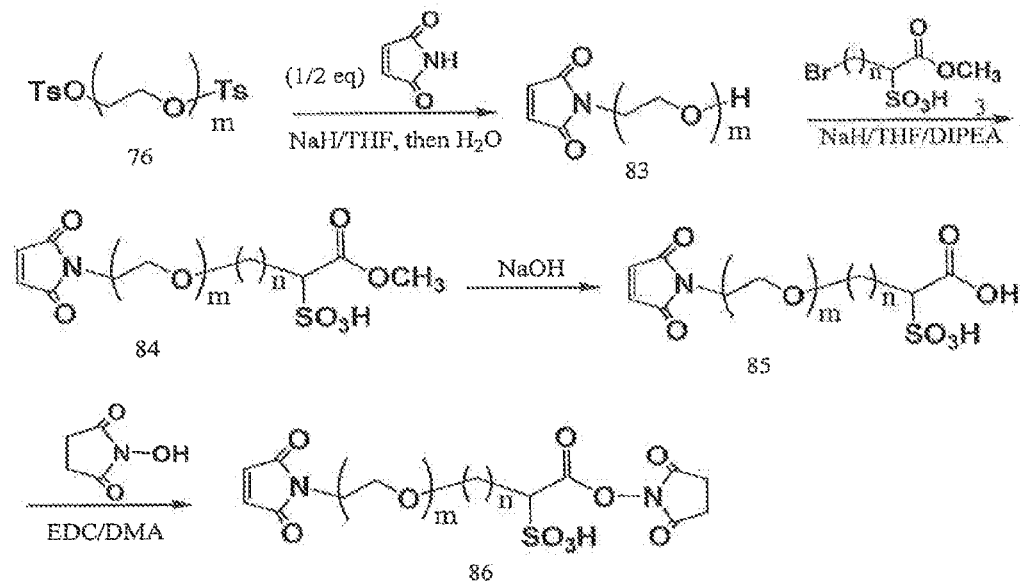
FIGS. 20 and 21 show the synthesis of various sulfonic acid-containing cross-linking reagents that contain a polyethyleneglycol (PEG) chain, along with a maleimido group and a reactive carboxylic acid ester.
Figure 21:
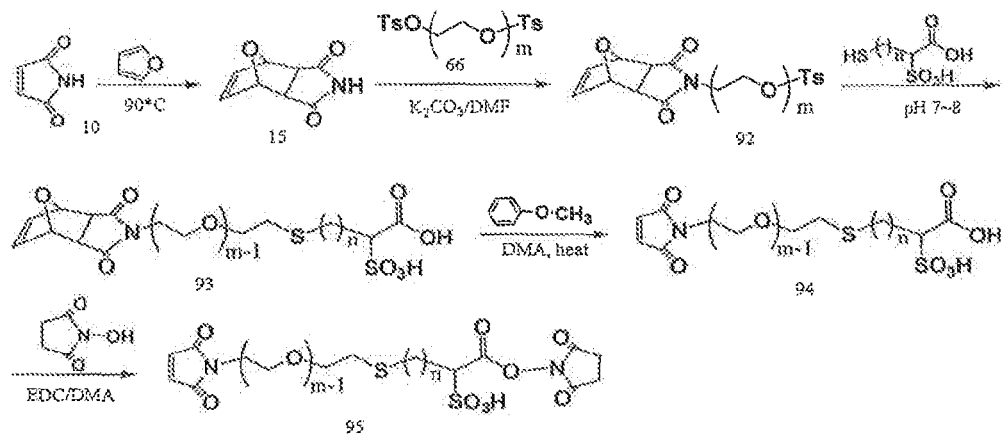
Figure 22:
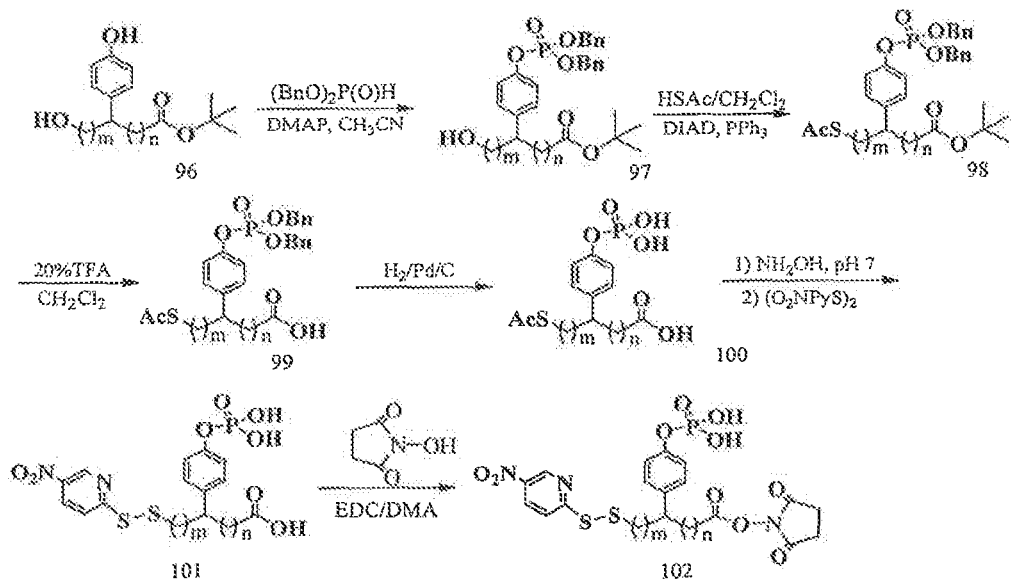
FIG. 22 shows the synthesis of phosphate-containing cross-linking reagents, where the phosphate substituent is attached to an aromatic group. These reagents also bear a reactive carboxylic acid ester and a nitropyridyldithio group that allows for linkage via disulfide bonds.
Figure 23:
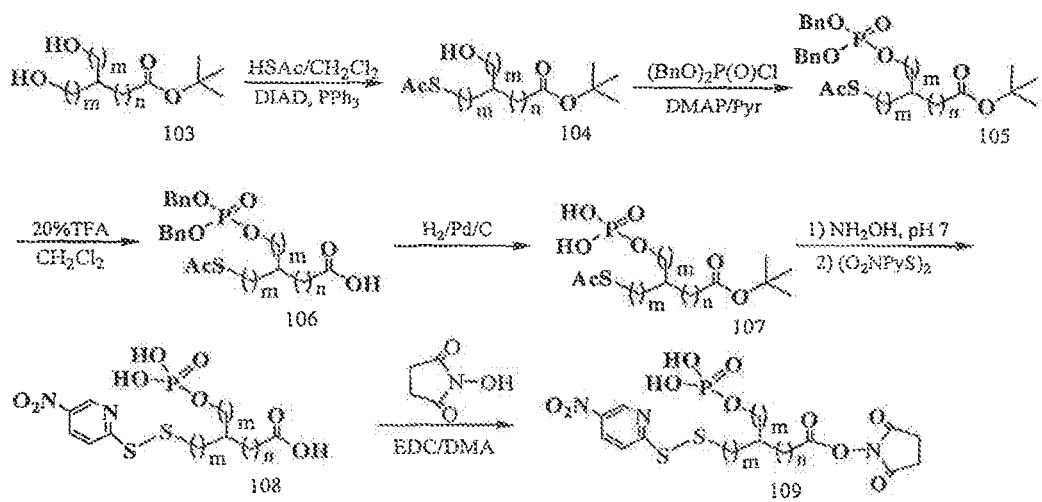
FIG. 23 shows the synthesis of phosphate-containing cross-linking reagents, where the phosphate substituent is attached to a branched alkyl group. These reagents also bear a reactive carboxylic acid ester and a nitropyridyldithio group that allows for linkage via disulfide bonds.
Figure 24:
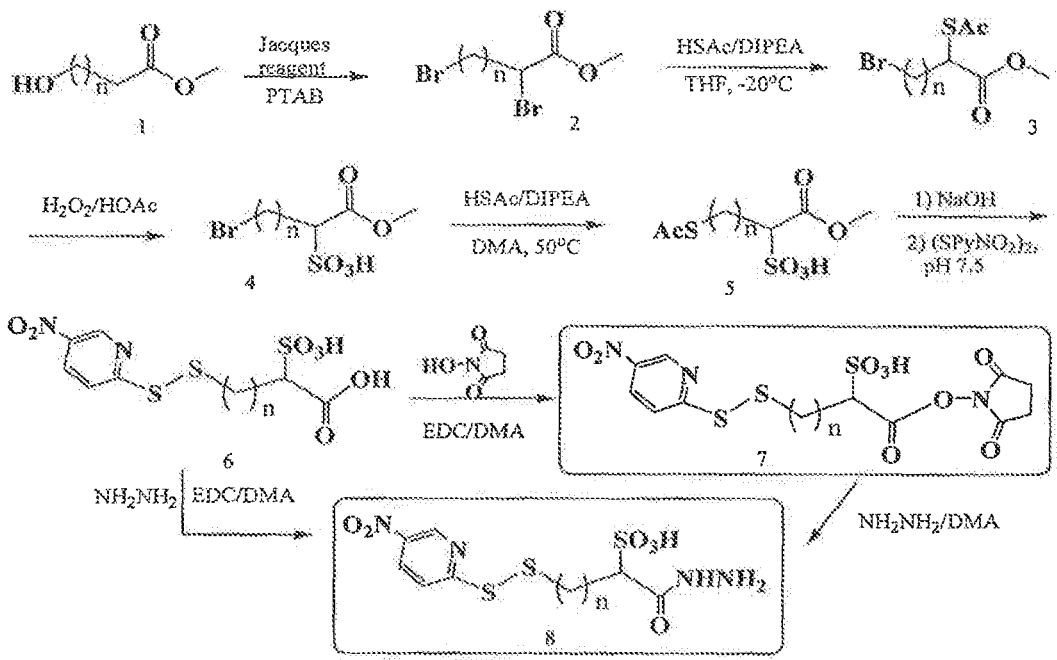
FIGS. 24-31 show the synthesis of sulfonate-containing cross-linking reagents that also incorporate a hydrazide moiety allowing for linkage via acid-labile bonds.
Figure 25:
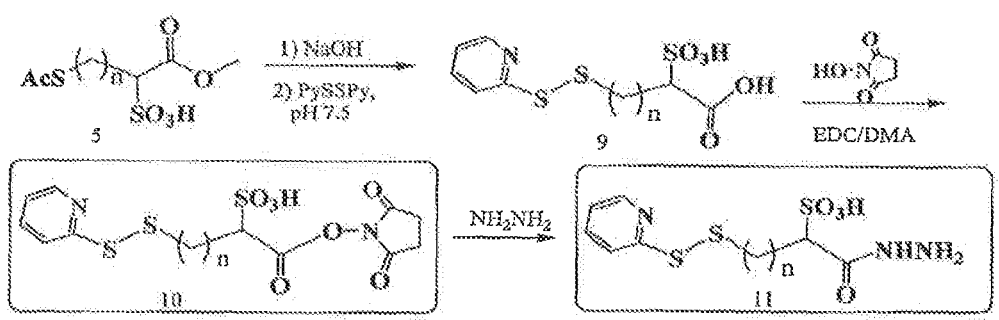
Figure 26:
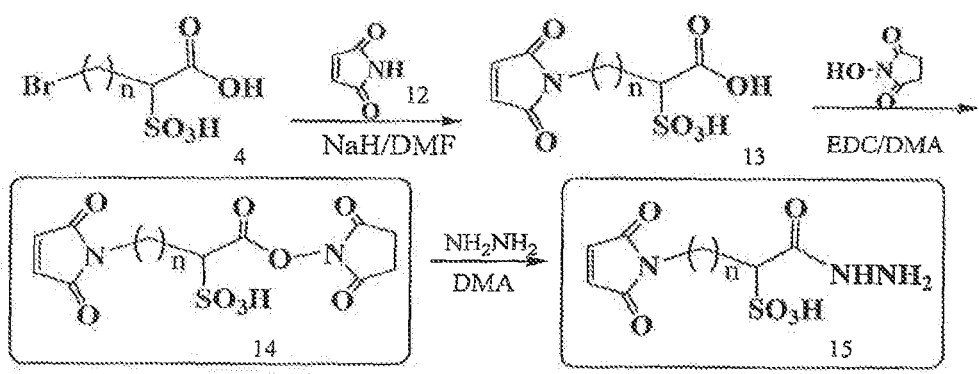
Figure 27:
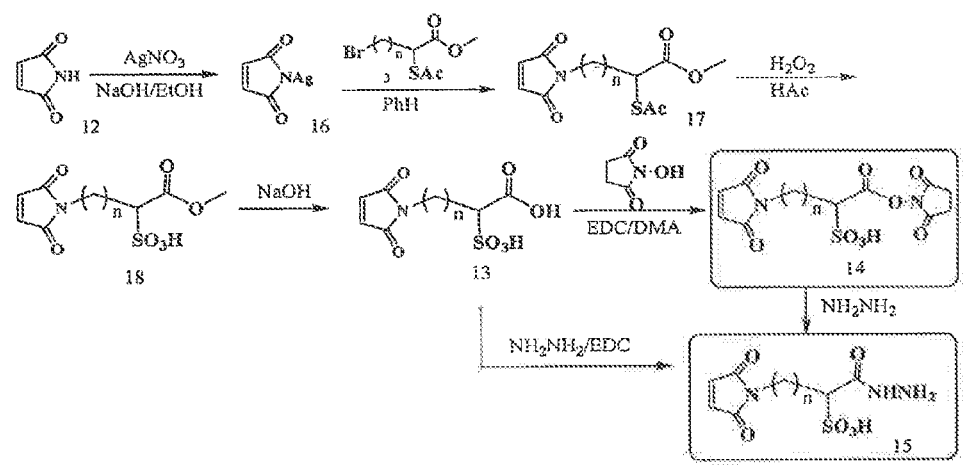
Figure 28:
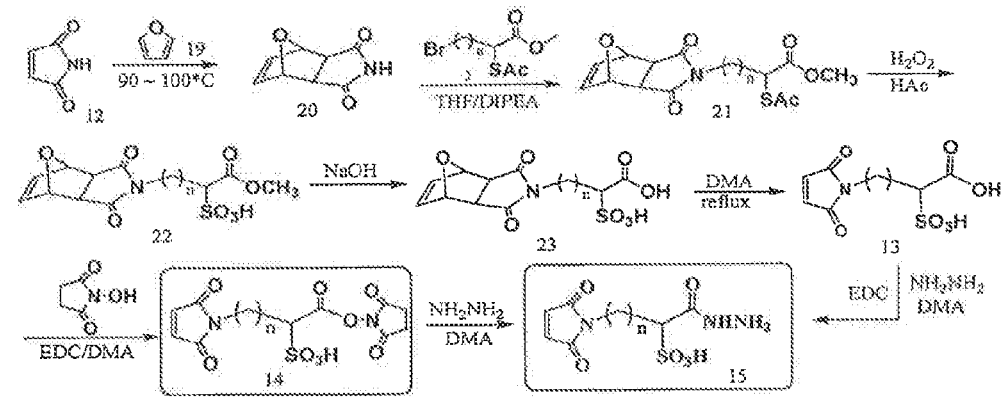
Figure 29:
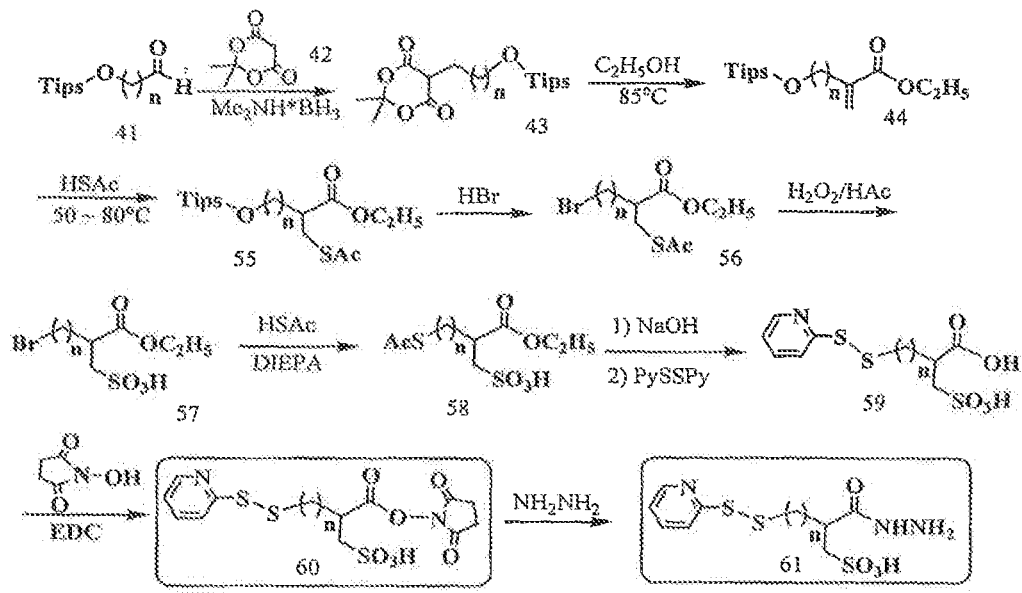
Figure 30:
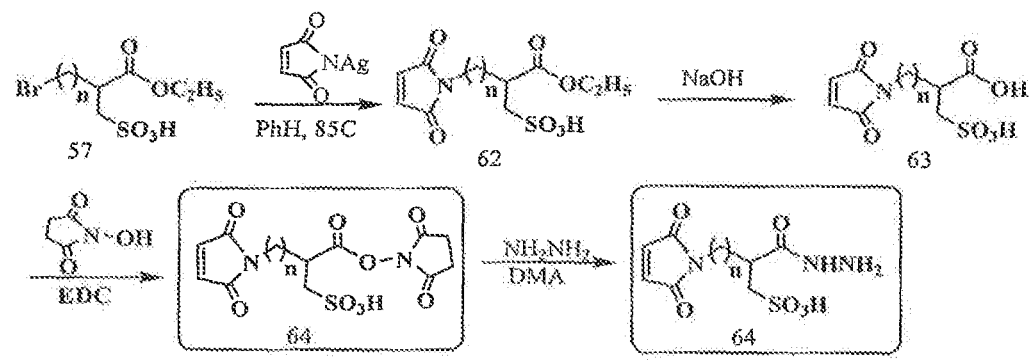
Figure 31:
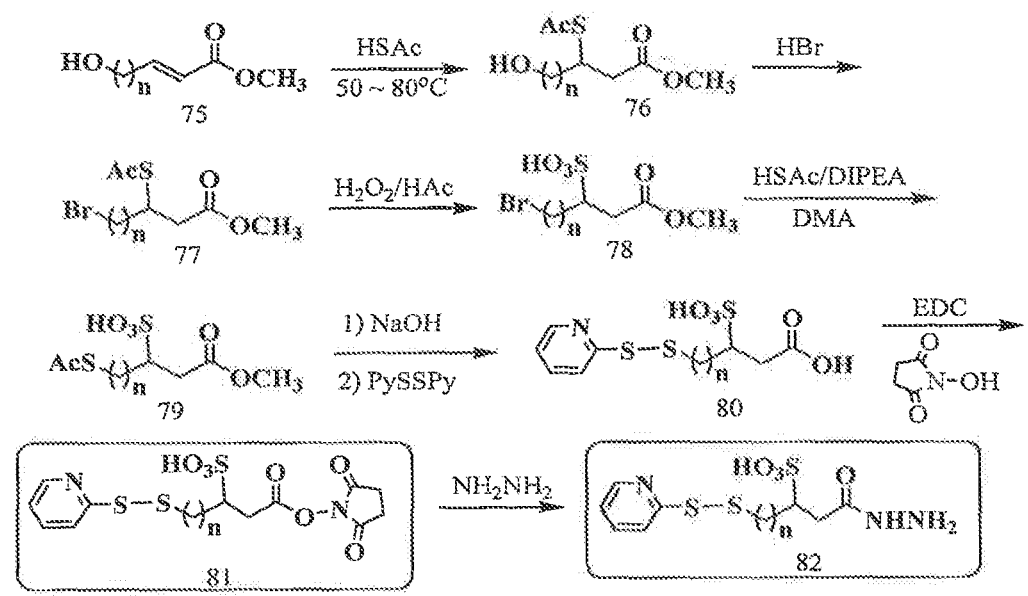
Figure 32:
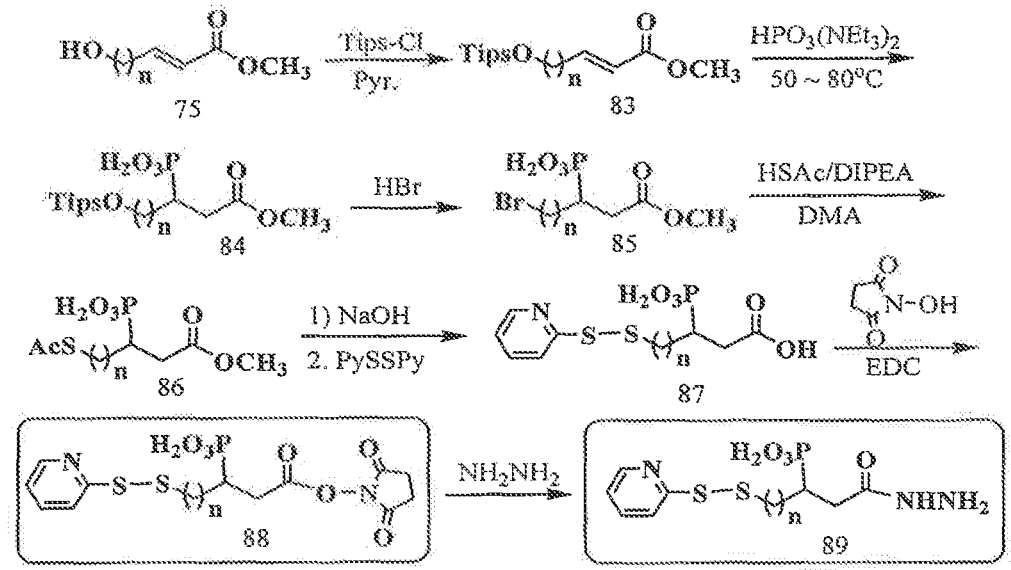
FIGS. 32-36 show the synthesis of phosphate-containing cross-linking reagents that also incorporate a hydrazide moiety allowing for linkage via acid-labile bonds.
Figure 33:
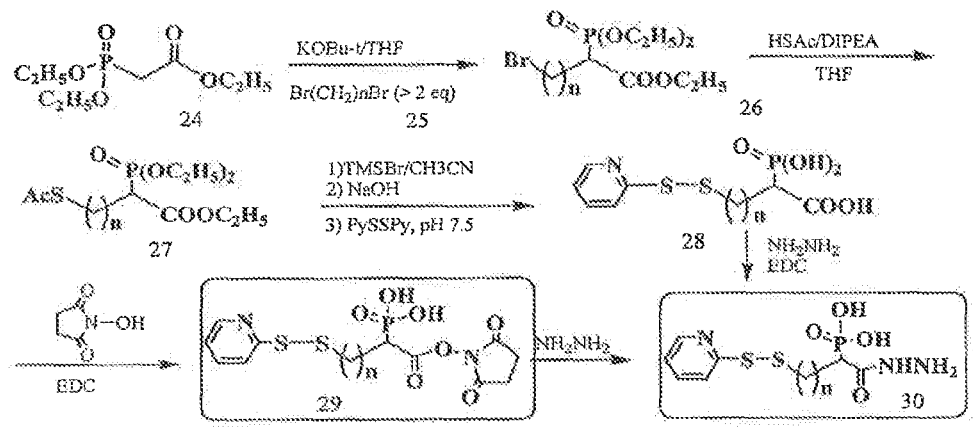
Figure 34:
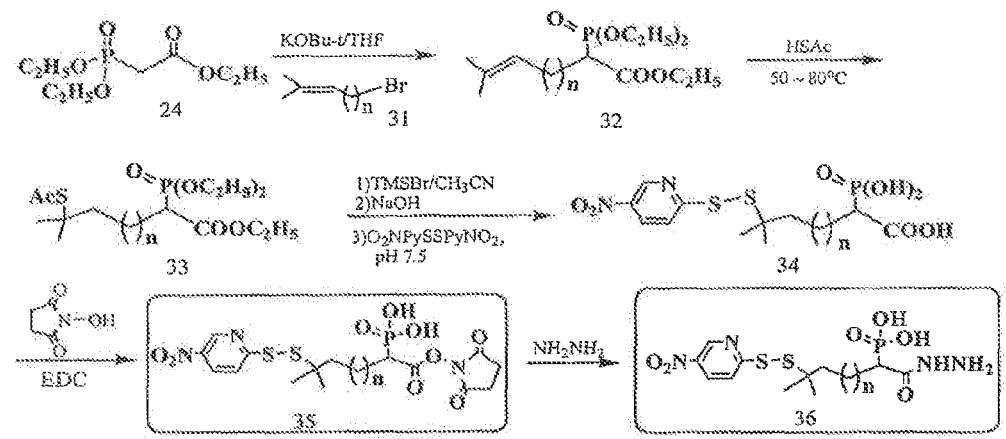
Figure 35:
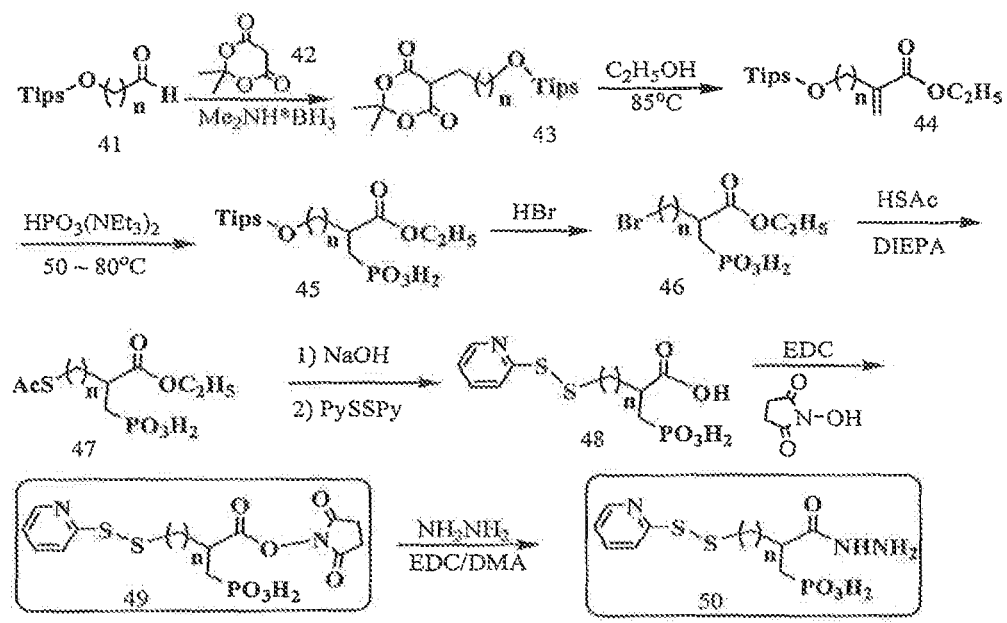
Figure 36:
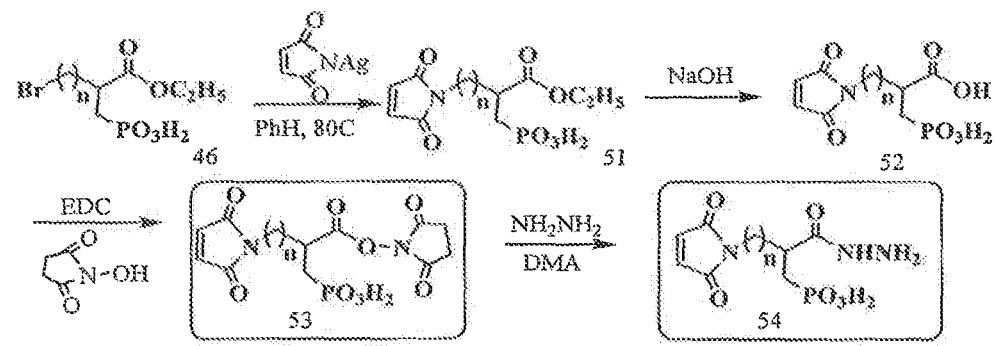
Figure 37:
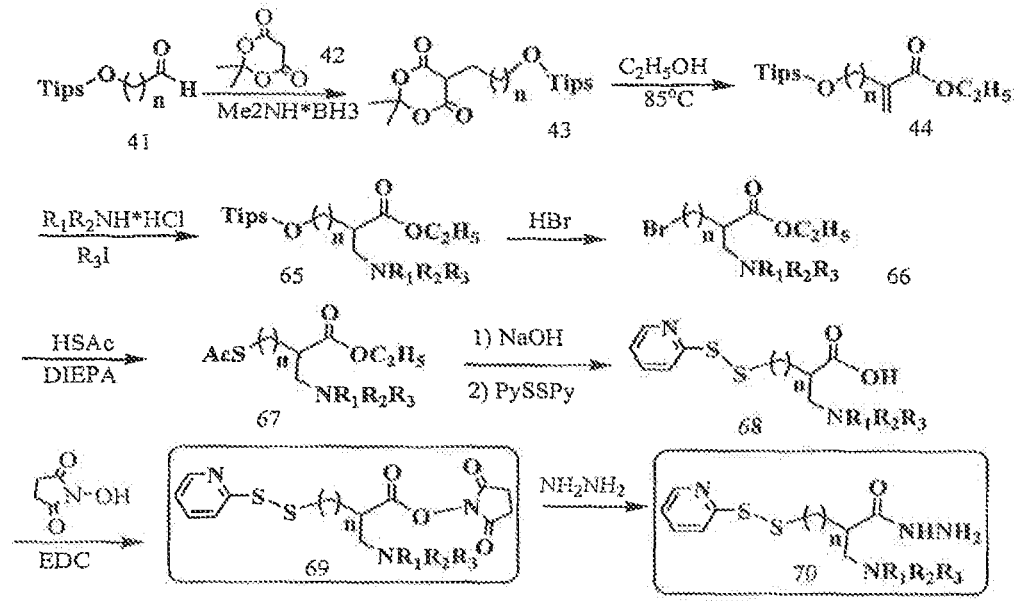
FIGS. 37-38 show the synthesis of quartenary amine-containing cross-linking reagents that also incorporate a hydrazide moiety allowing for linkage via acid-labile bonds.
Figure 50:
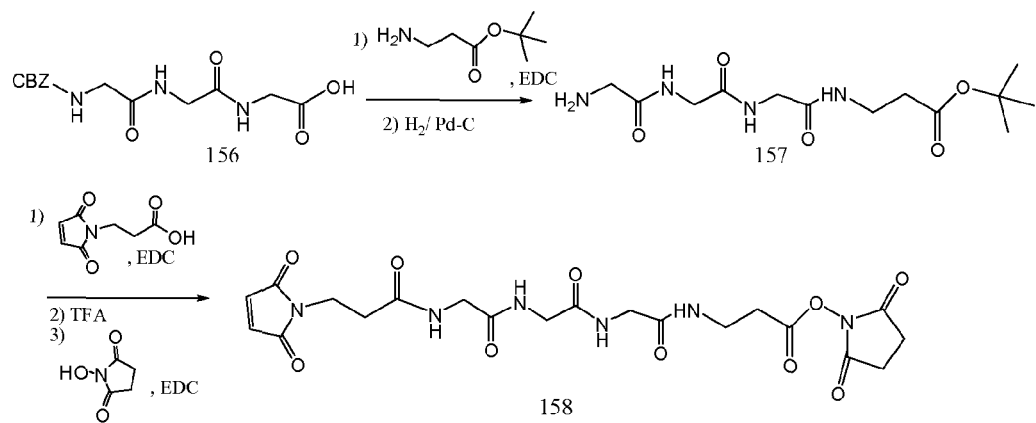
FIG. 50 shows the synthesis of a procharged linker that would generate a negatively charged carboxylate metabolite.
Figure 51:
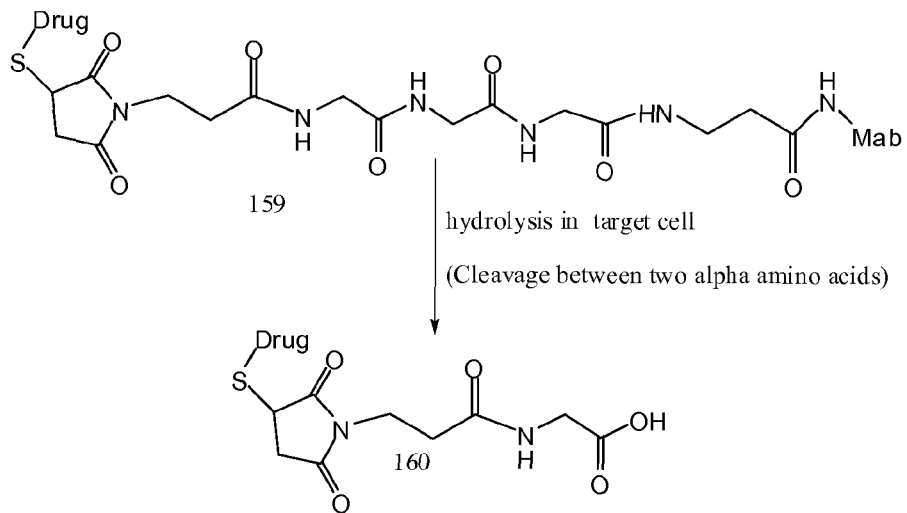
FIG. 51 shows a conjugate of linker 158 to a drug and a monoclonal antibody and how the conjugate would be processed in the lysosome of a target cell to give a metabolite containing the drug bearing a negatively charged carboxylate.
Figure 52:
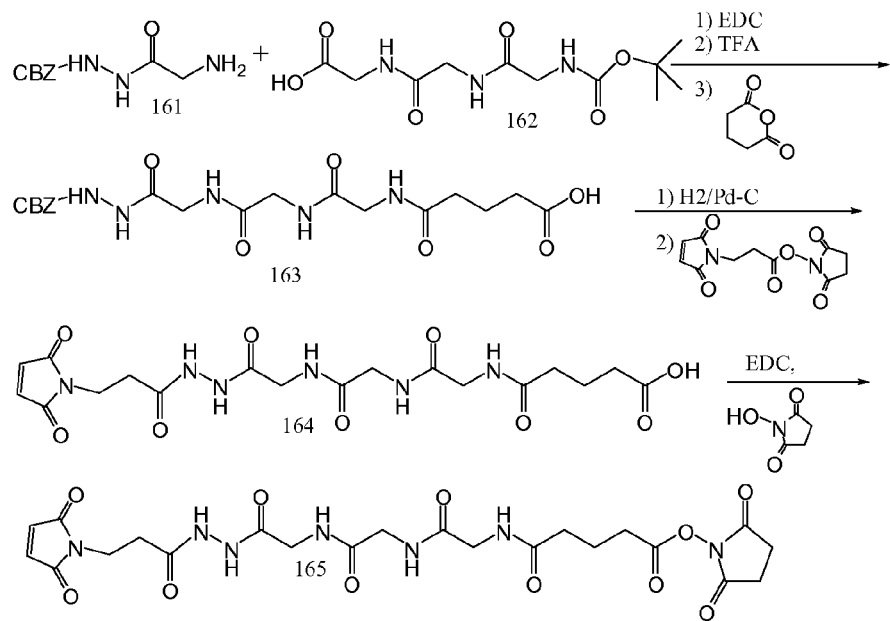
FIG. 52 shows the synthesis of a procharged linker that would generate a positively charged amine-containing metabolite.
Figure 53:
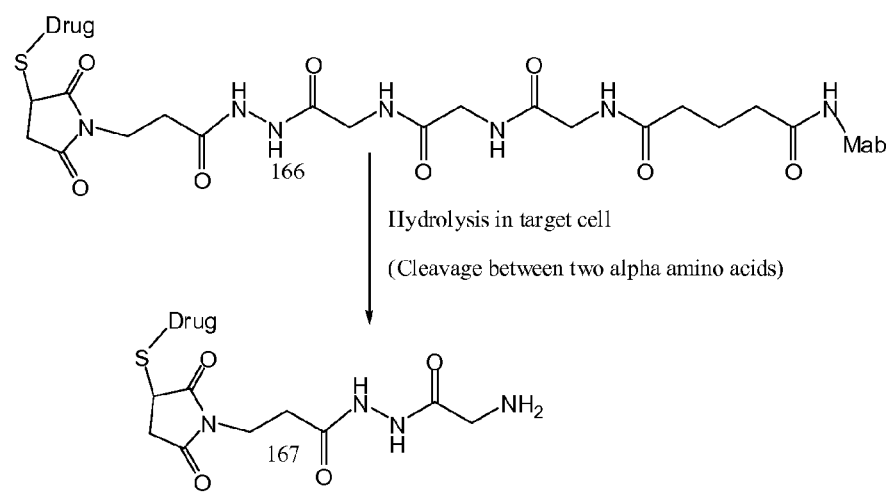
FIG. 53 shows a conjugate of a procharged linker to a drug and a monoclonal antibody and how the conjugate would be processed in the lysosome of a target cell to give a metabolite of the drug bearing a positively charged amine.
Figure 54:
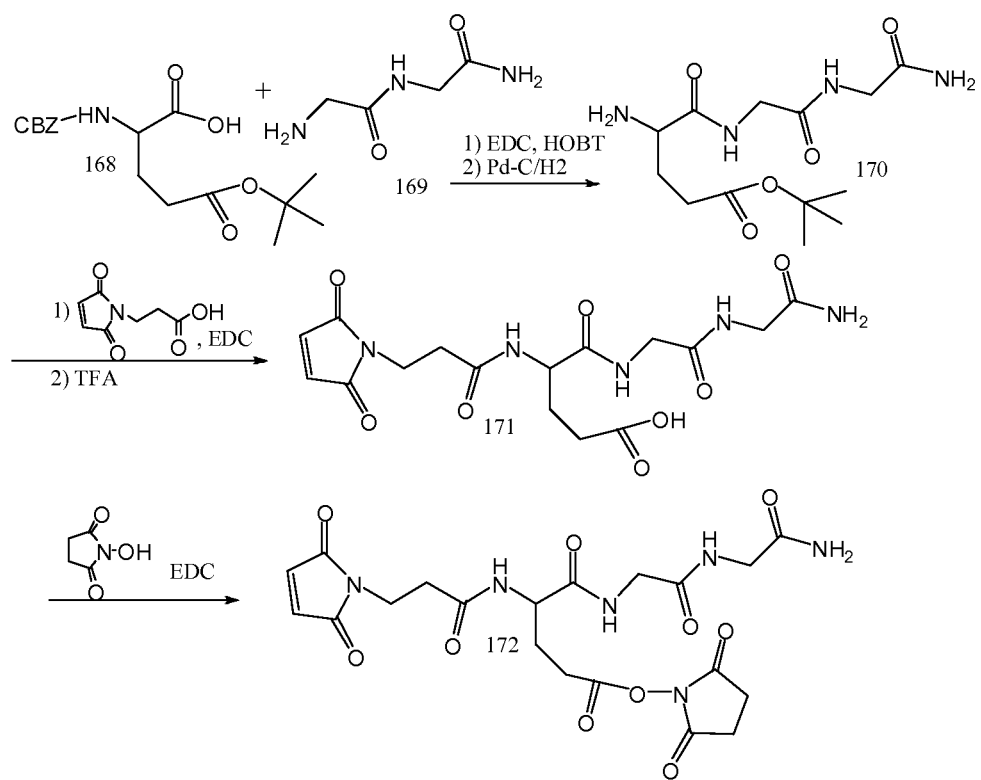
FIG. 54 shows the synthesis of a procharged linker that would generate a charged carboxylate metabolite.
Figure 55:
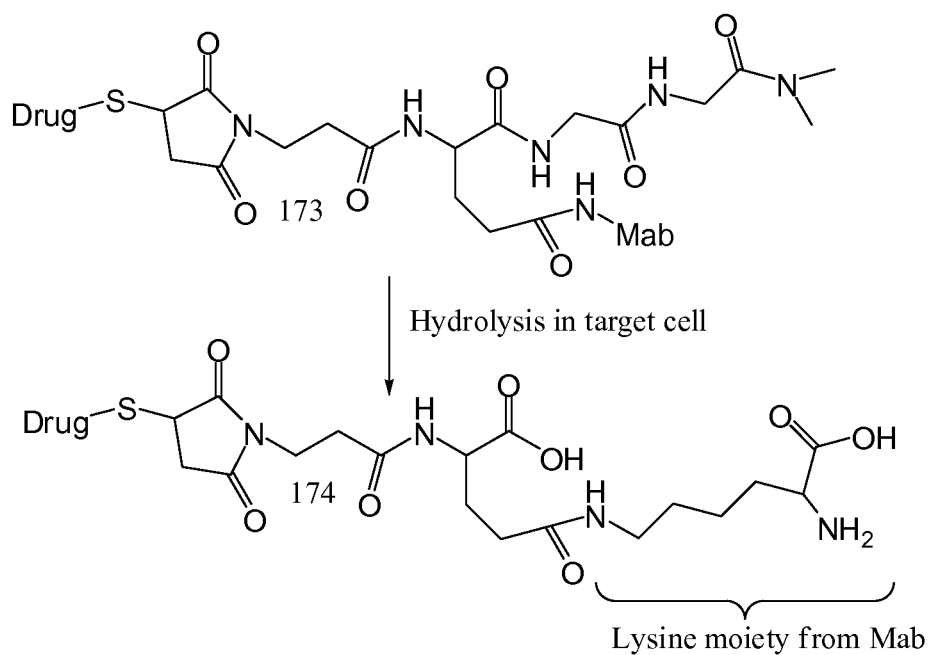
FIG. 55 shows a conjugate of linker 172 to a drug and a monoclonal antibody and how the conjugate would be processed in the lysosome of a target cell to give a metabolite containing the drug bearing a carboxylic acid and a lysine residue.

The synthetic routes to produce charged crosslinkers of the present invention are shown in FIGS. 1-49. Synthetic routes to produce linkers with pro-charged moieties are shown in FIGS. 50, 52, and 54. FIGS. 51, 53 and 55 show a conjugate of each of the respective pro-charged linkers with a drug and a monoclonal antibody and how these conjugates would be metabolized in a target cell to give charged metabolites. The crosslinkers possess three elements: a) a substituent that is either charged or will become charged when conjugates employing these linkers are metabolized in cells. The charge will be either anionic, such as but not limited to, carboxylate, sulfonate or phosphate, or cationic, such as but not limited to, a tertiary, quaternary, or primary amine or a nitrogen-containing heterocycle, b) a group, such as a N-hydroxysuccimimide ester, maleimido group, haloacetyl group, and hydrazide, capable of reaction with a cell-binding agent, and c) a group, such as but not limited to, a disulfide, maleimide, haloacetyl, and hydrazide, capable of reaction with a drug. The charged or pro-charged substituent can be introduced by methods described herein. For example, a sulfonate charge can be introduced by first treating a commercially available haloester compound with thioacetate to produce a thioacetyl compound, followed by oxidation of the thioacetyl group, using hydrogen peroxide, to a sulfonate group. Phosphate containing crosslinkers can be synthesized by methods described herein. First the desired reactive group, such as but not limited to, thiol, maleimide, haloacetyl and hydrazide, is introduced by the reactions shown in FIGS. 6-10, followed by hydrolysis of the phosphate ester to give the charged crosslinker bearing a phosphate. A positively charged quaternary amine substituent can be introduced in the crosslinker by reaction of an amine with an α,β-unsaturated ketone (see, for example, FIGS. 13 and 37). Alternatively a charged amine substituent can be introduced by displacement of a halogen with the amine or nitrogen containing heterocycle of choice.

Preferably, the cross-linkers are compounds of the formula (I) below:

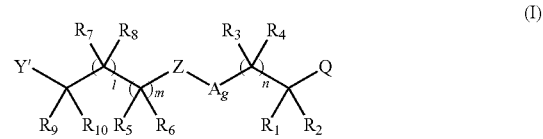

wherein Y' represents a functional group that enables reaction with a cell-binding agent;

Q represents a functional group that enables linkage of a drug via a disulfide, thioether, thioester, peptide, hydrazone, ester, ether, carbamate or amide bond;

$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, $X$—$SO_3^-$, $OPO_3^{2-}$, $X$—$OPO_3^{2-}$, $PO_3^{2-}$, $X$—$PO_3^{2-}$, $CO_2$—, cations, such as but not limited to, a nitrogen containing heterocycle, $N^+R_{11}R_{12}R_{13}$ or $X$—$N^+R_{11}R_{12}R_{13}$ or a phenyl, wherein:

$R_{11}$, $R_{12}$ and $R_{13}$ are the same or different and are H, linear alkyl having from 1 to 6 carbon atoms, or branched or cyclic alkyl having from 3 to 6 carbon atoms and X represents phenyl or a linear alkyl having from 1 to 6 carbon atoms, or a branched or cyclic alkyl having from 3 to 6 carbon atoms;

l, m and n are 0 or an integer from 1 to 4;

A is a phenyl or substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$. $X$—$SO_3^-$. $OPO_3^{2-}$, $X$—$OPO_3^{2-}$, $PO_3^{2-}$, $X$—$PO_3^{2-}$, $CO_2$—, and cations, such as but not limited to, a nitrogen containing heterocycle, $N^+R_{11}R_{12}R_{13}$ or $X$—$N^+R_{11}R_{12}R_{13}$, wherein X has the same definition as above, and wherein g is 0 or 1;

Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or NR14, wherein $R_{14}$ is H, a linear alkyl having from 1-6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent.

Examples of the functional group, Y', that enables reaction with a cell-binding agent include amine reacting agents such as but not limited to N-hydroxysuccinimide esters, p-nitrophenyl esters, dinitrophenyl esters, pentafluorophenyl esters; thiol reactive agents such as but not limited to pyridyldisulfides, nitropyridyldisulfides, maleimides, haloacetates and carboxylic acid chlorides.

Examples of the functional group, Q, which enables linkage of a cytotoxic drug, include groups that enable linkage via a disulfide, thioether, thioester, peptide, hydrazone, ester, carbamate, or amide bond. Such functional groups include, but are not limited to, thiol, disulfide, amino, carboxy, aldehydes, maleimido, haloacetyl, hydrazines, and hydroxy.

Examples of linear alkyls include methyl, ethyl, propyl, butyl, pentyl and hexyl. Examples of branched or cyclic alkyls having 3 to 6 carbon atoms include isopropyl, sec-butyl, isobutyl, tert-butyl, pentyl, hexyl, cyclopropyl, cyclobutyl, cyclopentyl, and cyclohexyl.

Examples of linear alkenyls having 2 to 6 carbon atoms include ethenyl, propenyl, butenyl, pentenyl, hexenyl. Examples of branched or cyclic alkenyls having 2 to 6 carbon atoms include isobutenyl, isopentenyl, 2-methyl-1-pentenyl, 2-methyl-2-pentenyl.

Examples of linear alkynyls having 2 to 6 carbon atoms include ethynyl, propynyl, butynyl, pentynyl, hexynyl. Examples of branched or cyclic alkynyls having up to 6 carbon atoms include 3-methyl-1-butynyl, 3-methyl-1-penynyl, 4-methyl-2-hexynyl.

In preferred embodiments, one of $R_1$, $R_2$, $R_3$, $R_4$, $R_9$, $R_{10}$ is a charged substituent selected from sulfonate, phosphate or trialkylammonium, and the rest are H, l, g and m are each 0, n=1, Q and Y' are each independently, a disulfide substituent, a maleimido, a haloacetyl group, or a N-hydroxy succinimide ester. In another more preferred embodiment, one of $R_1$, $R_2$, $R_3$, $R_4$, $R_9$, $R_{10}$ is a sulfonate, and the rest are H, l, g and m are each 0, n=1, Q is a disulfide, maleimido or haloacetyl moiety, and Y' is a maleimido moiety or a N-hydroxy succinimide ester. In a further more preferred embodiment, one of $R_1$, $R_2$, $R_3$, $R_4$, $R_9$, $R_{10}$ is a sulfonate, and the rest are H, l, g and m are each 0, n=1, Q is a pyridyldithio or nitropyridyldithio group, maleimido or haloacetyl moiety, and Y' is a N-hydroxy succinimide ester.

Figure 1:
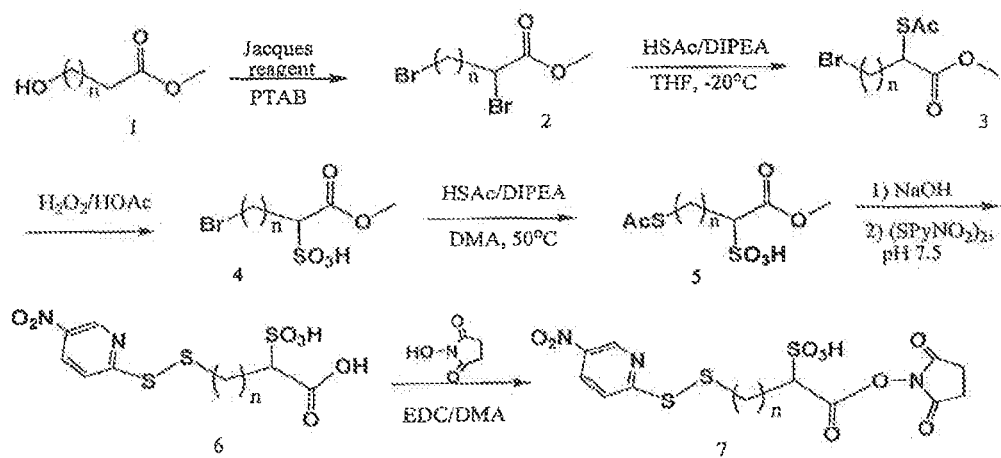
FIG. 1 shows the synthesis of sulfonic acid-containing cross-linking reagents that contain a nitropyridyldisulfide group and a reactive carboxylic acid ester. Hydroxyalkanoate esters are first converted into dibromoalkanoate esters as shown, followed by conversion of the α-bromo substituent into a sulfonic acid.
Figure 2:
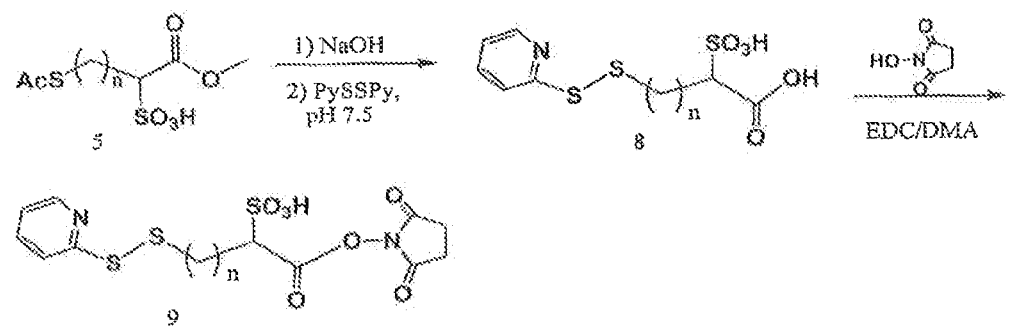
FIG. 2 shows the synthesis of sulfonic acid-containing cross-linking reagents that contain a pyridyldisulfide group and a reactive carboxylic acid ester.
Figure 3:
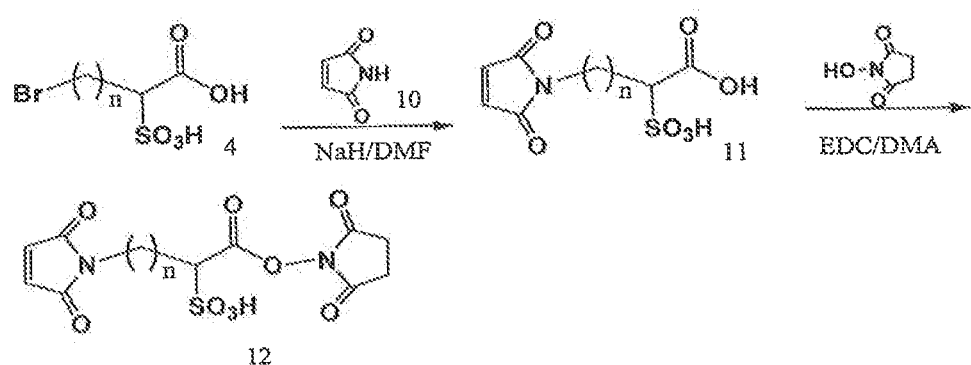
FIGS. 3, 4 and 5 show various routes for the synthesis of charged cross-linking agents bearing a reactive carboxylic acid ester and maleimido substituent, enabling linkage via thioether bonds.
Figure 4:
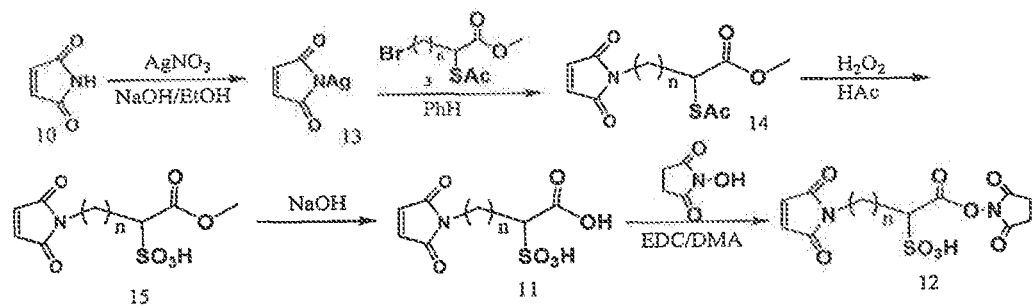
Figure 5:
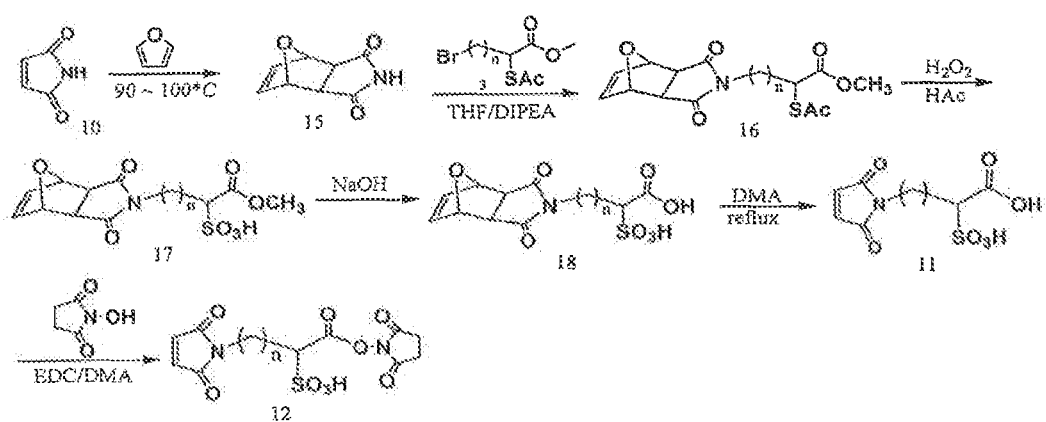
Figure 6:
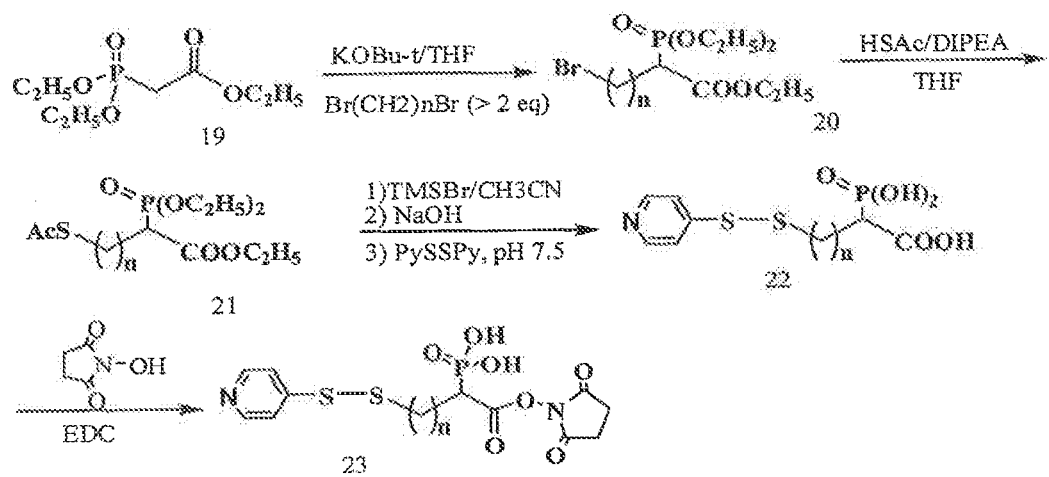
FIGS. 6 and 7 show the synthesis of phosphate-containing cross-linking reagents that contain a pyridyldisulfide group and a reactive carboxylic acid ester.

The synthesis of 2-dithionitropyridyl and 2-dithio-dinitropyridyl containing cross-linkers of formulae (I) is shown, for example, in FIGS. 1, 2 and the synthesis of the corresponding 4-dithionitropyridyl and 4-dithio-dinitropyridyl containing cross-linkers of the formula (I) is shown, for example, in FIG. 6. The synthesis of maleimido-containing charged cross linkers of the formula (I) with a sulfonate group is shown, for example, in FIGS. 3, 4 and 5. The synthesis of maleimido-containing charged cross linkers of the formula (I) with a phosphate group is shown, for example, in FIGS. 9 and 10. The synthesis of quaternary amine-containing charged crosslinkers of formula (I) is shown, for example, in FIGS. 13 and 14. The synthesis of polyethylene glycol-containing charged cross linkers of formula (I) are shown, for example, in FIGS. 17-21. The synthesis of charged cross linkers of formula (I) bearing a hydrazide moiety enabling linkage via acid-labile bonds is shown, for example, in FIGS. 24-36.

Cell-Binding Agent Drug-Conjugates

Figure 58:
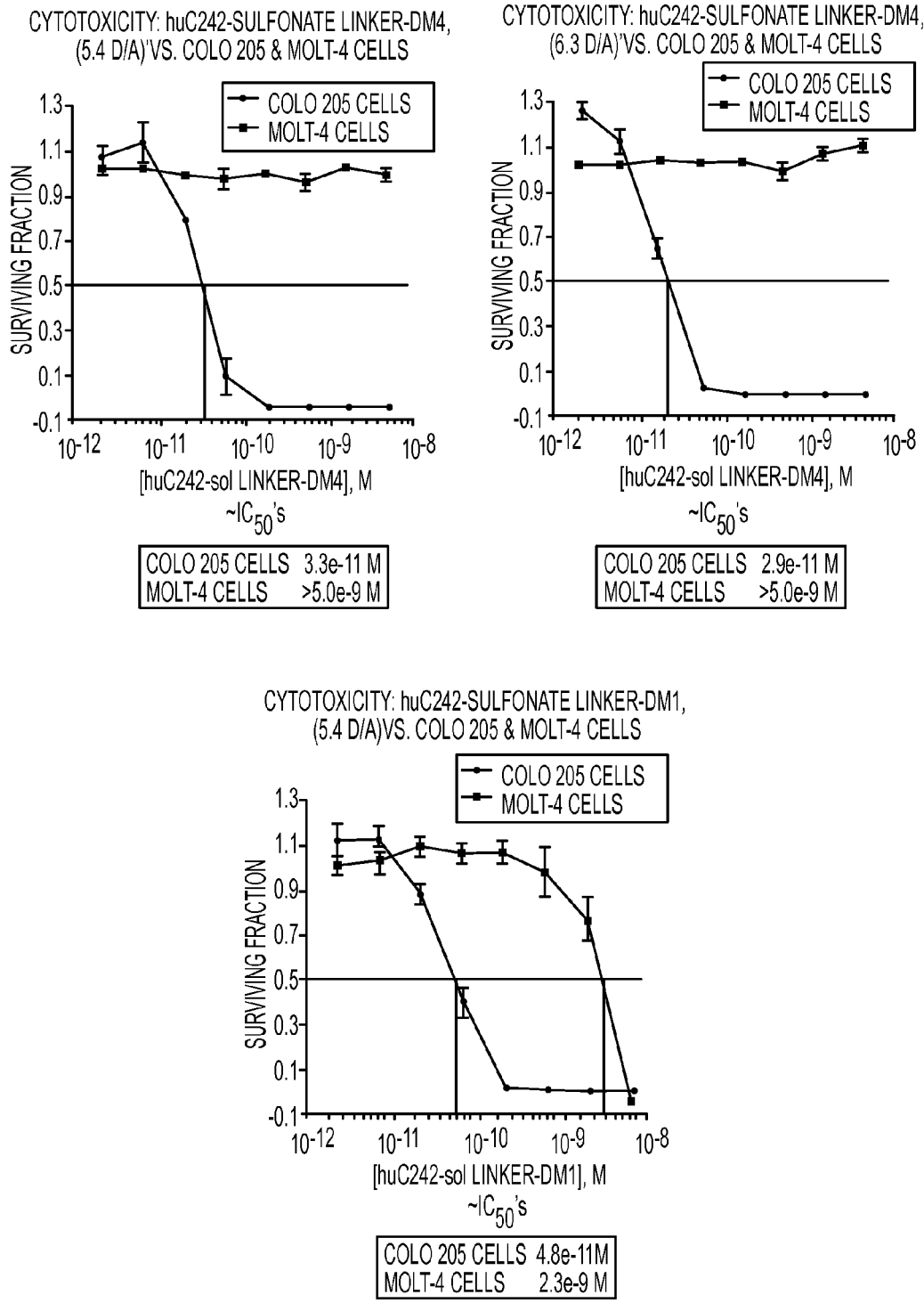
FIG. 58 shows the in vitro potency and target selectivity of cell-binding agent-drug conjugates bearing a charged crosslinker.
Figure 59:
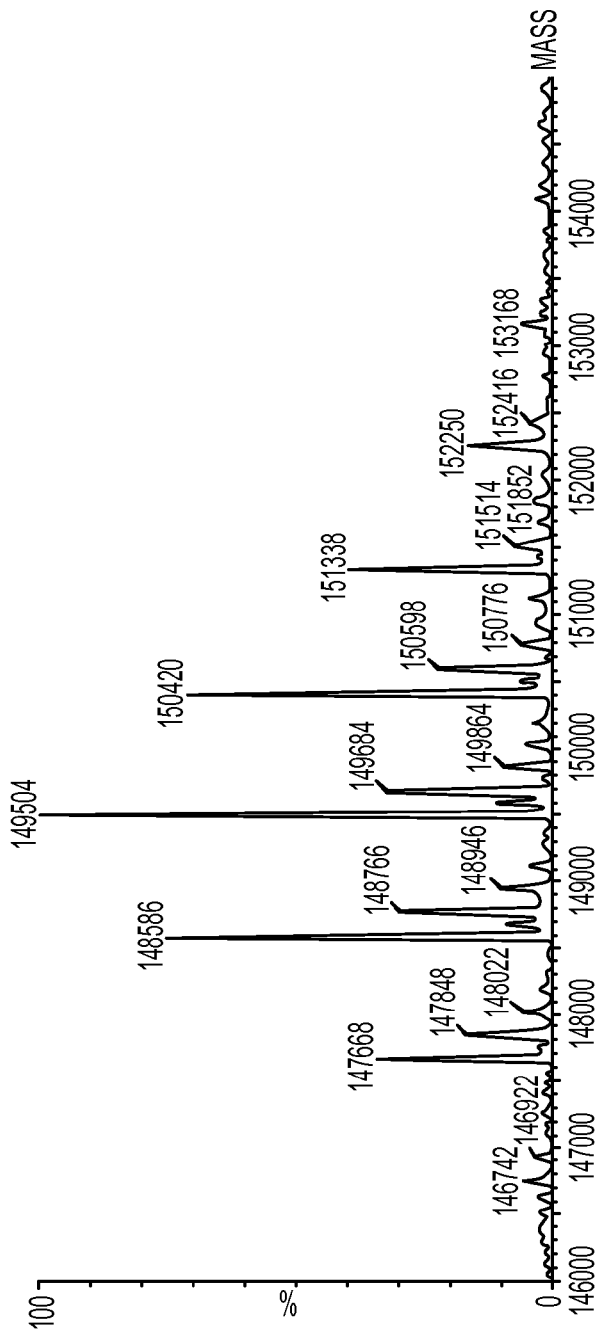
FIG. 59 shows the mass spectrum of cell-binding agent-drug conjugates (huC242-sulfonate linker-DM1 conjugates) bearing a charged crosslinker.

Using the charged or pro-charged crosslinkers a high number (>6) of drug molecules can be introduced. In non limiting examples, FIG. 57 exemplifies that cell-binding agent-drug conjugates prepared using a charged crosslinker of the present invention display high potency. In addition, the potency is target selective (see, for example, FIG. 58), since, even after linkage of a high number of drug molecules, the conjugate is highly potent towards target cells, but much less potent towards non-target cells. As exemplified in FIG. 59, mass spectral analysis demonstrates that the drugs are linked covalently to the cell-binding agent via the charged crosslinker.

The conjugates of the present invention can be represented by the following formula, CB-(-$L^c$-D)$_q$, wherein CB is a cell-binding agent, $L^c$ is a charged or pro-charged linker, D is a drug molecule, and q is an integer from 1 to 20.

Preferably, the conjugates have the following formula (II):

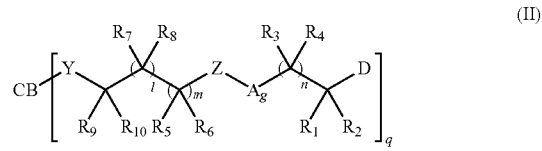

(II)

wherein CB represents a cell-binding agent,

D represents a drug linked to the cell-binding agent by a disulfide, thioether, thioester, peptide, hydrazone, ester, carbamate or amide bond;

$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$. $X$—$SO_3^-$. $OPO_3^{2-}$, $X$—$OPO_3^{2-}$, $PO_3^{2-}$, $X$—$PO_3^{2-}$, $CO_2^-$, cations, such as but not limited to, a nitrogen containing heterocycle, $N^+R_{11}R_{12}R_{13}$ or $X-N^+R_{11}R_{12}R_{13}$, or a phenyl, wherein:

$R_{11}$, $R_{12}$ and $R_{13}$ are same or different and are H, linear alkyl having from 1 to 6 carbon atoms, branched or cyclic alkyl having from 3 to 6 carbon atoms and X represents phenyl or a linear alkyl having from 1 to 6 carbon atoms, or a branched or cyclic alkyl having from 3 to 6 carbon atoms;

l, m and n are 0 or an integer from 1 to 4;

A is a phenyl or substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$. $X-SO_3^-$. $OPO_3^{2-}$, $X-OPO_3^{2-}$, $PO_3^{2-}$, $X-PO_3^{2-}$, $CO_2^-$, cations, such as but not limited to, a nitrogen containing heterocycle, $N^+R_{11}R_{12}R_{13}$ or $X-N^+R_{11}R_{12}R_{13}$, wherein X has the same definition as above, and wherein g is 0 or 1;

Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or NR14, wherein $R_{14}$ is H, a linear alkyl having from 1-6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent;

Y represents a carbonyl, thioether, amide, disulfide, or hydrazone group; and q is an integer from 1 to 20.

As described in more detail below, the drug can be any of many small molecule drugs, including, but not limited to, maytansinoids, CC-1065 analogs, morpholinos, doxorubicins, taxanes, cryptophycins, epothilones, calicheamicins, auristatins, and pyrrolobenzodiazepine dimers.

In preferred embodiments, one of $R_1$, $R_2$, $R_3$, $R_4$, $R_9$, $R_{10}$ is a charged substituent selected from sulfonate, phosphate, carboxylate or trialkylammonium, and the rest are H, l, g and m are each 0, n=1, D is a maytansinoid, a CC-1065 analog or a pyrrolobenzodiazepine dimer. In another more preferred embodiment, one of $R_1$, $R_2$, $R_3$, $R_4$, $R_9$, $R_{10}$ is a sulfonate, and the rest are H, l, g and m are each 0, n=1, D is a maytansinoid, CC-1065 analog or a pyrrolobenzodiazepine dimer linked via a disulfide, thioester, or thioether bond. In a further more preferred embodiment, one of $R_1$, $R_2$, $R_3$, $R_4$, $R_9$, $R_{10}$ is a sulfonate, and the rest are H, l, g and m are each 0, n=1, and Q is a maytansinoid, a CC-1065 analog, or a taxane.

In a preferred embodiment, when Z is an F1-E1-P-E2-F2 unit, E1 and E2 are the same or different and are C=O or NR14, wherein $R_{14}$ is H, a linear alkyl having from 1-6 carbon atoms, a branched or cyclic alkyl having from 3 to 6 carbon atoms, P is a peptide unit between 2 and 8 amino acids in length, wherein E1 or E2 can be linked to the peptide through the terminal nitrogen, terminal carbon or through a side chain of one of the amino acids of the peptide, preferred amino acid residues are glycine (gly), alanine (ala), leucine (leu), glutamic acid (glu), or lysine (lys), which can be used in any combination or any order (e.g., gly-gly-gly or ala-leu-ala-leu, etc.); and F1 and F2 are the same or different and are an optional polyethyleneoxy unit of formula $(OCH_2CH_2)_p$, wherein p is 0 or an integer from 2 to about 1000.

In a more preferred embodiment, when Z is an F1-E1-P-E2-F2 unit, E1 and E2 are the same or different and are C=O or NR14, wherein $R_{14}$ is H or a linear alkyl having from 1-6 carbon atoms, P is a peptide unit between 2 and 5 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to 24.

Preferably, q, the number of drugs bound to each cell-binding agent is 1-20, more preferably 2-18, and even more preferably 2-16, and most preferably 2-10.

To synthesize the conjugate, the cell-binding agent can be modified with the crosslinkers of the present invention to introduce reactive disulfide groups, maleimido, haloacetyl or hydrazide groups. Synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl modified cell-binding agent and a drug containing a free thiol group. Synthesis of conjugates bearing an acid labile hydrazone link can be achieved by reaction of a carbonyl group with the hydrazide moiety in the linker, by methods known in the art (see, for example, P. Hamann et al., *BioConjugate Chem.*, 13; 40-46, 2002; B. Laguzza et al., *J. Med. Chem.*, 32; 548-555, 1959; P. Trail et al., *Cancer Res.*, 57; 100-105, 1997).

Alternatively, the drug can be modified with the crosslinkers of the present invention to give a modified drug of formula (IV) bearing a functionality capable of reacting with a cell binding agent. For example a thiol-containing drug can be reacted with the charged or pro-charged crosslinker of formula (I) bearing a maleimido substituent at neutral pH in aqueous buffer to give a drug connected to the charged linker via a thioether link. A thiol-containing drug can undergo disulfide exchange with a charged linker bearing a pyridyldithio moiety to give a modified drug attached via a disulfide bond to the charged crosslinker. A drug bearing a hydroxyl group can be reacted with a charged or pro-charged crosslinker bearing a halogen, in the presence of a mild base, to give a modified drug bearing an ether link. A hydroxyl group containing drug can be condensed with a charged crosslinker of formula (I) bearing a carboxyl group, in the presence of a dehydrating agent, such as dicyclohexylcarbodimide, to give an ester link. An amino group containing drug can similarly undergo condensation with a carboxyl group on the charged or pro-charged crosslinker of formula (I) to give an amide bond.

The conjugate may be purified by standard biochemical means, such as gel filtration on a Sephadex G25 or Sephacryl S300 column, adsorption chromatography, and ion exchange or by dialysis as previously described. In some cases (e.g. folic acid, melanocyte stimulating hormone, EGF etc) the cell-binding agent-drug conjugates can be purified by chromatography such as by HPLC, medium pressure column chromatography or ion exchange.

Modified Cell-Binding Agents

The cell-binding agent modified by reaction with crosslinkers of the present invention are preferably represented by the formula (III)

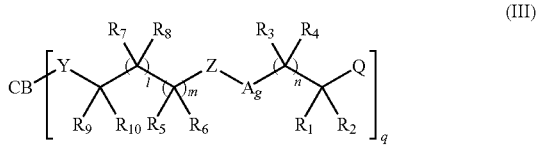

(III)

wherein the substituents are as described above for the charged or pro-charged linker and the cell-binding agent drug conjugate.

In preferred embodiments, one of $R_1$, $R_2$, $R_3$, $R_4$, $R_9$, $R_{10}$ is a charged substituent selected from sulfonate, phosphate, carboxyl or trialkylammonium, and the rest are H, l, g and m are each 0, n=1, Q is a disulfide substituent, a maleimido, haloacetyl group, or a N-hydroxy succinimide ester, and Y is thioether, amide, or disulfide. In another more preferred embodiment, one of $R_1$, $R_2$, $R_3$, $R_4$, $R_9$, $R_{10}$ is a sulfonate, and the rest are H, l, g and m are each 0, n=1, Q is a disulfide, maleimido or haloacetyl moiety, and Y is thioether, amide, or disulfide. In a further more preferred embodiment, one of $R_1$, $R_2$, $R_3$, $R_4$, $R_9$, $R_{10}$ is a sulfonate, and the rest are H, l, g and m are each 0, n=1, Q is a pyridyldithio or nitropyridyldithio group, and Y is thioether, amide, or disulfide.

In a preferred embodiment, when Z is an F1-E1-P-E2-F2 unit, E1 and E2 are the same or different and are C=O or $NR_{14}$, wherein $R_{14}$ is H, a linear alkyl having from 1-6 carbon atoms, a branched or cyclic alkyl having from 3 to 6 carbon atoms, P is a peptide unit between 2 and 8 amino acids in length, wherein E1 or E2 can be linked to the peptide through the terminal nitrogen, terminal carbon or through a side chain of one of the amino acids of the peptide, preferred amino acid residues are glycine (gly), alanine (ala), leucine (leu), glutamic acid (glu), or lysine (lys), which can be used in any combination or any order (e.g., gly-gly-gly or ala-leu-ala-leu, etc.); and F1 and F2 are the same or different and are an optional polyethyleneoxy unit of formula $(OCH_2CH_2)_p$, wherein p is 0 or an integer from 2 to about 1000.

In a more preferred embodiment, when Z is an F1-E1-P-E2-F2 unit, E1 and E2 are the same or different and are C=O or $NR_{14}$, wherein $R_{14}$ is H or a linear alkyl having from 1-6 carbon atoms, P is a peptide unit between 2 and 5 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to 24.

The modified cell-binding agent can be prepared by reacting the cell-binding agent with the charged crosslinkers by methods known in the art for other crosslinkers (U.S. Pat. Nos. 6,340,701 B1, 5,846,545, 5,585,499, 5,475,092, 5,414,064, 5,208,020, and 4,563,304; R. V. J. Chari et al. *Cancer Research* 52, 127-131, 1992; R. V. J. Chari et al. *Cancer Research* 55, 4079-4084, 1995; J. Carlsson et al. 173 *Biochem. J.* (1978) 723-737 (1978); Goff, D. A., Carroll, S. F. 1 BioConjugate Chem. 381-386 (1990); L. Delprino et al. 82 *J. Pharm. Sci.* 506-512 (1993); S. Arpicco et al., 8 *BioConjugate Chem* 327-337 (1997)). Advantageously, because the cross-linker groups are soluble in water or require only a small percentage of organic solvent to maintain solubility in aqueous solution, the reaction between the cell-binding agent and the cross-linker can be conducted in aqueous solution. The cross-linking reagent is dissolved in aqueous buffer, optionally containing a small amount (typically <10% by volume) of a polar organic solvent that is miscible with water, for example different alcohols, such as methanol, ethanol, and propanol, dimethyl formamide, dimethyl acetamide, or dimethylsulfoxide at a high concentration, for example 1-100 mM, and then an appropriate aliquot is added to the buffered aqueous solution of the cell-binding agent. An appropriate aliquot is an amount of solution that introduces 1-10 crosslinking groups per cell-binding agent, preferably 1-5 groups, and the volume to be added should not exceed 10%, preferably 5%, and most preferably 0-3% of the volume of the cell-binding agent solution. The aqueous solutions for the cell-binding agents are buffered between pH 6 and 9, preferably between 6.5 and 7.5 and can contain any non-nucleophilic buffer salts useful for these pH ranges. Typical buffers include phosphate, triethanolamine.HCl, HEPES, and MOPS buffers, which can contain additional components, such as sucrose and salts, for example, NaCl. After the addition the reaction is incubated at a temperature of from 4° C. to 40° C., preferably at ambient temperature. The progress of the reaction can be monitored by measuring the increase in the absorption at 495 nm or another appropriate wavelength. After the reaction is complete, isolation of the modified cell-binding agent can be performed in a routine way, using for example gel filtration chromatography, or adsorptive chromatography.

Figure 56:
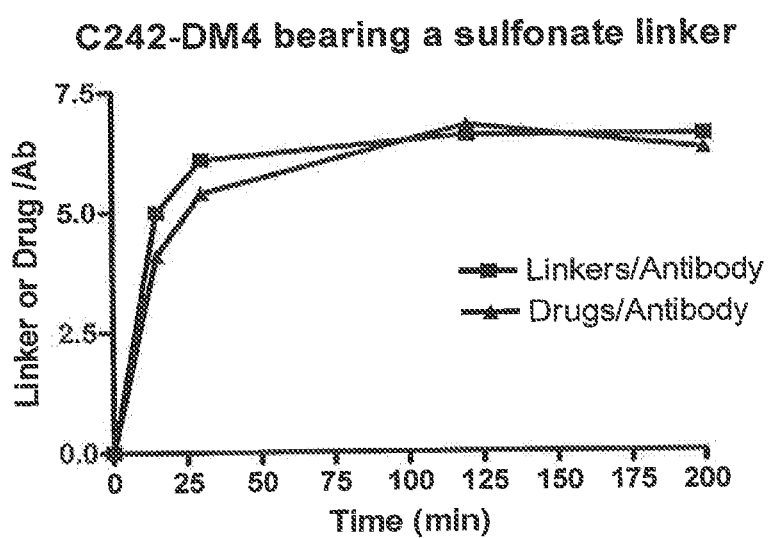
FIG. 56 shows the use of charged linker in modifying a cell-binding agent and producing a cell-binding agent-drug conjugate bearing a charged linker.

The extent of modification can be assessed by measuring the absorbance of the nitropyridine thione, dinitropyridine dithione, carboxamidopyridine dithione or dicarboxamidopyridine dithione group released. In a non limiting example, FIG. 56 shows the results from the modification of the cell-binding agent, the C242 antibody, with a sulfonate crosslinker of the present invention. The time course of linker/antibody (L/A) incorporation is shown, for example, along with the drugs/antibody (D/A) linked. The charged or pro-charged crosslinkers described herein have diverse functional groups that can react with any cell-binding agent that possesses a suitable substituent. For example cell-binding agents bearing an amino or hydroxyl substituent can react with crosslinkers bearing an N-hydroxysuccinimide ester, cell-binding agents bearing a thiol substituent can react with crosslinkers bearing a maleimido or haloacetyl group. Additionally, cell-binding agents bearing a carbonyl substituent can react with crosslinkers bearing a hydrazide. One skilled in the art can readily determine which crosslinker to use based on the known reactivity of the available functional group on the cell-binding agent.

Figure 71:
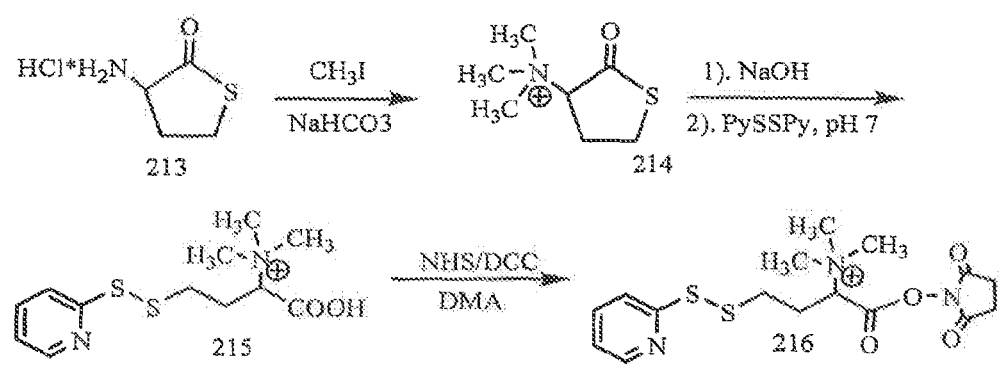
FIG. 71 shows the methods of synthesis of quarternary amine-containing cross-linking reagents. These reagents also bear a reactive carboxylic acid ester and a pyridyldithio group that allows for linkage via disulfide bonds.

Crosslinkers bearing a positive charge (for example, compound 214, FIG. 71) can be directly reacted with a cell binding agent in aqueous buffer at a pH between 5 and 9, optionally containing an organic cosolvent (such as 1 to 20% dimethylacetamide or ethanol) to provide a modified cell binding agent bearing a positive charge and a thiol group. The thiol group of the cell binding agent can be reacted with a cytotoxic drug bearing either a maleimido, haloacetamido or an active disulfide (example pyridyldithio, nitropyridyldithio group) to provide a conjugate. The conjugate can be purified by the methods described above.

Alternatively, crosslinkers bearing a positive charge and a reactive ester (for example, compound 216, FIG. 71) can be directly reacted with a cell binding agent (for example, through its lysine amino group) to introduce a positive charge and an active disulfide. Reaction with a thiol-containing cytotoxic drug as described above can provide a conjugate bearing a positive charge.

Modified Cytotoxic Drugs

The cytotoxic drugs modified by reaction with crosslinkers of the present invention are preferably represented by the formula (IV):

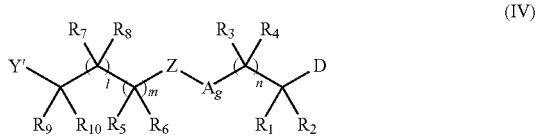

(IV)

wherein the substituents are as described above for the charged or pro-charged linker and the cell-binding agent drug conjugate.

In preferred embodiments, one of $R_1$, $R_2$, $R_3$, $R_4$, $R_9$, $R_{10}$ is a charged substituent selected from sulfonate, phosphate, carboxyl or trialkylammonium, and the rest are H, l, g and m are each 0, n=1, and Y' is a disulfide substituent, a maleimido, haloacetyl group, or a N-hydroxy succinimide ester. In another more preferred embodiment, one of $R_1$, $R_2$, $R_3$, $R_4$, $R_9$, $R_{10}$ is a sulfonate, and the rest are H, l, g and m are each 0, n=1, and Y' is a maleimido moiety or a N-hydroxy succinimide ester. In a further more preferred embodiment, one of $R_1$, $R_2$, $R_3$, $R_4$, $R_9$, $R_{10}$ is a sulfonate, and the rest are H, l, g and m are each 0, n=1, and Y' is a N-hydroxy succinimide ester.

In a preferred embodiment, when Z is an F1-E1-P-E2-F2 unit, E1 and E2 are the same or different and are C=O or NR14, wherein $R_{14}$ is H, a linear alkyl having from 1-6 carbon atoms, a branched or cyclic alkyl having from 3 to 6 carbon atoms, P is a peptide unit between 2 and 8 amino acids in length, wherein E1 or E2 can be linked to the peptide through the terminal nitrogen, terminal carbon or through a side chain of one of the amino acids of the peptide, preferred amino acid residues are glycine (gly), alanine (ala), leucine (leu), glutamic acid (glu), or lysine (lys), which can be used in any combination or any order (e.g., gly-gly-gly or ala-leu-ala-leu, etc.); and F1 and F2 are the same or different and are an optional polyethyleneoxy unit of formula $(OCH_2CH_2)_p$, wherein p is 0 or an integer from 2 to about 1000.

In a more preferred embodiment, when Z is an F1-E1-P-E2-F2 unit, E1 and E2 are the same or different and are C=O or NR14, wherein $R_{14}$ is H or a linear alkyl having from 1-6 carbon atoms, P is a peptide unit between 2 and 5 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to 24.

The modified drugs can be prepared by reacting the drug with the crosslinkers of the present invention to give a modified drug of formula (IV) bearing a functionality capable of reacting with a cell binding agent. For example a thiol-containing drug can be reacted with the charged or pro-charged crosslinker of formula (I) bearing a maleimido substituent at neutral pH in aqueous buffer to give a drug connected to the charged or pro-charged linker via a thioether link. A thiol-containing drug can undergo disulfide exchange with a charged or pro-charged linker bearing a pyridyldithio moiety to give a modified drug attached via a disulfide bond to the charged or pro-charged crosslinker. A drug bearing a hydroxyl group can be reacted with a charged crosslinker bearing a halogen, in the presence of a mild base, to give a modified drug bearing an ether link. A hydroxyl group containing drug can be condensed with a charged crosslinker of formula (I) bearing a carboxyl group, in the presence of a dehydrating agent, such as dicyclohexylcarbodiimide, to give an ester link. An amino group containing drug can similarly undergo condensation with a carboxyl group on the charged or pro-charged crosslinker of formula (I) to give an amide bond. The modified drug can be purified by standard methods such as column chromatography over silica gel or alumina, crystallization, preparatory thin layer chromatography, ion exchange chromatography or HPLC.

Cell-Binding Agents

The cell-binding agent that comprises the conjugates and the modified cell-binding agents of the present invention may be of any kind presently known, or that become known, and includes peptides and non-peptides. The cell-binding agent may be any compound that can bind a cell, either in a specific or non-specific manner. Generally, these can be antibodies (especially monoclonal antibodies and antibody fragments), adnectins (US Publication No.: 20070082365), interferons, lymphokines, hormones, growth factors, vitamins, nutrient-transport molecules (such as transferrin), or any other cell-binding molecule or substance.

Where the cell-binding agent is an antibody (for example, a murine, human humanized, resurfaced or a chimeric or any other antibody known to one of skill in the art), it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-13; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, mesothelin, cripto, $alpha_v beta_6$, integrins, VEGF, VEGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD23, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4, EpCAM and VCAM; a tumor associated antigen such as HER2, HER3 or HER4 receptor; and fragments of any of the above-listed polypeptides.

Preferred antigens for antibodies encompassed by the present invention also include CD proteins, such as CD3, CD4, CD8, CD19, CD20, CD34, and CD46; members of the ErbB receptor family, such as the EGF receptor, HER2, HER3 or HER4 receptor; cell adhesion molecules, such as LFA-1, Mac1, p150.95, VLA-4, ICAM-1, VCAM, EpCAM, alpha$_4$/beta$_7$ integrin, and alpha v/beta3 integrin including either alpha or beta subunits thereof (e.g. anti-CD11a, anti-CD18 or anti-CD11b antibodies); growth factors, such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. Preferred antibodies that can be used are antibodies to CD2, CD3, CD4, CD5, CD6, CD11, CD19, CD20, CD22, CD26, CD30, CD33, CD37, CD38, CD40, CD44, CD56, CD79, CD105, CD138, EphA receptors (e.g., EphA2 receptor), EphB receptors, EGFr, EGFRvIII, HER2, HER3, trastuzumab, pertuzumab mesothelin, cripto, alpha$_v$beta$_6$, integrins, VEGF, VEGFR, folate receptor (for example, FOLR1), transferrin receptor, GD3, EpCAM or an antibody which binds to one or more tumor-associated antigens or cell-surface receptors disclosed in US Publication No. 20080171040 or US Publication No. 20080305044 and are incorporated in their entirety by reference.

Additional examples of cell-binding agents that can be used include:
  resurfaced antibodies (U.S. Pat. No. 5,639,641);
  humanized or fully human antibodies, selected from but not limited to, huMy9-6, huB4, huC242, huN901, DS6, CD38, IGF-IR, CNTO 95, B-B4, trastuzumab, pertuzumab, bivatuzumab, sibrotuzumab, and rituximab (see, e.g., U.S. Pat. Nos. 5,639,641; 5,665,357; and 7,342,110, U.S. Provisional Patent Application No. 60/424,332, International Patent Application WO 02/16,401, U.S. Patent Publication Number 20060045877, U.S. Patent Publication Number 20060127407, U.S. Patent Publication Number 20050118183, Pedersen et al., (1994) *J. Mol. Biol.* 235, 959-973, Roguska et al., (1994) *Proceedings of the National Academy of Sciences*, Vol 91, 969-973, supra, Colomer et al., *Cancer Invest.*, 19: 49-56 (2001), Heider et al., *Eur. J. Cancer,* 31A: 2385-2391 (1995), Welt et al., *J. Clin. Oncol.*, 12: 1193-1203 (1994), and Maloney et al., *Blood,* 90: 2188-2195 (1997)); and
  epitope-binding fragments of antibodies such as sFv, Fab, Fab', and F(ab')$_2$ (Parham, *J. Immunol.* 131:2895-2902 (1983); Spring et al, *J. Immunol.* 113:470-478 (1974); Nisonoff et al, *Arch. Biochem. Biophys.* 89:230-244 (1960)).

Additional cell-binding agents include other cell-binding proteins and polypeptides exemplified by, but not limited to:
  Ankyrin repeat proteins (DARPins; Zahnd et al., *J. Biol. Chem.*, 281, 46, 35167-35175, (2006); Binz, H. K., Amstutz, P. & Pluckthun, A. (2005) *Nature Biotechnology,* 23, 1257-1268) or ankyrin-like repeats proteins or synthetic peptides described, for example, in U.S. Patent Publication Number 20070328667; U.S. Pat. No. 7,101,675; and WO/2007/147213; WO/2007/062466);
  interferons (e.g. α, β, γ);
  lymphokines such as IL-2, IL-3, IL-4, IL-6;
  hormones such as insulin, TRH (thyrotropin releasing hormones), MSH (melanocyte-stimulating hormone), steroid hormones, such as androgens and estrogens;
  vitamins such as folic acid;
  growth factors and colony-stimulating factors such as EGF, TGF-α, G-CSF, M-CSF and GM-CSF (Burgess, *Immunology Today* 5:155-158 (1984)); and
  transferrin (O'Keefe et al, *J. Biol. Chem.* 260:932-937 (1985)).

Monoclonal antibody techniques allow for the production of specific cell-binding agents in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; and Liming et al, WO 99/06587.)

Selection of the appropriate cell-binding agent is a matter of choice that depends upon the particular cell population that is to be targeted, but in general monoclonal antibodies and epitope binding fragments thereof are preferred, if an appropriate one is available.

For example, the monoclonal antibody My9 is a murine IgG$_{2a}$ antibody that is specific for the CD33 antigen found on Acute Myeloid Leukemia (AML) cells (Roy et al. *Blood* 77:2404-2412 (1991)) and can be used to treat AML patients. Similarly, the monoclonal antibody anti-B4 is a murine IgG$_1$, which binds to the CD19 antigen on B cells (Nadler et al, *J. Immunol.* 131:244-250 (1983)) and can be used if the target cells are B cells or diseased cells that express this antigen such as in non-Hodgkin's lymphoma or chronic lymphoblastic leukemia. Similarly, the antibody N901 is a murine monoclonal IgG$_1$ antibody that binds to CD56 found on small cell lung carcinoma cells and on cells of other tumors of the neuroendocrine origin (Roy et al. *J. Nat. Cancer Inst.* 88:1136-1145 (1996)), C242 antibody that binds to the CanAg antigen, pertuzumab, trastuzumab that binds to HER2/neu, and anti-EGF receptor antibody.

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers is also a suitable cell-binding agent.

Cancers of the breast and testes can be successfully targeted with estrogen (or estrogen analogues) or androgen (or androgen analogues), respectively, as cell-binding agents.

Drugs

Drugs that can be used in the present invention include chemotherapeutic agents. "Chemotherapeutic agent" is a chemical compound useful in the treatment of cancer. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimnidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are antihormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044 and are incorporated in their entirety by reference.

In a preferred embodiment, chemotherapeutic drugs are essentially small molecule drugs. A "small molecule drug" is broadly used herein to refer to an organic, inorganic, or organometallic compound that may have a molecular weight of for example 100 to 1500, more suitably from 120 to 1200, favorably from 200 to 1000, and typically having a molecular weight of less than about 1000. Small molecule drugs of the invention encompass oligopeptides and other biomolecules having a molecular weight of less than about 1000. Small molecule drugs are well characterized in the art, such as in WO05058367A2, European Patent Application Nos. 85901495 and 8590319, and in U.S. Pat. No. 4,956,303, among others and are incorporated in their entirety by reference.

Preferable small molecule drugs are those that allow for linkage to the cell-binding agent. The invention includes known drugs as well as those that may become known. Especially preferred small molecule drugs include cytotoxic agents.

The cytotoxic agent may be any compound that results in the death of a cell, or induces cell death, or in some manner decreases cell viability, wherein each cytotoxic agent comprises a thiol moiety.

Preferred cytotoxic agents are maytansinoid compounds, taxane compounds, CC-1065 compounds, daunorubicin compounds and doxorubicin compounds, pyrrolobenzodiazepine dimers, calicheamicins. Auristatins and analogues and derivatives thereof, some of which are described below.

Other cytotoxic agents, which are not necessarily small molecules, such as siRNA, are also encompassed within the scope of the instant invention. For example, siRNAs can be linked to the crosslinkers of the present invention by methods commonly used for the modification of oligonucleotides (see, for example, US Patent Publications 20050107325 and 20070213292). Thus the siRNA in its 3' or 5'-phosphoromidite form is reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. siRNA are described in detail in U.S. Patent Publication Numbers: 20070275465, 20070213292, 20070185050, 20070161595, 20070054279, 20060287260, 20060035254, 20060008822, 20050288244, 20050176667, which are incorporated herein in their entirety by reference.

Maytansinoids

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamitocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with H2S or P2S5);

(2) C-14-alkoxymethyl (demethoxy/CH2OR) (U.S. Pat. No. 4,331,598);

(3) C-14-hydroxymethyl or acyloxymethyl (CH2OH or CH2OAc) (U.S. Pat. No. 4,450,254) (prepared from Nocardia);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

The synthesis of thiol-containing maytansinoids useful in the present invention is fully disclosed in U.S. Pat. Nos. 5,208,020, 5,416,064, and U.S. Patent Application No. 20040235840.

Maytansinoids with a thiol moiety at the C-3 position, the C-14 position, the C-15 position or the C-20 position are all expected to be useful. The C-3 position is preferred and the C-3 position of maytansinol is especially preferred. Also preferred are an N-methyl-alanine-containing C-3 thiol moiety maytansinoid, and an N-methyl-cysteine-containing C-3 thiol moiety maytansinoid, and analogues of each.

Specific examples of N-methyl-alanine-containing C-3 thiol moiety maytansinoid derivatives useful in the present invention are represented by the formulae M1, M2, M3, M6 and M7.

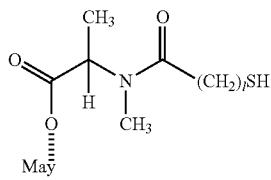

M1 wherein:
l is an integer of from 1 to 10; and
may is a maytansinoid.

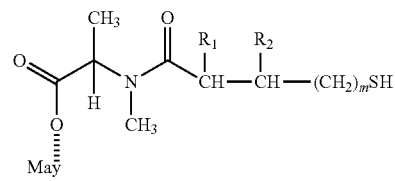

M2 wherein:
$R_1$ and $R_2$ are H, $CH_3$ or $CH_2CH_3$, and may be the same or different;
m is 0, 1, 2 or 3; and
may is a maytansinoid.

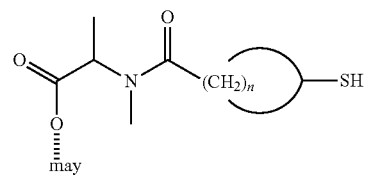

M3 wherein:
n is an integer of from 3 to 8; and
may is a maytansinoid.

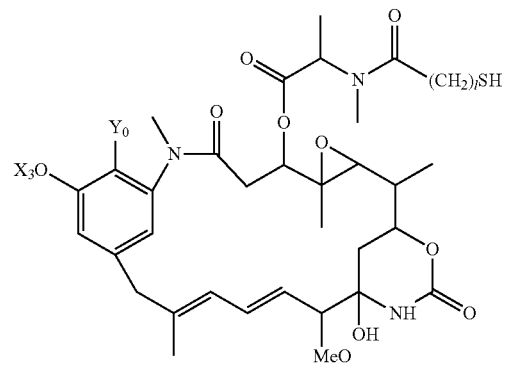

M6 wherein:
l is 1, 2 or 3;
$Y_0$ is Cl or H; and
$X_3$ is H or $CH_3$.

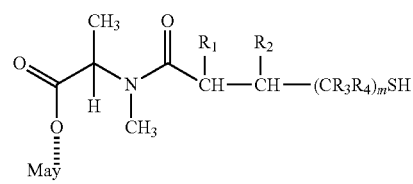

M7 wherein:
$R_1, R_2, R_3, R_4$ are H, $CH_3$ or $CH_2CH_3$, and may be the same or different;
m is 0, 1, 2 or 3; and
may is a maytansinoid.

Specific examples of N-methyl-cysteine-containing C-3 thiol moiety maytansinoid derivatives useful in the present invention are represented by the formulae M4 and M5.

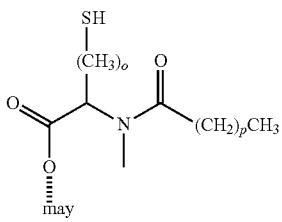

M4 wherein:
o is 1, 2 or 3;
p is an integer of 0 to 10; and
may is a maytansinoid.

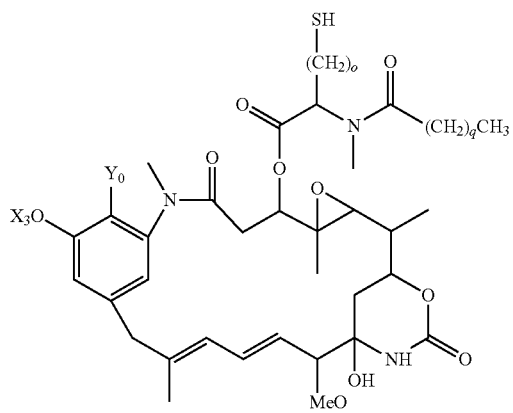

M5 wherein:
o is 1, 2 or 3;
q is an integer of from 0 to 10;
$Y_0$ is Cl or H; and
$X_3$ is H or $CH_3$.

Preferred maytansinoids are those described in U.S. Pat. Nos. 5,208,020; 5,416,064; 6,333.410; 6,441,163; 6,716,821; RE39,151 and 7,276,497.

Taxanes

The cytotoxic agent according to the present invention may also be a taxane.

Taxanes that can be used in the present invention have been modified to contain a thiol moiety. Some taxanes useful in the present invention have the formula T1 shown below:

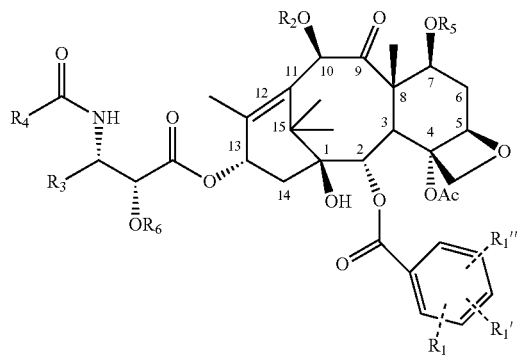

T1

Four embodiments of these novel taxanes are described below.

In embodiments (1), (2), (3), and (4), $R_1$, $R_1'$, and $R_1''$ are the same or different and are H, an electron withdrawing group, such as F, $NO_2$, CN, Cl, $CHF_2$, or $CF_3$ or an electron donating group, such as $-OCH_3$, $-OCH_2CH_3$, $-NR_7R_8$, $-OR_9$, wherein $R_7$ and $R_8$ are the same or different and are linear, branched, or cyclic alkyl groups having 1 to 10 carbon atoms or simple or substituted aryl having 1 to 10 carbon atoms. Preferably the number of carbon atoms for $R_7$ and $R_8$ is 1 to 4. Also, preferably $R_7$ and $R_8$ are the same. Examples of preferred $-NR_7R_8$ groups include dimethyl amino, diethyl amino, dipropyl amino, and dibutyl amino, where the butyl moiety is any of primary, secondary, tertiary or isobutyl. $R_9$ is linear, branched or cyclic alkyl having 1 to 10 carbon atoms.

$R_1$ preferably is $OCH_3$, F, $NO_2$, or $CF_3$.

Also preferably, $R_1$ is in the meta position and $R_1'$ and $R_1''$ are H or $OCH_3$.

$R_2$ in embodiments (1), (2) and (4), is H, heterocyclic, a linear, branched, or cyclic ester having from 1 to 10 carbon atoms or heterocyclic, a linear, branched, or cyclic ether having from 1 to 10 carbon atoms or a carbamate of the formula $-CONR_{10}R_{11}$, wherein $R_{10}$ and $R_{11}$ are the same or different and are H, linear alkyl having from 1-6 carbon atoms, branched, or cyclic alkyl having 3 to 10 atoms or simple or substituted aryl having 6 to 10 carbon atoms. For esters, preferred examples include $-COCH_2CH_3$ and $-COCH_2CH_2CH_3$. For ethers, preferred examples include $-CH_2CH_3$ and $-CH_2CH_2CH_3$. For carbamates, preferred examples include $-CONHCH_2CH_3$, $-CONHCH_2CH_2CH_3$, $-CO$-morpholino, $-CO$-piperazino, $-CO$-piperidino, or $-CO-N$-methylpiperazino.

$R_2$ in embodiment (3), is a thiol-containing moiety.

$R_3$ in embodiments (1), (3) and (4), is aryl, or is linear, branched or cyclic alkyl having 1 to 10 carbon atoms, preferably $-CH_2CH(CH_3)_2$.

$R_3$ in embodiment (2), is $-CH=C(CH_3)_2$.

$R_4$ in all four embodiments, is $-OC(CH_3)_3$ or $-C_6H_5$.

$R_5$ in embodiments (1) and (2), is a thiol-containing moiety and $R_6$ has the same definition as above for $R_2$ for embodiments (1), (2) and (4).

$R_5$ and $R_6$ in embodiment (3), are the same or different, and have the same definition as above for $R_2$ for embodiments (1), (2) and (4).

$R_5$ in embodiment (4), has the same definition as above for $R_2$ for embodiments (1), (2) and (4) and $R_6$ is a thiol moiety.

The preferred positions for introduction of the thiol-containing moiety are $R_2$ and $R_5$, with $R_2$ being the most preferred.

The side chain carrying the thiol moiety can be linear or branched, aromatic or heterocyclic. One of ordinary skill in the art can readily identify suitable side chains. Specific examples of thiol moieties include $-(CH_2)_nSH$, $-CO(CH_2)_nSH$, $-(CH_2)_nCH(CH_3)SH$, $-CO(CH_2)_nCH(CH_3)SH$, $-(CH_2)_nC(CH_3)_2SH$, $-CO(CH_2)_nC(CH_3)_2SH$, $-CONR_{12}(CH_2)_nSH$, $-CONR_{12}(CH_2)_nCH(CH_3)SH$, or $-CONR_{12}(CH_2)_nC(CH_3)_2SH$, $-CO$-morpholino-XSH, $-CO$-piperazino-XSH, $-CO$-piperidino-XSH, and $-CO-N$-methylpiperazino-XSH wherein X is a linear alkyl or branched alkyl having 1-10 carbon atoms.

$R_{12}$ is a linear alkyl, branched alkyl or cyclic alkyl having 1 to 10 carbon atoms, or simple or substituted aryl having from 1 to 10 carbon atoms or heterocyclic, and can be H, and n is an integer of 0 to 10.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups or alkoxy groups.

Examples of heterocyclics are compounds wherein the heteroatoms are selected from O, N, and S, and include morpholino, piperidino, piperazino, N-methylpiperazino, pyrrollyl, pyridyl, furyl and thiophene.

The taxanes having a thiol moiety can be synthesized according to known methods. The starting material for the synthesis is the commercially available 10-deacetylbaccatin III. The chemistry to introduce various substituents is described in several publications (Ojima et al, *J. Med. Chem.* 39:3889-3896 (1996); Ojima et al., *J. Med. Chem.* 40:267-278 (1997); Ojima et al., *Proc. Natl. Acad. Sci.,* 96:4256-4261 (1999); U.S. Pat. No. 5,475,011 and U.S. Pat. No. 5,811,452).

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. One of ordinary skill in the art can determine the appropriate chemical moiety for $R_1$ and the appropriate position for $R_1$ using only routine experimentation.

For example, electron withdrawing groups at the meta position increase the cytotoxic potency, while substitution at the para position is not expected to increase the potency as compared to the parent taxane. Typically, a few representative taxanes with substituents at the different positions (ortho, meta and para) will be initially prepared and evaluated for in vitro cytotoxicity.

The thiol moiety can be introduced at one of the positions where a hydroxyl group already exists. The chemistry to protect the various hydroxyl groups, while reacting the desired one, has been described previously (see, for example, the references cited supra). The substituent is introduced by simply converting the free hydroxyl group to a disulfide-containing ether, a disulfide-containing ester, or a disulfide-containing carbamate. This transformation is achieved as follows. The desired hydroxyl group is deprotonated by treatment with the commercially-available reagent lithium hexamethyldisilazane (1.2 equivalents) in tetrahydrofuran at −40° C. as described in Ojima et al. (1999), supra. The resulting alkoxide anion is then reacted with an excess of a dihalo compound, such as dibromoethane, to give a halo ether. Displacement of the halogen with a thiol (by reaction with potassium thioacetate and treatment with mild base or hydroxylamine) will provide the desired thiol-containing taxane.

Alternatively, the desired hydroxyl group can be esterified directly by reaction with an acyl halide, such as 3-bromopropionyl chloride, to give a bromo ester. Displacement of the bromo group by treatment with potassium thioacetate and further processing as described above will provide the thiol-containing taxane ester. Preferred taxoids are those described in U.S. Pat. Nos. 6,340,701; 6,372,738; 6,436,931; 6,596,757; 6,706,708; 7,008,942; 7,217,819 and 7,276,499.

CC-1065 Analogues

The cytotoxic agent according to the present invention may also be a CC-1065 analogue.

According to the present invention, the CC-1065 analogues contain an A subunit and a B or a B-C subunit. The A subunits are CPI (cyclopropapyrroloindole unit) in its natural closed cyclopropyl form or in its open chloromethyl form, or the closely related CBI unit (cyclopropylbenzindole unit) in the closed cyclopropyl form or the open chloromethyl form. The B and C subunits of CC-1065 analogues are very similar and are 2-carboxy-indole and 2-carboxy-benzofuran derivatives. For activity, the analogues of CC-1065 need at least one such 2-carboxy-indole subunit or 2-carboxy-benzofuran subunit, although two subunits (i.e., B-C) render the analogue more potent. As is obvious from the natural CC-1065 and from the analogues published (e.g., Warpehoski et al, *J. Med. Chem.* 31:590-603 (1988), D. Boger et al., *J. Org. Chem;* 66; 6654-6661, 2001; U.S. Pat. Nos. 5,739,350; 6,060,608; 6,310,209), the B and C subunits can also carry different substituents at different positions on the indole or benzofuran rings.

CC-1065 analogues containing a thiol moiety can be any of the following A subunits of the formulae A-1 {CPI (Cyclopropyl form)}, A-2 {CPI (Chloromethyl form)}, A-3 {CBI (Cyclopropyl form)}, and A-4 {CBI (Chloromethyl form)} covalently linked via an amide bond from the secondary amino group of the pyrrole moiety of the A subunit to the C-2 carboxy group of either a B subunit of the formula F-1 or a B-C subunit of the formulae F-3 or F-7.

A Subunits

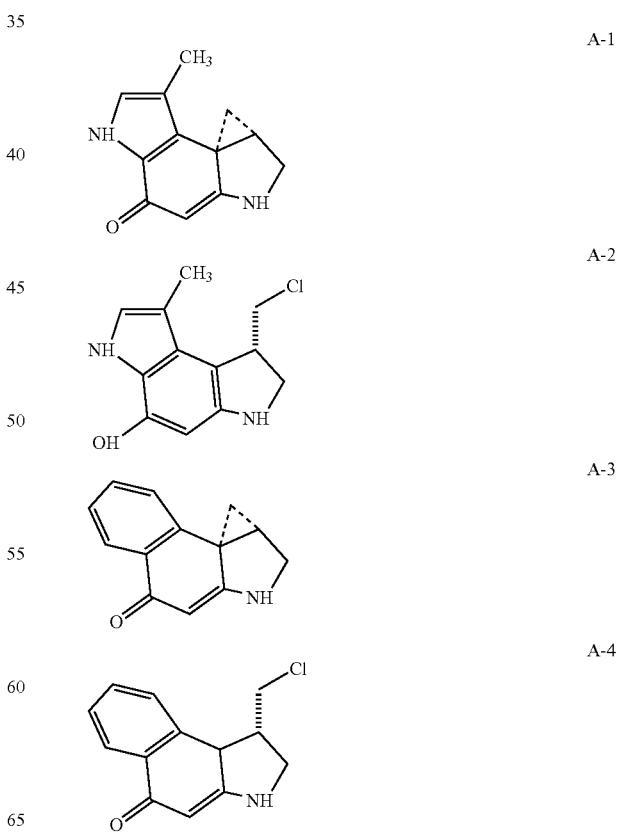

B and Covalently Bound B and C Subunits

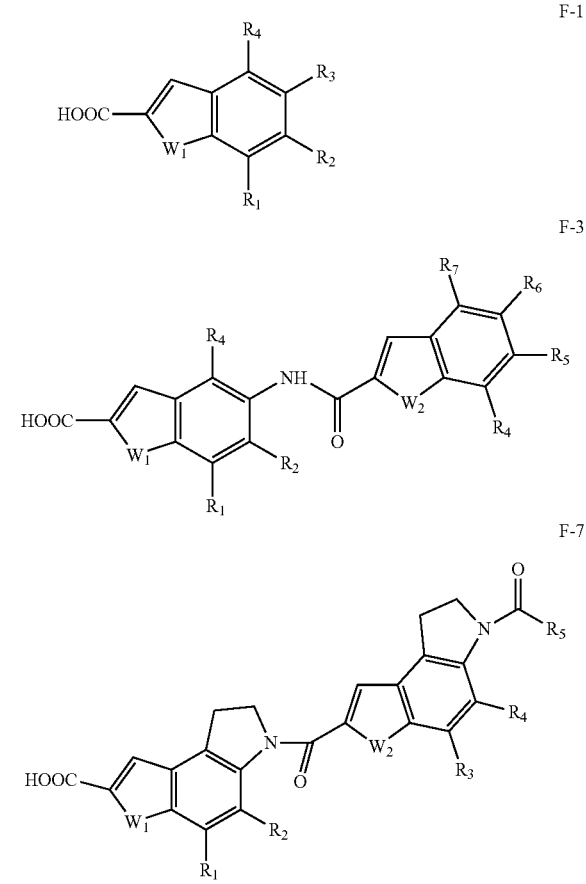

wherein each $W_1$ and $W_2$ may be the same or different and may be O or NH; and wherein, in Formula F-1 $R_4$ is a thiol moiety, in Formula F-3 one of R or $R_4$ is a thiol moiety, in Formula F-7 one of R' or $R_4$ is a thiol-containing moiety; when R or R' is a thiol moiety, then $R_1$ to $R_6$, which may be the same or different, are hydrogen, $C_1$-$C_3$ linear alkyl, methoxy, hydroxyl, primary amino, secondary amino, tertiary amino, or amido; and when $R_4$ is a thiol moiety, R, $R_1$, $R_2$, $R_3$, $R_4$, $R_5$ and $R_6$, which may be the same or different, are hydrogen, $C_1$-$C_3$ linear alkyl, methoxy, hydroxyl, primary amino, secondary amino, tertiary amino, or amido, and R' is $NH_2$, alkyl, O-alkyl, primary amino, secondary amino, tertiary amino, or amido. In addition, the chlorine atom in A-2 and A-4 subunits can be replaced with another suitable halogen.

In a preferred embodiment, R and R' are thiol moieties and $R_1$ and $R_2$ are each hydrogen. In another preferred embodiment, R and R' are thiol moieties and $R_1$ to $R_6$ are each hydrogen.

In an especially preferred embodiment, R or $R_4$ is —NHCO($CH_2$)$_l$SH, —NHCOC$_6$H$_4$($CH_2$)$_l$SH, or —O($CH_2$)$_l$SH, and R' is —($CH_2$)$_l$SH, —NH($CH_2$)$_l$SH or —O($CH_2$)$_l$SH wherein l is an integer of 1 to 10.

Examples of primary amines include methyl amine, ethyl amine and isopropyl amine.

Examples of secondary amines include dimethyl amine, diethylamine and ethylpropyl amine.

Examples of tertiary amines include trimethyl amine, triethyl amine, and ethyl-isopropyl-methyl amine.

Examples of amido groups include N-methylacetamido, N-methyl-propionamido, N-acetamido, and N-propionamido.

Examples of alkyl represented by R', when R' is not a linking group, include $C_1$-$C_5$ linear or branched alkyl.

Examples of O-alkyl represented by R' when R' is not a linking group, include compounds where the alkyl moiety is a $C_1$-$C_5$ linear or branched alkyl.

The above-described CC-1065 analogues may be isolated from natural sources and methods for their preparation, involving subsequent modification, synthetic preparation, or a combination of both, are well-described (see, e.g., U.S. Pat. Nos. 5,475,092, 5,585,499 and 5,846,545). Preferred CC-1065 analogs are those described in U.S. Pat. Nos. 5,475,092; 5,595,499; 5,846,545; 6,534,660; 6,586,618; 6,756,397 and 7,049,316

Daunorubicin/Doxorubicin Analogues

The cytotoxic agent according to the present invention may also be a daunorubicin analogue or a doxorubicin analogue.

The daunorubicin and doxorubicin analogues of the present invention can be modified to comprise a thiol moiety.

The modified doxorubicin/daunorubicin analogues useful in the present invention have the formula D1 shown below:

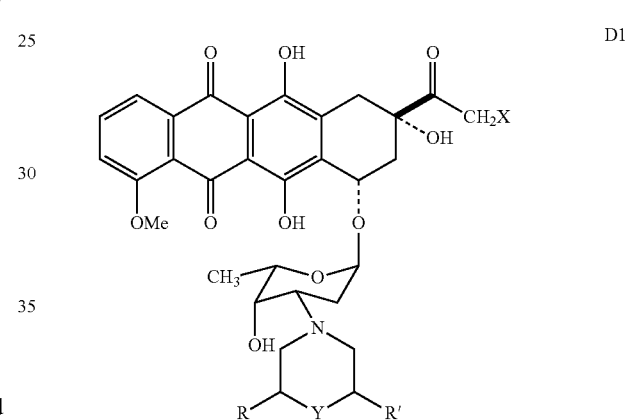

wherein,

X is H or OH;

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

In a preferred embodiment, $NR_2$ is $NCH_3$. In another preferred embodiment, R' is —O.

In an especially preferred embodiment, the thiol moiety is —($CH_2$)$_n$SH, —O($CH_2$)$_n$SH, —($CH_2$)$_n$CH($CH_3$)SH, —O($CH_2$)$_n$CH($CH_3$)SH, ($CH_2$)$_n$C($CH_3$)$_2$SH, or —O($CH_2$)$_n$C($CH_3$)$_2$SH, wherein n is an integer of 0 to 10.

Examples of the linear or branched alkyl having 1 to 5 carbon atoms, represented by R, $R_1$, and $R_2$, include methyl, ethyl, n-propyl, isopropyl, n-butyl, isobutyl, sec.-butyl, tert.-butyl, and pentyl, in any of its eight isomeric arrangements.

$R_1$ and $R_2$ preferably are methyl.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

When either R or R' is not a linking group, the substituent in that position can be varied until a compound of the desired toxicity is obtained. High toxicity is defined as having an IC$_{50}$ towards cultured cancer cells in the range of $1\times10^{-12}$ to $1\times10^{-9}$ M, upon a 72 hour exposure time. Representative examples of substituents are H, alkyl, and O-alkyl, as described above. One of ordinary skill in the art can determine the appropriate chemical moiety for R and R' using only routine experimentation.

For example, methyl and methoxy substituents are expected to increase the cytotoxic potency, while a hydrogen is not expected to increase the potency as compared to the parent daunorubicin analogues with substituents at the different positions will be initially prepared and evaluated for in vitro cytotoxicity.

The modified doxorubicin/daunorubicin analogues of the present invention, which have a thiol moiety, are described in WO 01/38318. The modified doxorubicin/daunorubicin analogues can be synthesized according to known methods (see, e.g., U.S. Pat. No. 5,146,064).

Auristatin include auristatin E, auristatin EB (AEB), auristatin EFP (AEFP), monomethyl auristatin E (MMAE) and are described in U.S. Pat. No. 5,635,483, Int. J. Oncol. 15:367-72 (1999); Molecular Cancer Therapeutics, vol. 3, No. 8, pp. 921-932 (2004); U.S. application Ser. No. 11/134,826. U.S. Patent Publication Nos. 20060074008, 2006022925.

The cytotoxic agents according to the present invention include pyrrolobenzodiazepine dimers that are known in the art (U.S. Pat. Nos. 7,049,311; 7,067,511; 6,951,853; 7,189,710; 6,884,799; 6,660,856.

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

Therapeutic Use

The cell-binding agent drug conjugates (e.g., immunoconjugates) of this invention can also be used in combination with other chemotherapeutic agents. Such chemotherapeutic agents are listed above or are described in U.S. Pat. No. 7,303,749.

The cell-binding agent drug conjugates (e.g., immunoconjugates) of the present invention can be administered in vitro, in vivo and/or ex vivo to treat patients and/or to modulate the growth of selected cell populations including, for example, cancer of the lung, blood, plasma, breast, colon, prostate, kidney, pancreas, brain, bones, ovary, testes, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like. Preferably, the immunoconjugates and chemotherapeutic agents of the invention are administered in vitro, in vivo and/or ex vivo to treat cancer in a patient and/or to modulate the growth of cancer cells, including, for example, cancer of the blood, plasma, lung, breast, colon, prostate, kidney, pancreas, brain, bones, ovary, testes, and lymphatic organs; more preferably lung, colon prostrate, plasma, blood or colon cancer.

"Modulating the growth of selected cell populations" includes inhibiting the proliferation of selected cell populations (e.g., multiple myeloma cell populations, such as MOLP-8 cells, OPM2 cells, H929 cells, and the like) from dividing to produce more cells; reducing the rate of increase in cell division as compared, for example, to untreated cells; killing selected cell populations; and/or preventing selected cell populations (such as cancer cells) from metastasizing. The growth of selected cell populations can be modulated in vitro, in vivo or ex vivo.

In the methods of the present invention, the cell-binding agent drug conjugates (e.g., immunoconjugates) can be administered in vitro, in vivo, or ex vivo. The cell-binding agent drug conjugates (e.g., immunoconjugates) can be used with suitable pharmaceutically acceptable carriers, diluents, and/or excipients, which are well known, and can be determined, by one of skill in the art as the clinical situation warrants. Examples of suitable carriers, diluents and/or excipients include: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The compounds and compositions described herein may be administered in appropriate form, preferably parenterally, more preferably intravenously. For parenteral administration, the compounds or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

The compositions can also be in the form of sterile solid compositions that can be dissolved or dispersed in sterile water or any other injectable sterile medium.

The "therapeutically effective amount" of the cell-binding agent drug conjugate (e.g., immunoconjugates) described herein refers to the dosage regimen for modulating the growth of selected cell populations and/or treating a patient's disease, and is selected in accordance with a variety of factors, including the age, weight, sex, diet and medical condition of the patient, the severity of the disease, the route of administration, and pharmacological considerations, such as the activity, efficacy, pharmacokinetic and toxicology profiles of the particular compound used. The "therapeutically effective amount" can also be determined by reference to standard medical texts, such as the Physicians Desk Reference 2004. The patient is preferably an animal, more preferably a mammal, most preferably a human. The patient can be male or female, and can be an infant, child or adult.

Examples of suitable protocols of cell-binding agent drug conjugates (e.g., immunoconjugate) administration are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period. Dosages will be about 10 pg to about 1000 mg/kg per person, i.v. (range of about 100 ng to about 100 mg/kg).

About one to about four weeks after treatment, the patient can receive a second course of treatment. Specific clinical protocols with regard to route of administration, excipients, diluents, dosages, and times can be determined by the skilled artisan as the clinical situation warrants.

The present invention also provides pharmaceutical kits comprising one or more containers filled with one or more of the ingredients of the pharmaceutical compounds and/or compositions of the present invention, including, one or more immunoconjugates and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

The compounds and conjugates (e.g., immunoconjugates) could also be used for the manufacture of a medicament useful for treating or lessening the severity of disorders, such as, characterized by abnormal growth of cells (e.g., cancer).

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic agents and conjugates that are therapeutically effective will depend on the particular cancer being treated, the extent of the disease and other factors familiar to the physician of skill in the art and can be determined by the physician. For example, the 2006 edition of the Physician's Desk Reference discloses that Taxotere (see p. 2947) is an inhibitor of tubulin depolymerization; Doxorubicin (see p 786), Doxil (see p 3302) and oxaliplatin (see p 2908) are DNA interacting agents, Irinotecal (see p. 2602) is a Topoisomerase I inhibitor, Erbitux (see p 937) and Tarceva (see p 2470) interact with the epidermal growth factor receptor. The contents of the PDR are expressly incorporated herein in their entirety by reference. One of skill in the art can review the PDR, using one or more of the following parameters, to determine dosing regimens and dosages of the chemotherapeutic agents and conjugates, which can be used in accordance with the teachings of this invention. These parameters include:

1. Comprehensive Index
   a) by Manufacturer
   b) Products (by company's or trademarked drug name)
   c) Category index (for example, "antihistamines", "DNA alkylating agents" taxanes etc.)
   d) Generic/chemical index (non-trademark common drug names)
2. Color Images of Medications
3. Product Information, Consistent with FDA Labeling
   a) Chemical information
   b) Function/action
   c) Indications & Contraindications
   d) Trial research, side effects, warnings All references cited herein and in the examples that follow are expressly incorporated by reference in their entireties.

EXAMPLES

The invention will now be described by reference to non-limiting examples. Unless otherwise specified, all percents and ratios are by volume.

Example 1

Materials and Methods

Methyl 2-(acetylthio)-4-bromobutanoate

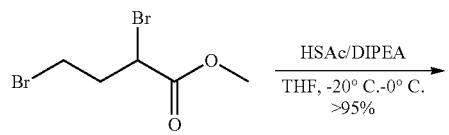

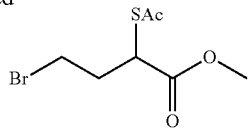

10.0 g (38.4 mmol) of methyl 2,4-dibromobutanoate in 100 ml of dry THF at 20° C. was added drop wise the mixture of 2.75 ml (38.5 mmol) of thiolacetic acid in 8.5 ml (48.9 mmol) of DIPEA and 50 ml of dry THF in 1.5 hour. After stirring overnight at −20° C. then 0° C. for 2 hours under Ar, the mixture was concentrated, diluted with EtAc/Hexane, washed with 1.0 M $NaH_2PO_4$, dried over $MgSO_4$, filtered, evaporated, and $SiO_2$ chromatographic purification (1:12 to 1:10 EtAc/Hexane) to afford 9.5 g (96%) of the title compound. 1H NMR ($CDCl_3$) 4.38 (1H, t, J=7.1 Hz), 3.74 (s, 3H), 3.40 (m, 2H), 2.57~2.47 (m, 1H), 2.37 (s, 3H), 2.36~2.21 (m, 1H); $^{13}$C NMR 193.24, 171.36, 53.15, 44.45, 34.67, 30.46, 29.46; MS m/z+ 276.9 (M+Na), 278.9 (M+2+Na)

4-Bromo-1-methoxy-1-oxobutane-2-sulfonic acid

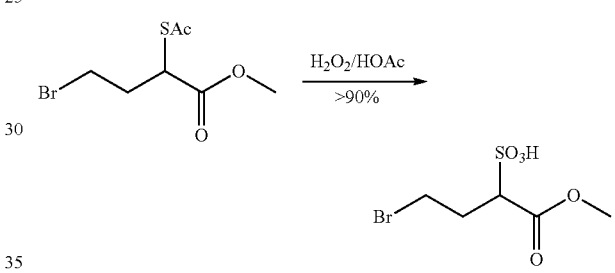

9.2 g (36.3 mmol) of methyl 2-(acetylthio)-4-bromobutanoate in 80 ml of acetic acid was added 40 ml of hydrogen peroxide (35% in water). The mixture was stirred overnight, then evaporated, diluted with water, neutralized with $NaHCO_3$, washed with 1:1 Hexane/EtAc. The aqueous solution was evaporated, dissolved in methanol, concentrated, and crystallized with methanol/toluene to afford 8.6 g (90% yield) of the title compound. m.p.=288~293 (decomp); $^1$H NMR (D2O) 4.12 (dd, 1H, J=4.8, 9.3 Hz), 3.83 (s, 3H), 3.64 (m, 1H), 3.53 (m, 1H), 2.54 (m, 2H); $^{13}$C NMR 172.16, 66.73, 55.66, 33.39, 32.70; MS m/z− 260.8 (M−1).

4-(Acetylthio)-1-methoxy-1-oxobutane-2-sulfonic acid

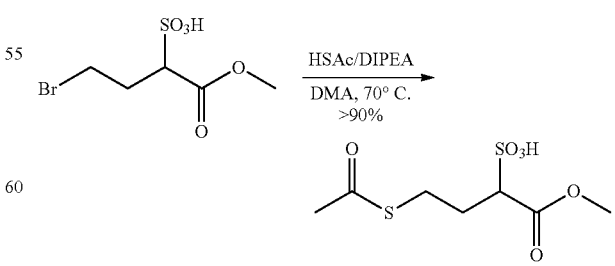

5.0 g (19.2 mmol) of 4-bromo-1-methoxy-1-oxobutane-2-sulfonic acid in 100 ml of THF was added 3.0 ml of thioacetic acid and 9.0 ml of DIPEA in 100 ml of THF. The mixture was stirred overnight then refluxed at 70° C. for 1 hr, evaporated and co-evaporated with 3×100 ml of water after being neutralized to pH 7 with NaHCO₃. The mixture was redissolved in methanol, filtered through celite, concentrated and purified with SiO₂ chromatography eluted with CH₃OH/CH₂Cl₂/ HCOOH 37.5:250:1 to 50:250:1) to afford 4.4 g (90% yield) of the title compound. ¹H NMR (D2O) 3.95 (dd, 1H, J=4.1, 10.3 Hz), 3.83 (s, 3H), 3.74 (m, 2H), 3.22 (dd, 2H, J=7.4, 14.9 Hz), 2.39 (s, 3H); 13C NMR 203.88, 172.91, 67.32, 56.17, 29.04, 20.61; MS m/z– 254.8 (M–H)

4-((5-nitropyridin-2-yl)disulfanyl)-2-sulfobutanoic acid

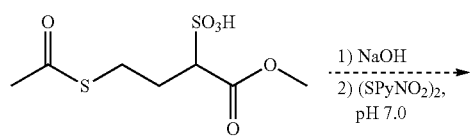

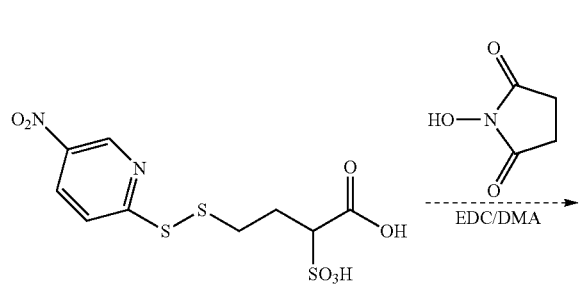

3.0 g (11.7 mmol) of 4-(Acetylthio)-1-methoxy-1-oxobutane-2-sulfonic acid in 100 ml of water was added 50 ml of 3 M NaOH. After being stirred under Ar for 3 h, the mixture was neutralized with 1 M H₂PO₄ to pH 7.2 under Ar. The mixture was added dropwise to the solution of 10.0 g (32.2 mmol) of 1,2-bis(5-nitropyridin-2-yl)disulfane in 200 ml of DMA. After being stirred for 4 h under Ar, the mixture was concentrated, diluted with water, filtered, evaporated and purified with C-18 4.0×20 cm column eluted with water/methanol (95:5) to afford 3.1 g (75% yield) of the title compound. m.p.=288~291° C. (decomp.) 1H NMR (DMF-d7) 9.29 (d, 1H, J=2.2 Hz), 8.63 (dd, 1H, J=2.7, 8.9 Hz), 8.17 (d, 1H, J=8.9 Hz), 3.73 (t, 1H, J=7.2 Hz), 3.22~3.17 (m, 1H), 3.15~3.10 (m, 1H), 2.41~2.33 (m, 2H); ¹³C NMR 170.92, 169.10, 146.04, 143.67, 133.65, 120.72, 64.22, 37.82, 29.26; MS m/z– 352.8 (M–H).

1-(2,5-dioxopyrrolidin-1-yloxy)-4-(5-nitropyridin-2-yl)disulfanyl)-1-oxobutane-2-sulfonic acid

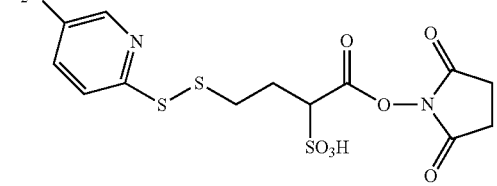

220 mg (0.62 mmol) of 4-((5-nitropyridin-2-yl)disulfanyl)-2-sulfobutanoic acid in 15 DMA was added 130 mg (1.13 mmol) of NHS and 480 mg (2.50 mmol) of EDC. The mixture was stirred under Ar overnight, evaporated and purified on SiO₂ chromatography eluted with CH₂CH₂/CH₃OH/ HCOOH (10000:1000:1 to 10000:1500:1) to afford 227 mg (82% yield) of the title compound. 1H NMR (DMSO-d6) 9.25 (d, 1H, J=5.2 Hz), 8.57 (dd, 1H, J=2.5, 8.9 Hz), 8.04 (t, 1H, J=8.0+8.9 Hz), 3.86 (dd, 1H, J=4.9, 9.7 Hz), 3.13~3.12 (m, 2H), 2.76 (s, 4H), 2.36~2.30 (m, 1H), 2.25~2.21 (m, 1H); 13C NMR 166.96, 165.01, 144.93, 142.26, 132.63, 119.61, 61.00, 35.03, 29.30, 25.39; MS m/z– 449.8 (M–H).

Methyl 2-(acetylthio)-4-bromobutanoate

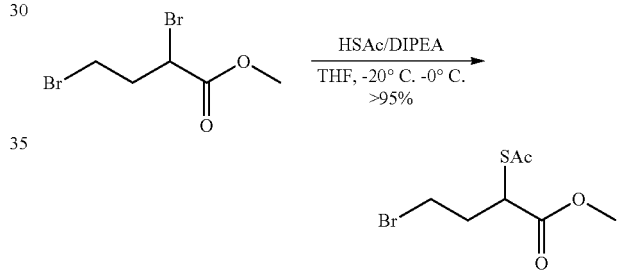

10.0 g (38.4 mmol) of methyl 2,4-dibromobutanoate in 100 ml of dry THF at −20° C. was added dropwise the mixture of 2.75 ml (38.5 mmol) of thiolacetic acid in 8.5 ml (48.9 mmol) of DIPEA and 50 ml of dry THF in 1.5 hour. After stirring overnight at −20° C. then 0° C. for 2 hours under Ar, the mixture was concentrated, diluted with EtAc/Hexane, washed with 1.0 M NaH₂PO₄, dried over MgSO₄, filtered, evaporated, and SiO2 chromatographic purification (1:12 to 1:10 EtAc/Hexane) to afford 9.5 g (96%) of the title compound. 1H NMR (CDCl3) 4.38 (1H, t, J=7.1 Hz), 3.74 (s, 3H), 3.40 (m, 2H), 2.57~2.47 (m, 1H), 2.37 (s, 3H), 2.36~2.21 (m, 1H); 13C NMR 193.24, 171.36, 53.15, 44.45, 34.67, 30.46, 29.46; MS m/z+ 276.9 (M+Na), 278.9 (M+2+Na)

4-Bromo-1-methoxy-1-oxobutane-2-sulfonic acid

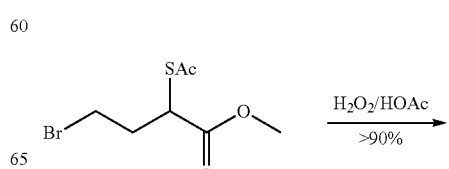

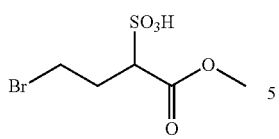

9.2 g (36.3 mmol) of methyl 2-(acetylthio)-4-bromobutanoate in 80 ml of acetic acid was added 40 ml of hydrogen peroxide (35% in water). The mixture was stirred overnight, then evaporated, diluted with water, neutralized with NaHCO$_3$, washed with 1:1 Hexane/EtAc. The aqueous solution was evaporated, dissolved in methanol, concentrated, and crystallized with methanol/toluene to afford 8.6 g (90% yield) of the title compound. m.p.=288~293 (decomp); 1H NMR (D2O) 4.12 (dd, 1H, J=4.8, 9.3 Hz), 3.83 (s, 3H), 3.64 (m, 1H), 3.53 (m, 1H), 2.54 (m, 2H); 13C NMR 172.16, 66.73, 55.66, 33.39, 32.70; MS m/z– 260.8 (M–1).

4-(Acetylthio)-1-methoxy-1-oxobutane-2-sulfonic acid

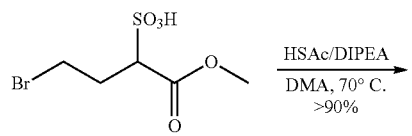

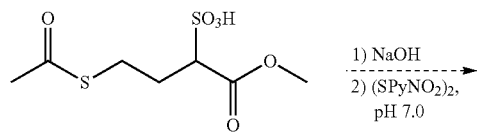

5.0 g (19.2 mmol) of 4-bromo-1-methoxy-1-oxobutane-2-sulfonic acid in 100 ml of THF was added 3.0 ml of thioacetic acid and 9.0 ml of DIPEA in 100 ml of THF. The mixture was stirred overnight then refluxed at 70° C. for 1 hr, evaporated and co-evaporated with 3×100 ml of water after neutralized to pH 7 with NaHCO$_3$. The mixture was redissolved in methanol, filtered through celite, concentrated and purified with SiO$_2$ chromatography eluted with CH$_3$OH/CH$_2$Cl$_2$/HCOOH 37.5:250:1 to 50:250:1) to afford 4.4 g (90% yield) of the title compound. 1H NMR (D2O) 3.95 (dd, 1H, J=4.1, 10.3 Hz), 3.83 (s, 3H), 3.74 (m, 2H), 3.22 (dd, 2H, J=7.4, 14.9 Hz), 2.39 (s, 3H); 13C NMR 203.88, 172.91, 67.32, 56.17, 29.04, 20.61; MS m/z– 254.8 (M–H)

4-((5-nitropyridin-2-yl)disulfanyl)-2-sulfobutanoic acid

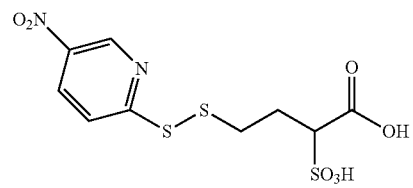

3.0 g (11.7 mmol) of 4-(Acetylthio)-1-methoxy-1-oxobutane-2-sulfonic acid in 100 ml of water was added 50 ml of 3 M NaOH. After stirring under Ar for 3 h, the mixture was neutralized with 1 M H$_2$PO$_4$ to pH 7.2 under Ar. The mixture was added dropwise to the solution of 10.0 g (32.2 mmol) of 1,2-bis(5-nitropyridin-2-yl)disulfane in 200 ml of DMA. After stirring for 4 h under Ar, the mixture was concentrated, diluted with water, filtered, evaporated and purified with C-18 4.0×20 cm column eluted with water/methanol (95:5) to afford 3.1 g (75% yield) of the title compound. m.p.=288~291° C. (decomp.) 1H NMR (DMF-d7) 9.29 (d, 1H, J=2.2 Hz), 8.63 (dd, 1H, J=2.7, 8.9 Hz), 8.17 (d, 1H, J=8.9 Hz), 3.73 (t, 1H, J=7.2 Hz), 3.22~3.17 (m, 1H), 3.15~3.10 (m, 1H), 2.41~2.33 (m, 2H); 13C NMR 170.92, 169.10, 146.04, 143.67, 133.65, 120.72, 64.22, 37.82, 29.26; MS m/z– 352.8 (M–H).

1-(2,5-dioxopyrrolidin-1-yloxy)-4-(5-nitropyridin-2-yl)disulfanyl)-1-oxobutane-2-sulfonic acid

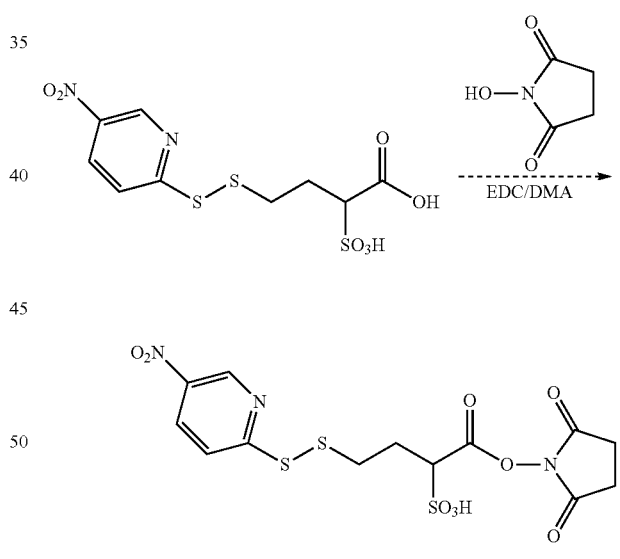

220 mg (0.62 mmol) of 4-((5-nitropyridin-2-yl)disulfanyl)-2-sulfobutanoic acid in 15 DMA was added 130 mg (1.13 mmol) of NHS and 480 mg (2.50 mmol) of EDC. The mixture was stirred under Ar overnight, evaporated and purified on SiO$_2$ chromatography eluted with CH$_2$CH$_2$/CH$_3$OH/ HCOOH (10000:1000:1 to 10000:1500:1) to afford 227 mg (82% yield) of the title compound. 1H NMR (DMSO-d6) 9.25 (d, 1H, J=5.2 Hz), 8.57 (dd, 1H, J=2.5, 8.9 Hz), 8.04 (t, 1H, J=8.0+8.9 Hz), 3.86 (dd, 1H, J=4.9, 9.7 Hz), 3.13~3.12 (m, 2H), 2.76 (s, 4H), 2.36~2.30 (m, 1H), 2.25~2.21 (m, 1H);

13C NMR 166.96, 165.01, 144.93, 142.26, 132.63, 119.61, 61.00, 35.03, 29.30, 25.39; MS m/z– 449.8 (M–H).

4-(pyridin-2-yldisulfanyl)-2-sulfobutanoic acid

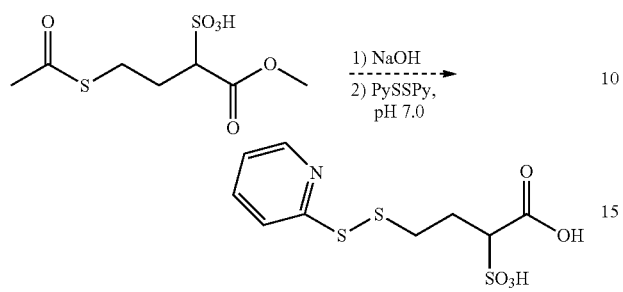

1.5 g (5.85 mmol) of 4-(Acetylthio)-1-methoxy-1-oxobutane-2-sulfonic acid was added to 100 ml of 0.5 M NaOH solution. After stirring under Ar for 3 h, the mixture was concentrated to ~50 ml and neutralized with 1 M $H_2PO_4$ to pH 7.2 under Ar. The mixture was added dropwise to the solution of 4.0 g (18.1 mmol) of 2,2'-dithiodipyridine in 60 ml of DMA. After stirring for 4 h under Ar, the mixture was concentrated, diluted with water, filtered, evaporated and purified with C-18 4.0×20 cm column eluted with water/methanol (99:1 to 90:10) to afford 1.32 g (73% yield) of the title compound. 1H NMR (DMF-d7) 8.39 (dd, 1H, J=3.5, 4.8 Hz), 7.86 (m, 2H), 7.25 (m, 1H), 3.59 (dd, 1H, J=5.2, 9.4 Hz), 2.90 (m, 2H), 2.28 (m, 2H); 13C NMR 172.60, 159.16, 148.93, 138.09, 121.03, 119.38, 67.49, 36.39, 28.666; MS m/z– 307.8 (M–H).

1-(2,5-dioxopyrrolidin-1-yloxy)-1-oxo-4-(pyridin-2-yldisulfanyl)butane-2-sulfonic acid

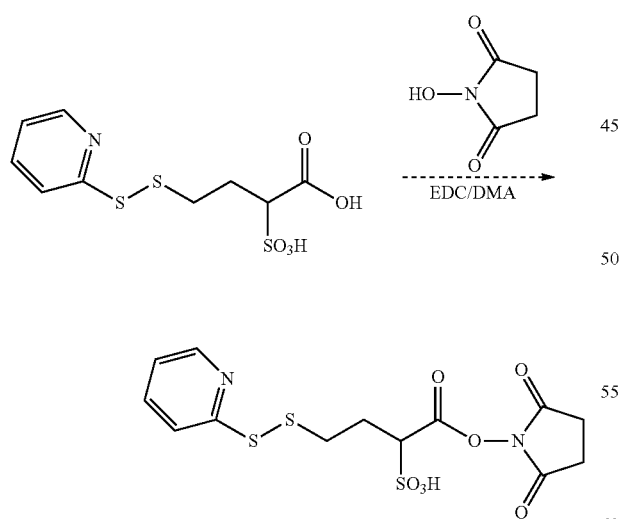

680 mg (2.20 mmol) of 4-(pyridin-2-yldisulfanyl)-2-sulfobutanoic acid in 50 DMA was added 300 mg (2.60 mmol) of NHS and 800 mg (4.16 mmol) of EDC. The mixture was stirred under Ar overnight, evaporated and purified on $SiO_2$ chromatography eluted with $CH_2CH_2/CH_3OH/HCOOH$ (10000:1000:1 to 10000:1500:1) to afford 720 mg (80% yield) of the title compound. 1H NMR (DMSO-d6) 8.40 (dd, 1H, J=3.5, 4.7 Hz), 7.85 (m, 2H), 7.24 (m, 1H), 3.58 (dd, 1H, J=5.1, 9.4 Hz), 2.94~2.90 (m, 2H), 2.74 (s, 4H), 2.31~2.27 (m, 2H); 13C NMR 168.16, 161.11, 147.91, 139.22, 121.63, 119.31, 66.80, 36.30, 28.36, 25.42; MS m/z– 404.9 (M–H).

3,6-endoxo-Δ-tetrahydrophthalhide

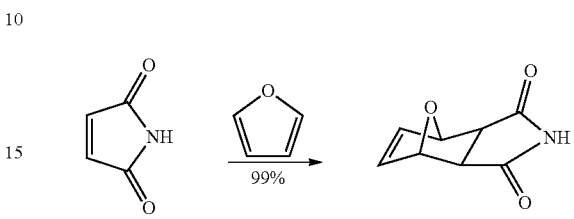

Maleimide (5.0 g, 51.5 mmol) in ethylether (200 ml) was added furan (5.5 ml, 75.6 mmol). The mixture was heated inside a 1 L of autoclave bomb at 100° C. for 8 h. The bomb was cooled down to room temperature, and the inside solid was rinsed with methanol, concentrated and crystallized in ethyl acetate/hexane to afford 8.4 g (99%) of the title compound. 1H NMR (DMF-d7): 11.08 (s, 1H) (NH), 6.60 (m, 2H), 5.16 (m, 2H), 2.95 (m, 2H). 13C NMR 178.84, 137.69, 82.00, 49.92. MS m/z+ 188.4 (MW+Na).

Methyl 4-N-(3,6-endoxo-Δ-tetrahydrophthalido)-2-sulfo-butyrate

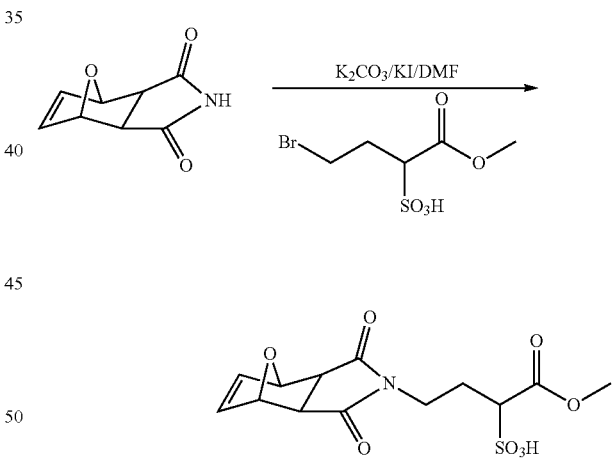

3,6-Endoxo-Δ-tetrahydrophthalhide (0.80 g, 4.85 mmol) in DMA (20 ml) was added $K_2CO_3$ (1.4 g, 10.13 mmol) and KI (0.19 g, 1.14 mmol). After stirring under Ar for 1 hr, methyl 4-bromo-2-sulfo-butyrate (0.98 g, 3.77 mmol) in DMA (10 ml) was added. The mixture was stirred under Ar overnight, evaporated, re-dissolved in 1% HAc in methanol, filtered, evaporated and purified by $SiO_2$ chromatography and eluted with 1:5:0.01 to 1:4:0.01 $CH_3OH/CH_2Cl_2/HAc$ to afford 0.98 (75%) g of the title compound. 1H NMR (DMF-d7): 6.59 (m, 2H), 5.16 (dd, 2H, J=0.8, 7.8 Hz), 3.65-3.63 (m, 3H), 3.47 (m, 2H), 3.01 (s, 3H), 2.83 (m, 2H). 13C NMR 172.94, 162.86, 137.68, 81.98, 52.39, 49.91, 48.58, 36.01, 21.97. MS m/z– 343.9 (MW–H).

Methyl 4-N-maleimido-2-sulfo-butyrate

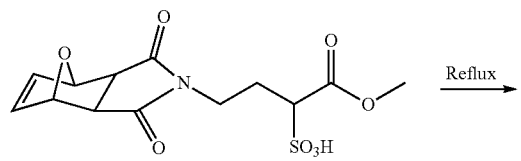

In an opened round bottom flask, methyl 4-N-(3,6-endoxo-Δ-tetrahydrophthalido)-2-sulfo-butyrate (0.30 g, 0.87 mmol) in 20 ml of 1:1 DMA/100 mM NaH$_2$PO$_4$, pH 7.0 was heated at 120~140° C. for 4 h. During the reaction time, 5×10 ml of water was gradually added to keep the reaction volume around 15 ml. The mixture was concentrated to dryness and purified by SiO$_2$ chromatography eluted with 1:5:0.01 to 1:4:0.01 CH$_3$OH/CH$_2$Cl$_2$/HAc to afford 0.230 g (95%) of the title compound. $^1$H NMR (DMF-d7): 6.60 (s, 2H), 4.06 (d, 1H), 3.60 (m, 3H), 3.47 (m, 2H), 2.43 (m, 2H); $^{13}$C NMR 171.59, 164.96, 136.10, 66.20, 51.71, 34.82, 22.10. MS m/z– 276.6 (MW–H).

Methyl 4-azido-2-sulfo-butyrate

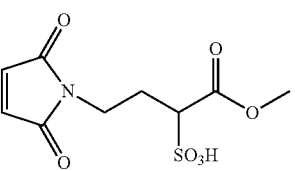

Methyl 4-bromo-2-sulfo-butyrate (1.07 g, 4.11 mmol) and sodium azide (0.70 g (10.7 mmol) in DMF (50 ml) was stirred overnight. The mixture was evaporated and purified by SiO$_2$ chromatography and eluted with 1:5:0.01 CH$_3$OH/CH$_2$Cl$_2$/HAc and crystallized with CH$_3$OH/Toluene/Hexane to afford 1.00 g (95%) of the title compound. m.p=267-272° C. (decomp). 1H NMR (DMF-d7): 12.06 (br, 1H), 3.65 (s, 3H), 3.59 (dd, 1H, J=5.4, 8.9 Hz), 3.47 (m, 2H), 2.24 (m, 2H). $^{13}$C NMR 171.10, 64.29, 52.24, 50.64, 21.35. ESI MS m/z+ 267.9 (M+2Na—H), m/z– 222.0 (M–H). HRMS m/z– (C$_5$H$_9$N$_3$O$_5$S—H) calcd 222.0185. found 222.0179.

4-azido-2-sulfo-butyric acid

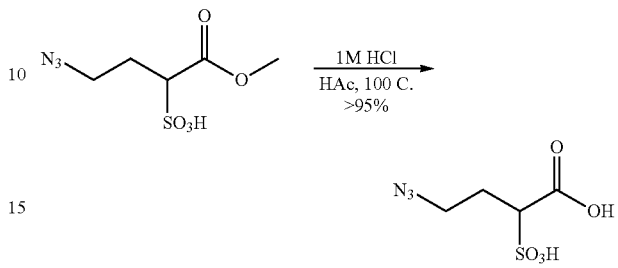

Methyl 4-azido-2-sulfo-butyrate (1.00 g, 4.08 mmol) in the mixture of HCl (50 ml, 1.0 M) and HAC (5 ml) was heated at 100° C. for 8 hrs. The mixture was evaporated and co-evaporated 3×50 ml of water, and crystallized with water/acetone to afford 1.0 g (99%) of the title compound. $^1$H NMR (DMF-d$_7$): 3.60 (m, 2H), 3.52 (m, 1H), 2.24 (m, 2H). $^{13}$C NMR 170.96, 63.04, 50.66, 29.12. ESI MS m/z– 207.7 (MW–H); HRMS m/z– (C$_4$H$_7$N$_3$O$_5$S—H) calcd 208.0028. found 208.0021.

4-Amino-2-sulfo-butyric acid

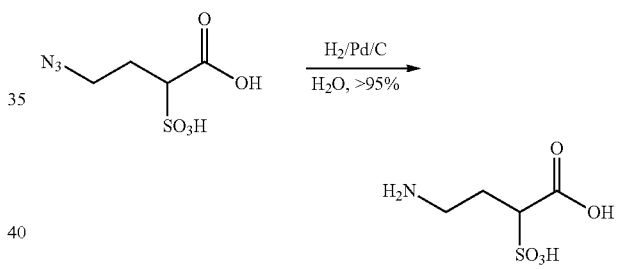

4-Azido-2-sulfo-butyric acid (500 mg, 2.40 mmol), water (20 ml) and Pd/C (110 mg, 10% Pd, 50% water based) were placed into a 250 ml hydrogenation shaking bottle. After the air in the bottle was sucked out by a vacuum, 20 psi of hydrogen was let into the bottle. The mixture was shaken for 8 h, then filtered through celite, washed with DMF, evaporated and co-evaporated with dry DMF to afford 476 mg (91% HCl salt) of the title product. ESI MS m/z– 181.8 (MW–H). This product was used directly without further purification.

(Z)-4-(3-carboxy-3-sulfopropylamino)-4-oxobut-2-enoic acid

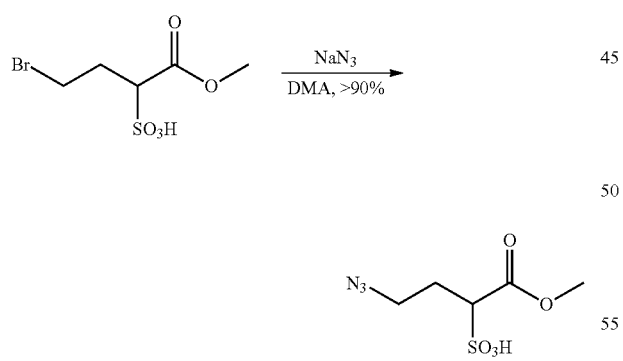

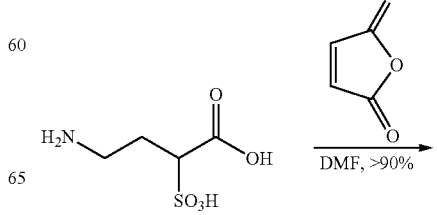

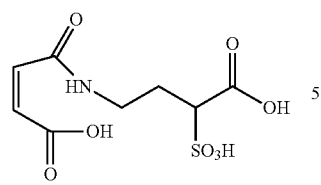

The above 4-Amino-2-sulfo-butyric acid, HCl salt (476 mg, 2.16 mmol) in dry DMF (20 ml) was added maleic anhydride (232 mg, 2.36 mmol). The mixture was stirred under Ar overnight, evaporated and purified on self packed c-18, φ1.0×25 cm column, eluted with water. The fractions contained product were pooled, evaporated and crystallized with H$_2$O/acetone to afford 552 mg (91%) of the title product. $^1$H NMR (DMF-d7): 9.70 (br, 1H), 6.73 (d, 1H, J=12.8 Hz), 6.32 (d, 1H, J=12.8 Hz), 3.69 (m, 1H), 3.47 (m, 2H), 2.27 (m, 2H). $^{13}$C NMR 171.47, 167.32, 165.87, 135.44, 133.07, 63.82, 39.13, 27.62. ESI MS m/z– 279.8 (MW–H); HRMS m/z– (C$_8$H$_{11}$NO$_8$S—H) calcd 280.0127. found 280.0121.

4-N-Maleimido-2-sulfo-butanoic acid

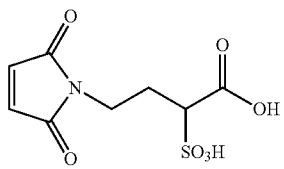

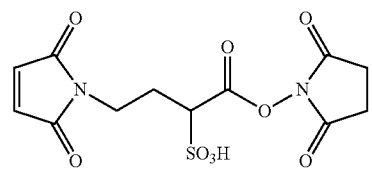

(Z)-4-(3-carboxy-3-sulfopropylamino)-4-oxobut-2-enoic acid (310 mg, 1.10 mmol) in mixture dry DMA (5 ml) and dry toluene (20 ml) was heated. After the temperature reached at 80° C., HMDS (hexamethyldisilazane) (1.40 ml, 6.71 mmol) and ZnCl$_2$ (1.85 ml, 1.0 M in diethyl ether, 1.85 mmol) was added. The mixture was continued heated to 115~125° C. and toluene was collected through Dean-Stark trap. The reaction mixture was fluxed at 120° C. for 6 h. During this period, 2×20 ml of dry toluene was added to keep the mixture volume around 8~10 ml. Then the mixture was cooled, 1 ml of 1:10 HCl (conc)/CH$_3$OH was added, evaporated, purified on SiO$_2$ chromatography eluted with CH$_3$OH/CH$_2$Cl$_2$/HAc (1:5:0.01 to 1:4:0.01) to afford 260 mg (92%) of the title product. $^1$H NMR (DMF-d$_7$): 10.83 (br, 1H), 6.95 (s, 2H), 1H, J=12.8 Hz), 3.65 (m, 1H), 3.54 (m, 2H), 2.27 (m, 2H). $^{13}$C NMR 173.61, 172.04, 135.47, 64.18, 37.1, 27.89. ESI MS m/z– 261.8 (MW–H). HRMS m/z– (C$_8$H$_9$NO$_7$S—H) calcd 262.0021. found 262.0027.

Succinimidyl 4-N-maleimido-2-sulfo-butyrate

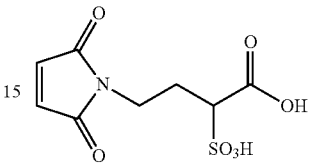 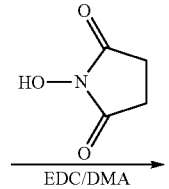

4-N-maleimido-2-sulfo-butanoic acid (260 mg, 0.99 mmol) in DMA (10 ml) was added to NHS (220 mg, 1.91 mmol) and EDC (500 mg, 2.60 mmol). The mixture was stirred under Ar overnight, evaporated and purified on SiO$_2$ chromatography eluted with CH$_2$CH$_2$/CH$_3$OH/HAc (10000:1000:1 to 10000:2000:1), then crystallized with DMA/EtAc/Hexane to afford 285 mg (81% yield) of the title compound. $^1$H NMR (DMF-d7) 6.99 (s, 1H), 3.83 (m, 1H), 3.64 (m, 2H), 2.75 (s, 4H), 2.34 (m, 2H); $^{13}$C NMR 171.97, 171.82, 166.64, 135.58, 62.00, 36.66, 26.62; ESI MS m/z– 358.9 (M–H); HRMS m/z– (C$_{12}$H$_{12}$N$_2$O$_9$S—H) calcd 359.0185. found 359.0178

(E)-Methyl 4-azidobut-2-enoate

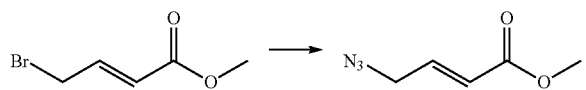

To the solution of NaN$_3$ (2.80 g, 43.01 mmol) in 100 ml of DMF at −20° C. was added methyl 4-bromocrotonate (5.00 ml, 85%, 36.10 mmol). After stirred at −20° C. for 30 min, the mixture was stirred at 0° C. for 4 h, evaporated, suspended with EtAc/Hexane (1:1), filtered, evaporated and chromatographic purification on SiO$_2$ column eluted with EtAc/Hexane (1:25 to 1:10) to afford HRMS for 4.08 g (80%) of the title product. $^1$H NMR (CDCl$_3$) 6.88 (m, 1H), 6.06 (ddd, 1H, J−=1.7, 3.4, 15.6 Hz), 3.97 (dd, 2H, J=1.2, 4.96 Hz), 3.73 (s, 3H); $^{13}$C NMR 166.23, 140.86, 123.49, 51.95, 51.36; ESI MS m/z+ 182.5 (M+Na+H₂O); HRMS m/z+ (C₅H₇N₃O₂+H₂O+Na) calcd 182.0542. found 182.0548.

Methyl 3-(acetylthio)-4-azidobutanoate

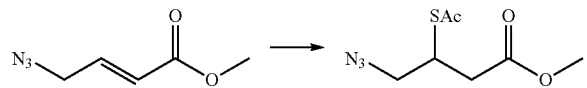

To the solution of (E)-Methyl 4-azidobut-2-enoate (4.00 g, 28.37 mmol) in 60 ml of THF at 0° C. was added the mixture of thioacetic acid (3.0 ml, 42.09 mmol) and DIPEA (8.0 ml, 45.92 mmol) in 60 ml of THF in 20 min. After stirred at 0° C. for 1 hr, the mixture was stirred at RT overnight, evaporated, redissolved in CH₂Cl₂, washed with NaHCO₃ (sat.) and 1 M NaH₂PO₄/NaCl (sat.), pH 4 respectively, dried over MgSO4, filtered, evaporated and chromatographic purification on SiO₂ column eluted with EtAc/Hexane (1:8 to 1:4) to afford HRMS for 4.98 g (81%) of the title product. ¹H NMR (CDCl₃) 3.66 (m, 1H), 3.62 (s, 3H), 3.40 (dd, 1H, J=7.5, 12.7 Hz), 3.31 (m, 1H), 2.78 (m, 1H), 2.60 (m, 1H), 2.32 (s, 3H); ¹³C NMR (DMF-d7) 192.20, 172.48, 56.56, 53.60, 51.31, 34.58, 30.56; ESI MS m/z+240.0 (M+Na), 255.9 (M+K); HRMS m/z+ (C₇H₁₁N₃O₃S+Na) calcd 240.0419. found 240.0415.

Azido-4-methoxy-4-oxobutane-2-sulfonic acid

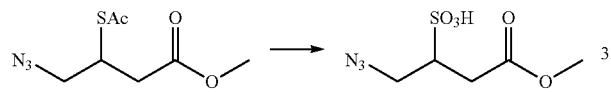

Methyl 3-(acetylthio)-4-azidobutanoate (4.00 g, 18.43 mmol) in 75 ml of acetic acid was added 25 ml of H₂O₂ (30%). The mixture was stirred overnight, evaporated and co-evaporated with EtOH/toluene and purified on SiO₂ chromatography eluted with CH₃OH/CH₂Cl₂/HAc (100:800:1 to 100:500:1) to afford 3.85 (93%) g the title compound. ¹H NMR (CD₃OD) 3.78 (dd, 1H, J=5.0, 12.7 Hz), 3.62 (s, 3H), 3.44 (dd, 1H, J=7.5, 12.7 Hz), 3.33 (m, 1H), 2.84 (dd, 1H, J=5.6, 16.5 Hz), 2.57 (dd, 1H, J=7.5, 16.5 Hz); ¹³C NMR (DMF-d7) 173.37, 57.31, 52.54, 52.49, 34.51; ESI MS m/z– 221.7 (M+H),

4-Azido-3-sulfobutanoic acid

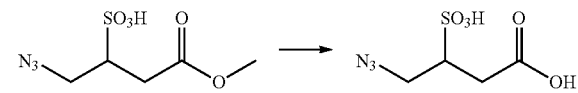

Azido-4-methoxy-4-oxobutane-2-sulfonic acid (3.80 g, 17.04 mmol) in 150 ml of 1.0 M HCl was added 8.0 ml of HAc. The mixture was refluxed at 120° C. overnight, evaporated and co-evaporated with water, EtOH, EtOH/toluene respectively and purified on SiO₂ chromatography eluted with CH₃OH/CH₂Cl₂/HAc (100:500:1 to 100:400:1) to afford 3.02 (85%) g the title compound. ¹H NMR (CD₃OD) 3.77 (dd, 1H, J=5.1, 12.8 Hz), 3.45 (dd, 1H, J=7.0, 12.8 Hz), 3.31 (m, 1H), 2.86 (dd, 1H, J=4.7, 16.7 Hz), 2.51 (dd, 1H, J=8.4, 16.7 Hz); ¹³C NMR (DMF-d7) 173.98, 67.50, 59.78, 27.82; ESI MS m/z– 207.7 (M–H).

4-amino-3-sulfobutanoic acid

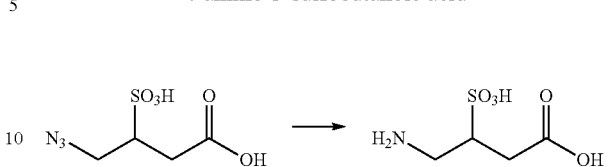

In a 500 ml of hydrogenation bottle was added 4-azido-3-sulfobutanoic acid (3.00 g, 14.35 mmol), 150 ml of methanol and 0.32 g of Pd/C (10% Pd, 50% wet). After sucked out air, 30 psi of H2 was conducted, and the mixture was shaken overnight, filtered through celite, evaporated, and coevaporated with dry EtOH to afford about 2.50 g (95%) of 4-amino-3-sulfobutanoic acid. ¹H NMR (CD₃OD) 3.24 (m, 1H), 3.17 (m, 1H), 2.90 (dd, 1H, J=2.6, 16.5 Hz), 2.33 (dd, 1H, J=10.1, 16.5 Hz), ESI MS m/z– 181.60 (M–H). The resulted compound was unstable and was used directly without further purification.

(Z)-4-(3-carboxy-2-sulfopropylamino)-4-oxobut-2-enoic acid

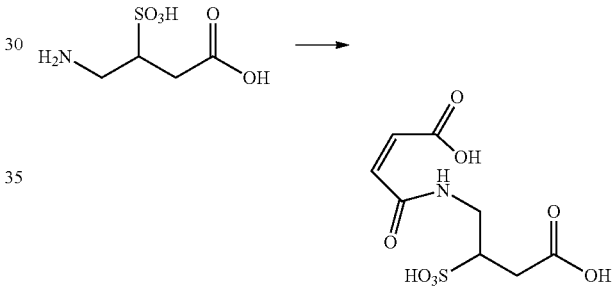

To the solution of 4-amino-3-sulfobutanoic acid (~2.50 g, 13.66 mmol) in 100 ml of DMA was added maleic anhydride (1.48 g, 15.10 mmol) and the mixture was stirred over night, evaporated, purified on C-18 column (2×30 cm) eluted with 1% HAc in water and crystallized with MeOH/Acetone/toluene to afford 3.34 g (83%) of (Z)-4-(3-carboxy-2-sulfopropylamino)-4-oxobut-2-enoic acid. ¹H NMR (CD₃OD) 6.33 (d, 1H, J=12.6 Hz), 6.10 (d, 1H, J=12.6 Hz), 3.64 (dd, 1H, J=5.8, 14.0 Hz), 3.54 (m, 1H), 3.30 (m, 1H), 2.78 (dd, 1H, J=4.9, 16.8 Hz), 2.39 (m, 1H); ¹³C NMR 173.52, 168.68, 167.98, 135.59, 127.79, 57.31, 40.56, 34.52; ESI MS m/z– 279.7 (M–H).

4-(2,5-dioxo-2,5-dihydro-1H-pyrrol-1-yl)-3-sulfobutanoic acid

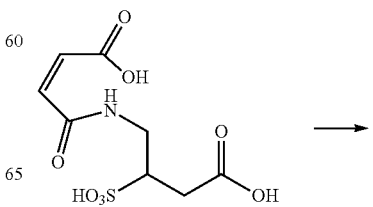

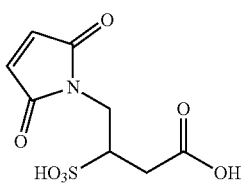

(Z)-4-(3-carboxy-2-sulfopropylamino)-4-oxobut-2-enoic acid (450 mg, 1.60 mmol) in mixture of 10 ml of dry DMA and 50 ml of dry toluene was heated. After the temperature reached at 80° C., HMDS (hexamethyldisilazane, 1.80 ml, 8.63 mmol,) and ZnCl$_2$ (3.2 ml, 1.0 M in diethyl ether) were added. The mixture was continued heated to 115~125° C. and toluene was collected through Dean-Stark trap. The reaction mixture was fluxed at 120° C. for 6 h. During this period, 2×20 ml of dry toluene was added to keep the mixture volume around 8~10 ml. Then the mixture was cooled, 1 ml of 1:10 HCl (conc)/CH$_3$OH was added, evaporated, purified on SiO$_2$ chromatography eluted with 1:5:0.01 CH$_3$OH/CH$_2$Cl$_2$/HAc to afford 315 mg (75%) of the title product. $^1$H NMR (DMF-d7) 6.96 (s, 2H), 4.04 (dd, 1H, J=4.3, 13.8 Hz), 3.47 (m, 1H), 3.23 (dd, 1H, J=7.4, 14.7 Hz), 2.99 (dd, 1H, J=3.3, 16.8 Hz), 2.35 (dd, 1H, J=8.1, 16.9 Hz); $^{13}$C NMR 173.58, 172.18, 135.54, 54.61, 40.24, 32.43, ESI MS m/z– 261.70 (M–H).

1-(2,5-Dioxo-2,5-dihydro-1H-pyrrol-1-yl)-4-(2,5-dioxopyrrolidin-1-yloxy)-4-oxobutane-2-sulfonic acid

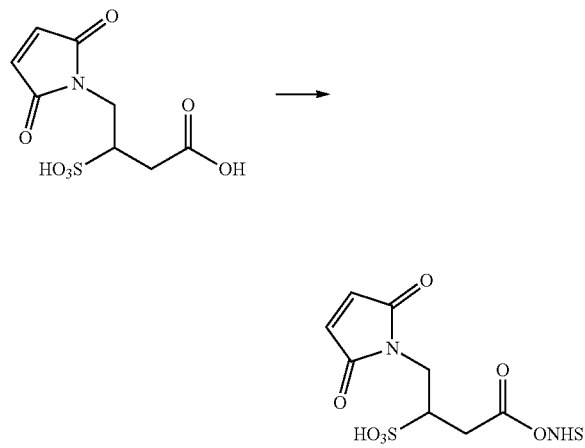

4-(2,5-Dioxo-2,5-dihydro-1H-pyrrol-1-yl)-3-sulfobutanoic acid (110 mg, 0.418 mmol), EDC (240 mg, 1.25 mmol) and N-hydroxysuccinimide (58 mg, 0.504 mmol) was stirred in 10 ml of DMA for overnight, evaporated and purified on SiO$_2$ chromatography eluted with CH$_3$OH/CH$_2$Cl$_2$/HAc (100:900:1 to 100:600:1) to afford 112 mg (75%) of the title product. $^1$H NMR (DMF-d7) 6.93 (s, 2H), 4.06 (dd, 1H, J=4.8, 13.1 Hz), 3.80 (dd, 1H, J=10.7, 13.9 Hz), 3.35 (dd, 1H J=3.3, 17.8 Hz), 3.25 (m, 1H), 3.10 (dd, 1H, J=2.2, 16.4 Hz), 2.87 (m, 4H); $^{13}$C NMR 172.27, 170.88, 169.29, 135.55, 55.28, 40.22, 32.69, 26.66; ESI MS m/z– 261.70 (M–H).

Ethyl 3-(acetylthio)-3-cyanopropanoate

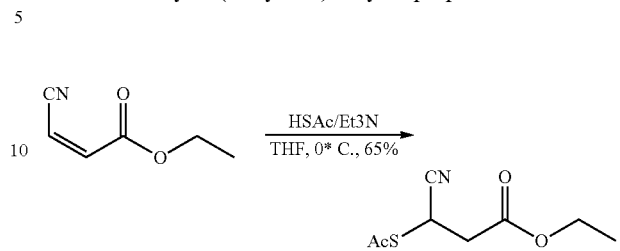

(Z)-ethyl 3-cyanoacrylate (5.01 g, 40.00 mmol) in 80 ml of THF at –20° C. was added the solution of thiol acetic acid (5.0 ml, 70.15 mmol) and DIPEA (16.0 ml, 92.03 mmol) in 20 ml of THF in 30 min. The reaction was kept at –20° C. for 4 hr then room temperature overnight. The mixture was concentrated, diluted with CH$_2$Cl$_2$, washed with saturated NaHCO$_3$, dried over MgSO$_4$, filtered, evaporated and purified by SiO$_2$ chromatography (1:4 EtAC/Hexane) to afford 5.22 g (65%) of the title compound. Rf=0.25 (1:4 EtAC/Hexane); $^1$H NMR (CDCl$_3$), 4.44 (m, 1H), 4.11 (dd, 2H, J=7.1, 14.3 Hz), 3.38 (m, 1H), 3.15 (m, 1H), 2.17 (s, 3H), 1.19 (t, 3H, J=7.2 Hz); $^{13}$C NMR 194.12, 173.21, 119.82, 61.35, 33.52, 30.08, 14.62; MS m/z+ 225.9 (MW+Na), m/z– 201.7 (MW–H).

Cyano-3-ethoxy-3-oxopropane-1-sulfonic acid

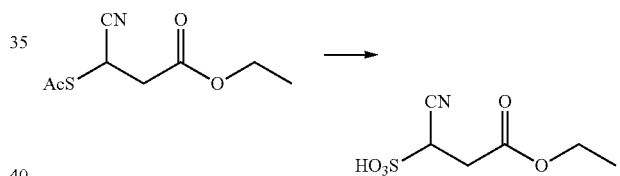

Ethyl 3-(acetylthio)-3-cyanopropanoate (2.00 g, 9.95 mmol) in acetic acid (40 ml) was added H$_2$O$_2$ (12 ml, 30%). The mixture was stirred overnight, evaporated and purified on silica gel chromatography eluted with methanol/dichloromethane/acetic acid (1:8:0.01 to 1:5:0.01) to afford 1.72 g (84%) of the title compound. $^1$H NMR (DMSO), 4.63 (m, 1H), 4.12 (dd, 2H, J=7.1, 14.3 Hz), 3.27 (m, 1H), 3.05 (m, 1H), 1.28 (t, 3H, J=7.2 Hz); $^{13}$C NMR 173.15, 113.85, 61.38, 48.32, 26.33, 14.15; MS m/z– 205.7 (MW–H).

1-(tert-Butoxycarbonylamino)-4-ethoxy-4-oxobutane-2-sulfonic acid

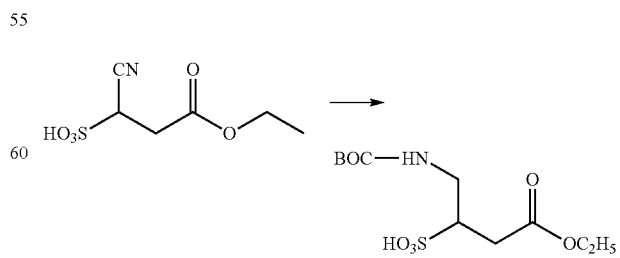

In a hydrogenation bottle was added Cyano-3-ethoxy-3-oxopropane-1-sulfonic acid (2.50 g, 12.06 mmol), ethanol (80 ml), fresh filtered Raney Nickel (0.40 g) and BOC anhydride (3.30 g, 15.12 mmol). After the air inside the bottle was sucked out by vacuum, 20 psi of hydrogen was conducted to the bottle. The bottle was shaken over night, filtered through celite, evaporated, and purified on silica gel chromatography eluted with methanol/dichloromethane/acetic acid (1:6:0.01) to afford 3.18 g (85%) of the title compound. $^1$H NMR (DMSO), 6.82 (s, 1H), 4.26 (m, 1H), 4.11 (dd, 2H, J=7.1, 14.3 Hz), 3.53 (dd, 1H, J=4.2, 13.4 Hz), 3.36 (m, 1H), 2.86 (m, 1H), 2.51 (m, 1H), 1.38 (s, 9H), 1.22 (t, 3H, J=7.2 Hz); $^{13}$C NMR 173.35, 155.72, 80.44, 62.05, 52.55, 41.61, 34.50, 28.85, 14.52; MS m/z– 309.8 (MW–H).

4-(tert-butoxycarbonylamino)-3-sulfobutanoic acid

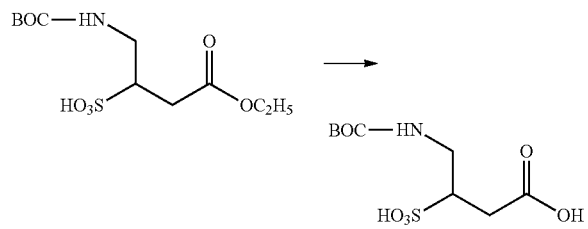

1-(tert-Butoxycarbonylamino)-4-ethoxy-4-oxobutane-2-sulfonic acid (402 mg, 1.29 mmol) in the mixture of THF/H$_2$O (1:2, 60 ml) was added lithium hydroxide monohydrate (2.0 g, 47.6 mmol). The mixture was stirred under Ar overnight, concentrated, purified on C-18 column (2×30 cm) eluted with from 100% water to 10% methanol in water to afford 328 mg (90%) of the title compound. $^1$H NMR (DMSO), 6.78 (s, 1H), 4.03 (m, 1H), 3.57 (dd, 1H, J=4.2, 13.4 Hz), 3.41 (m, 1H), 2.89 (m, 1H), 2.61 (m, 1H), 1.39 (s, 9H); $^{13}$C NMR 174.21, 155.82, 79.85, 59.95, 42.06, 32.52, 28.88, 14.55; ESI MS 281.8 (M–H);

(Z)-4-(3-carboxy-2-sulfopropylamino)-4-oxobut-2-enoic acid

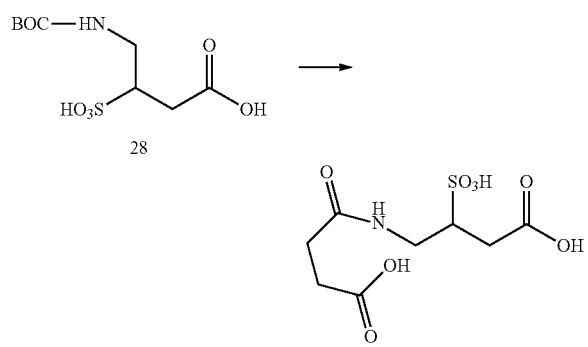

4-(Tert-butoxycarbonylamino)-3-sulfobutanoic acid (321 mg, 1.13 mmol) was stirred in the mixture of HCl (conc)/Dioxane (1:4, 15 ml) for 30 min, evaporated and coevaporated with EtOH/Toluene (1:1, 4×20 ml) to dryness. To the dryness material was added maleic anhydride (121 mg, 1.23 mmol) and DMA (20 ml) and the mixture was stirred overnight, evaporated and run through C-18 column eluted with water and crystallized with EtOH/Hexane to afford 263 mg (83%) of the title compound. ESI MS 279.8 (M–H). The NMR data are the same through the route with 4-azido-3-sulfobutanoic acid.

N,N,N-trimethyl-2-oxotetrahydrothiophen-3-aminium

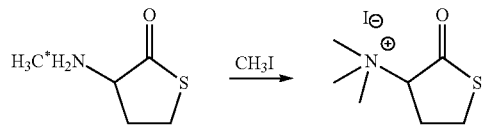

3-aminodihydrothiophen-2(3H)-one hydrochloride (6.00 g, 39.1 mmol), sodium bicarbonate (3.28 g, 39.1 mmol) and iodomethane (13 mL, 209 mmol) were stirred in dry methanol (100 ml) overnight, filtered through celite, evaporated, purified on SiO2 column eluted with MeOH/CH$_2$Cl$_2$/HAc (1:5:0.01), and crystallized with EtOH/Hexane to afford 5.25 g (84%) of the title product. mp 228-231° C. $^1$H NMR (CD$_3$OD) 4.27 (m, 1H), 3.25 (s, 9H), 2.56-2.47 (m, 2H), 2.34 (m, 1H), 2.26 (m, 1H); $^{13}$C NMR 168.97, 75.06, 53.25, 30.85, 16.46; ESI MS m/z+ 160.0 (M+).

1-carboxy-N,N,N-trimethyl-3-(pyridin-2-yldisulfanyl)propan-1-aminium

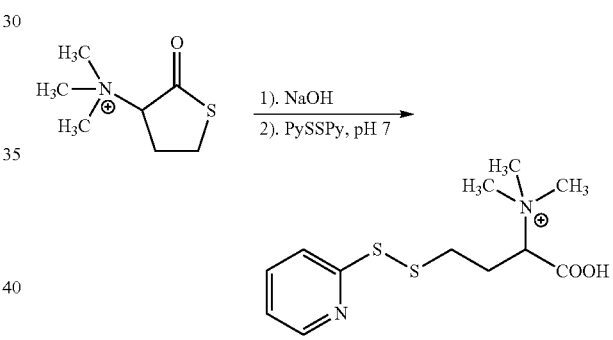

N,N,N-trimethyl-2-oxotetrahydrothiophen-3-aminium acetate (2 g, 9.13 mmol) was stirred in 75 ml of 1 M NaOH (3 g NaOH in 75 ml H$_2$O) for 45 min. neutralized with 4 M H$_3$PO$_4$ to pH 7.4, concentrated, added to 1,2-di(pyridin-2-yl)disulfane (11 g, 49.9 mmol) in 200 ml of MeOH. The mixture was stirred over night, extracted with EtAc. The aqueous solution was evaporated, suspended with MeOH, filtered salt, evaporated and purified on C-18 column (2 cm×30 cm) eluted with water/methanol (100 water to 20% methanol/water) to afford 2.6 g (75%) of the title product. ESI MS m/z+ 309.1 (M+Na—H).

1. Modification of Antibody with Sulfo Linker

The huC242 is modified with sulfo linker at 8 mg/mL antibody, a 15 fold molar excess of sulfo linker (~30 mM stock solution in DMA). The reaction is carried out in 100 mM NaPi, pH8.0 buffer with DMA (5% v/v) for 15, 30, 120, and 200 minutes at 25° C. The modified huC242 was purified by G25 column with 50 mM NaPi, 50 mM NaCl, and 2 mM EDTA, pH6.5 to remove the excess sulfo linker.

2. Measurement of Releasable Spy-NO$_2$ and Antibody Concentration of Modified huC242

The assay and spectral measurement were carried in 100 mM NaPi, pH7.5 at room temperature. The molar ratio of Spy-NO$_2$ released per mole of huC242 antibody was calculated by measuring the $A_{280}$ of the sample and then the increase in the $A_{394}$ of the sample after adding DTT (50 µL of 1 M DTT/mL of sample). The concentration of DTT-released 2-mercaptopyridine is calculated using a $\epsilon_{394\ nm}$ of 14,205 $M^{-1}\ cm^{-1}$. The concentration of antibody can then be calculated using a $\epsilon_{280\ nm}$ of 217,560 $M^{-1}\ cm^{-1}$ after subtracting the contribution of Spy-$NO_2$ absorbance at 280 nm ($A_{394\ nm}$ post DTT×3344/14205) from the total $A_{280\ nm}$ measured before DTT addition. The molar ratio of Spy-$NO_2$:Ab can then be calculated. The mg/mL (g/L) concentration of huC242 is calculated using a molecular weight of 147,000 g/mole.

3. Conjugation Reaction

The modified huC242 was reacted with a 1.7-fold molar excess of DM4 (based on DM4 stock SH concentration) over Spy-$NO_2$. The reaction is carried out at 2.5 mg/mL antibody in 50 mM NaPi, 50 mM NaCl, 2 mM EDTA, pH6.5 and DMA (5% v/v). After addition of DM4, the reaction was incubated 25° C. for ~20 hours. The final conjugate was purified by G25 column with 10 mM Histidine, 130 mM Glycine, 5% sucrose, pH5.5 to remove the excess DM4 drug.

4. Calculation of huC242 and DM4 Concentration

The huC242 and DM4 both absorb at the two wavelengths used to measure each component separately, i.e., 280 and 252 nm. The extinction coefficient at 280 nm for huC242 is 217,560 and for DM4 is 5180 $M^{-1}$. The 252 nm/280 nm absorbance ratios of huC242 and DM4 are 0.368 and 5.05 respectively. The concentrations were calculated with following equation $$C_D = \frac{A_{252} - 0.368 A_{280}}{24692.4}$$

$$C_{Ab} = \frac{A_{280} - 5180 C_D}{217,560}$$

Results

| Modification time | L/A | D/A | Monomer ratio | Free drug % |
|---|---|---|---|---|
| 15 min | 5.0 | 4.1 | 96.7% | N/D* |
| 30 min | 6.1 | 5.4 | 96.2% | <1% |
| 120 min | 6.6 | 6.8 | 95.7% | <1% |
| 200 min | 6.6 | 6.3 | 95.9% | <1% |

C242-Sulfo-DM4 Linker Titration

| Linker Excess | L:A | DM4 xs | D:A | mg/mL Ab | µg/mL DM4 | % Monomer | % Free Drug |
|---|---|---|---|---|---|---|---|
| 5 | 2.4 | 1.7 | 1.9 | 0.83 | 8.2 | 95 | 0 |
| 10 | 4.1 | 1.7 | 3.3 | 0.83 | 14.4 | 94 | 0 |
| 15 | 5.6 | 1.7 | 4.6 | 0.82 | 20.0 | 93 | 0 |
| 20 | 7.3 | 1.7 | 6.0 | 0.82 | 25.8 | 91 | 0 |
| 25 | 9.1 | 1.3 | 6.6 | 0.79 | 27.7 | 92 | 0.6 |
| 30 | 10.4 | 1.3 | 7.6 | 0.68 | 27.5 | 94 | 1.1 |
| 35 | 12.2 | 1.3 | 8.2 | 0.67 | 26.7 | 95 | 1.6 |

Conjugation Protocol:

Modification was done at pH 8.0, buffer A and 5% DMA for 90 min at room temperature, the antibody concentration is 7 mg/ml. The modified antibody was purified by NAP column using Buffer A pH6.5. The conjugation was down at Buffer A, pH6.5 with 5-10% DMA at room temperature overnight. The drug to linker ratio ranged from 1.3 to 1.7 deepening on the total drug added.

Example 2

Conjugate Synthesis

SPP or SSNPP linker was dissolved in ethanol at a concentration of approximately 10 mM. Antibody was dialyzed into buffer A (50 mM KPi, 50 mM NaCl, 2 mM EDTA, pH 6.5). For the linker reaction, the antibody was at 8 mg/ml, and 7 equivalents of linker were added while stirring in the presence of 5% (v/v) ethanol. The reaction was allowed to proceed at ambient temperature for 90 minutes. Unreacted linker was removed from the antibody by Sephadex G25 gel filtration using a Sephadex G25 column equilibrated with Buffer A at pH 6.5 or 150 mM potassium phosphate buffer containing 100 mM NaCl, pH 7.4 as indicated. For the SPP linker, the extent of modification was assessed by release of pyridine-2-thione using 50 mM DTT and measuring the absorbance at 343 nm as described below ($\epsilon 343 = 8080\ M^{-1}\ cm^{-1}$ for free pyridine-2-thione). For SSNPP, modification was assessed directly by measuring the absorbance at 325 nm ($\epsilon_{325} = 10,964\ M^{-1}\ cm^{-1}$ for the 4-nitropyridyl-2-dithio group linked to antibody). For the conjugation reaction, thiol-containing drug (either DM1 or DC4) was dissolved in DMA (N,N-dimethylacetamide) at a concentration of approximately 10 mM. The drug (0.8-1.7-fold molar excess relative to the number of linker molecules per antibody as indicated) was slowly added with stirring to the antibody which was at a concentration of 2.5 mg/ml in buffer A (pH 6.5 or pH 7.4) in a final concentration of 3% (v/v) DMA. The reaction was allowed to proceed at ambient temperature for the indicated times. Drug-conjugated antibody was purified using a Sephadex G25 column equilibrated with buffer B (PBS, pH 6.5). For DML, the extent of drug conjugation to antibody was assessed by measuring $A_{252}$ and $A_{230}$ of the conjugate as described below. A similar approach was used for DC4 (see below).

Measurement of Releasable Pyridine-2-Thione and Ab Concentration of SPP-Modified Ab.

The molar ratio of pyridine-2-thione released per mole of antibody is calculated by measuring the $A_{280}$ of the sample and then the increase in the $A_{343}$ of the sample after adding DTT (50 µL of 1 M DTT/mL of sample). The concentration of DTT-released pyridine-2-thione is calculated using an $\epsilon_{343}$ of 8080 $M^{-1}\ cm^{-1}$. The concentration of antibody can then be calculated using an $\epsilon_{280}$ of 194,712 $M^{-1}\ cm^{-1}$ after subtracting the contribution of pyridine-2-thione absorbance at 280 nm ($A_{343\ nm}$ post DTT×5100/8080) from the total $A_{280\ nm}$ measured before DTT addition. The molar ratio of pyridine-2-thione:Ab can then be calculated. The mg/mL (g/L) concentration of Ab is calculated using a molecular weight of 147,000 g/mole.

Measurement of Antibody-Linked 5-Nitropyridyl-2-Dithio Groups and Ab Concentration of SSNPP-Modified Ab.

The molar ratio of the 4-nitropyridyl-2-dithio groups linked per mole of antibody is calculated by measuring the $A_{280}$ and $A_{325}$ of the sample without DTT treatment. The number of antibody-bound 4-nitropyridyl-2-dithio groups is calculated using an $\epsilon_{325\ nm}$ of 10,964 $M^{-1}\ cm^{-1}$. The concentration of antibody can then be calculated using an $\epsilon_{280}$ nm of 194,712 $M^{-1}\ cm^{-1}$ after subtracting the contribution of the 5-nitropyridyl-2-dithio group absorbance at 280 nm ($A_{325\ nm}$×3344/10964) from the total $A_{280\ nm}$ measured. The molar ratio of 4-nitropyridyl-2-dithio groups:Ab can then be calculated. The mg/mL (g/L) concentration of Ab is calculated using a molecular weight of 147,000 g/mole.

Calculating Ab and DM1 Component Concentrations of Ab-DM1.

The Ab and DM1 both absorb at the two wavelengths used to measure each component separately, i.e., 280 and 252 nm. The components are quantified using the following algebraic expressions which account for the contribution of each component at each wavelength ($C_{Ab}$ is the molar concentration of Ab and $C_D$ is the molar concentration of DM1):

$$\text{Total } A_{280} = 194{,}712 C_{Ab} + 5{,}700 C_D \quad (1)$$

$$\text{Total } A_{252} = (194{,}712 \times 0.37) C_{Ab} + (4.7 \times 5{,}700) C_D \quad (2)$$

Each equation is solved for $C_{Ab}$:

$$C_{Ab} = \frac{A_{280} - 5{,}700 C_D}{194{,}712} \quad (1a)$$

$$C_{Ab} = \frac{A_{252} - 26{,}790 C_D}{72{,}043} \quad (2a)$$

and an equality is set up (equation 1a=equation 2a) and solved for $C_D$:

$$C_D = \frac{A_{252} - 0.37 A_{280}}{24{,}681}$$

Once the $C_D$ is calculated, the value is used to solve for $C_{Ab}$ in equation 1a (or 2a) above. The ratio of DM1:Ab can then be calculated. The mg/mL (g/L) concentration of antibody is calculated using a molecular weight of 147,000 g/mole and the concentration of DM1 is calculated using a molecular weight of 736.5 g/mole (linked DM1)

Efficiency of Disulfide Exchange is Increased with SSNPP.

Figure 7:
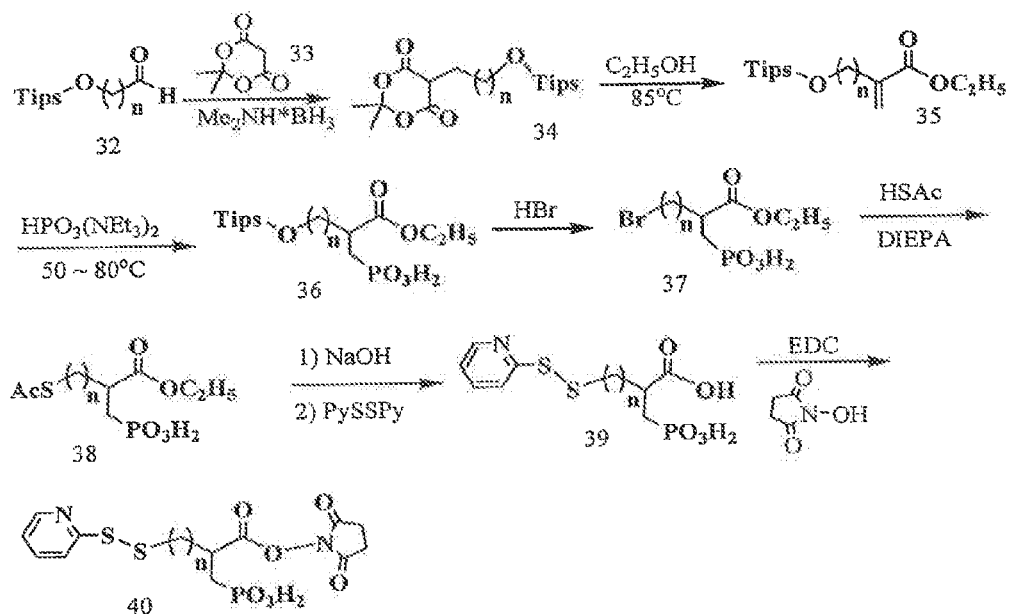
Figure 8:
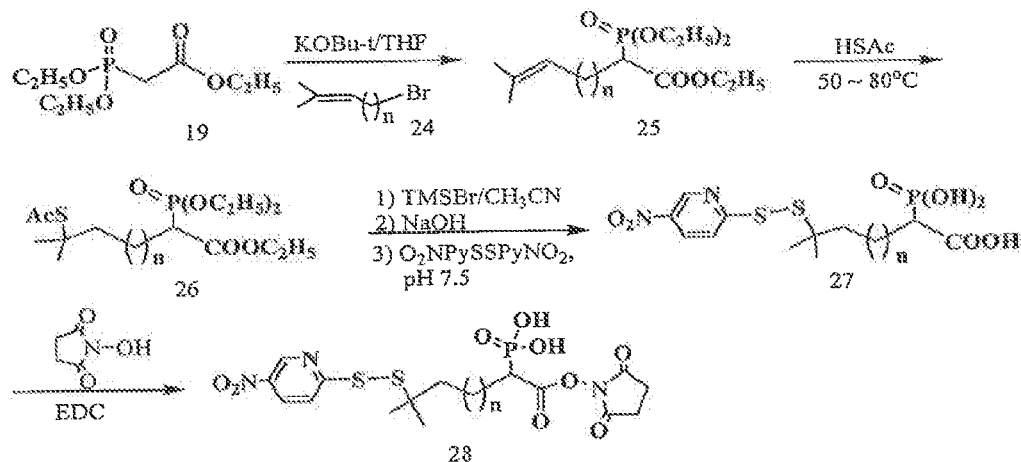
FIG. 8 shows the synthesis of phosphate-containing cross-linking reagents that contain a nitropyridyldisulfide group and a reactive carboxylic acid ester
Figure 9:
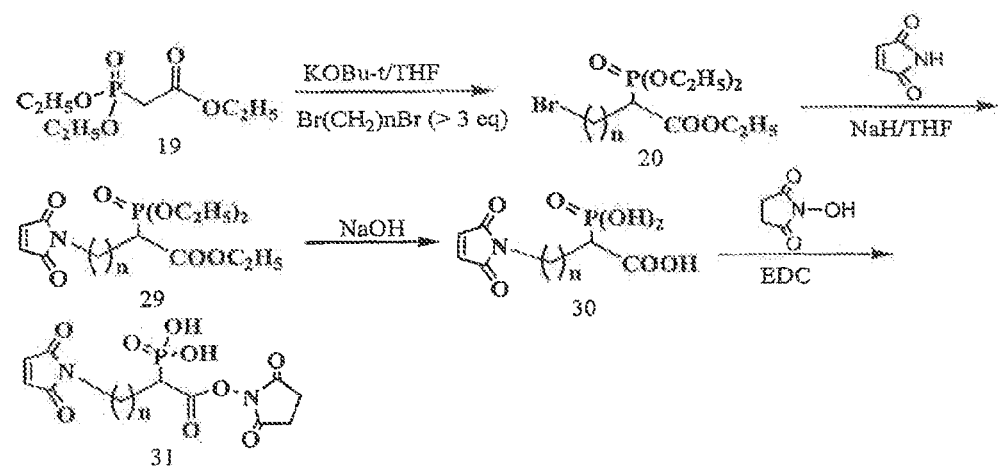
FIGS. 9 and 10 show different routes for the synthesis of phosphate-containing charged cross-linking agents bearing a reactive carboxylic acid ester and a maleimido substituent, enabling linkage via thioether bonds.
Figure 10:
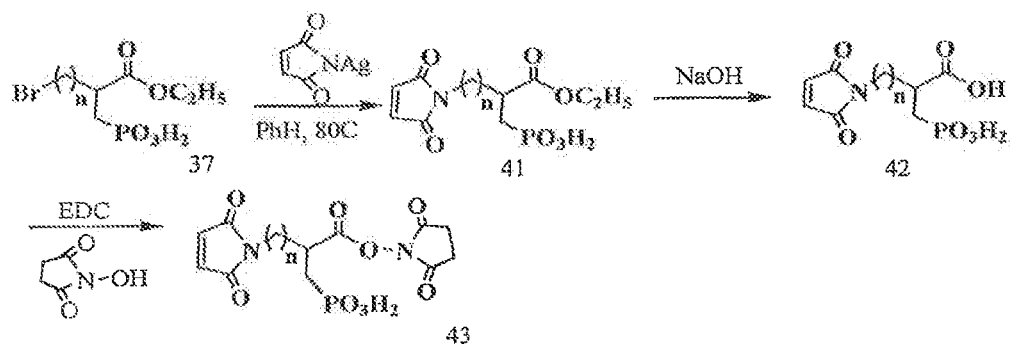
Figure 11:
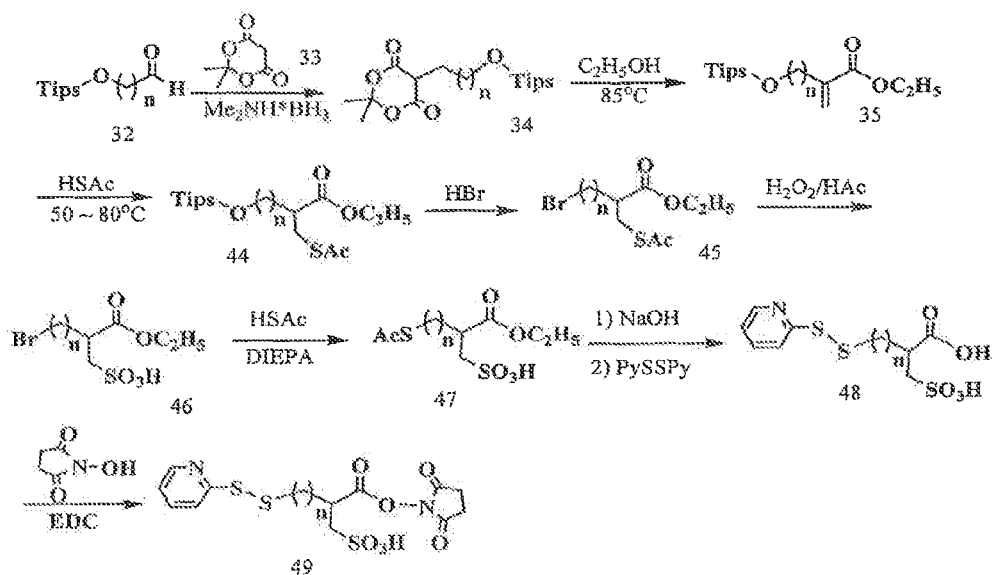
FIG. 11 shows the synthesis of sulfonic acid-containing cross-linking reagents, where the sulfonate substituent is attached to a branched alkyl group. These reagents also bear a pyridyldisulfide group and a reactive carboxylic acid ester.
Figure 12:
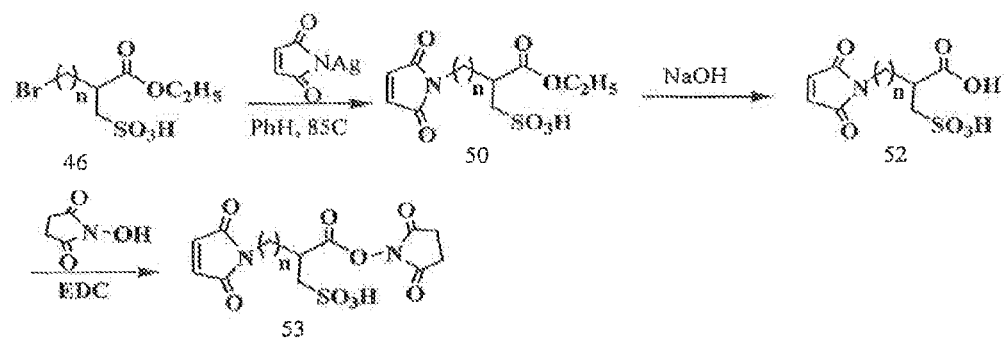
FIG. 12 shows the synthesis of sulfonic acid-containing cross-linking reagents, where the sulfonate substituent is attached to a branched alkyl group. These reagents also bear a reactive carboxylic acid ester and a maleimido group that allows for linkage via thioether bonds.

As shown in Table 1, the efficiency of conjugation is enhanced in reactions where SSNPP is used as the cross-linker compared to reactions using SPP. The percent efficiency was calculated by dividing the value for DM1 per antibody by the linker per antibody ratio times 100. Conjugations of the N901 antibody using SSNPP resulted in cross-linking efficiencies of 93% at both pH 6.5 and 7.4. The efficiency of conjugation of N901 with SPP in these experiments was 70% at pH 6.5 and 77% at pH 7.4. The increased efficiency with SSNPP demonstrates that a target DM1 to antibody ratio can be achieved using antibody that is modified with a reduced number of linker molecules. In fact, a similar drug to antibody ratio (4.3) was achieved in the final conjugate with an antibody preparation having 4.2 (5-nitropyridyl-2-dithio)-groups per antibody introduced with SSNPP compared to an antibody having 5.6 pyridyl-2-dithio groups introduced with SPP (Table 2). The amount of drug required to obtain comparable conjugation results was therefore 25% lower for the SSNPP-modified antibody than the SPP-modified antibody under these conditions. An additional potential benefit of the increased efficiency with SSNPP is that a reduced molar excess of DM1 may be used in the conjugation reaction. A comparison of the DM1 per antibody ratios following conjugation with a range of drug equivalents in the reaction (0.8-1.7 fold excess) shows that a 1.1-fold molar excess is sufficient to achieve 100% conjugation efficiency using the SSNPP cross-linker (FIG. 7). A comparison of the time course of the reaction of DM1 with antibody that had been modified with SSNPP or SPP is shown, for example, in FIG. 8. In each case the modified antibody was treated with a 1.1-fold molar excess of DM1 per mole of linker incorporated. The reaction with the SSNPP-modified antibody is considerably faster than with the SPP-modified antibody (FIG. 8). Even, a molar excess of 1.7-fold is not sufficient to achieve a similar efficiency using SPP. The ability to use 1) a lower molar excess of DM1 and 2) fewer linkers per antibody allows a reduction in the amount of drug needed to achieve a target DM1 to antibody ratio by as much as 50% when using SSNPP as the cross-linker instead of SPP.

The increased efficiency of conjugation using the SSNPP linker is accomplished without compromise in the monomeric character of the conjugate and in the amount of unconjugated (free) drug associated with the antibody conjugate. SEC analysis is used to determine the amount of monomer, dimer, trimer, or higher molecular weight aggregates. Typical results of greater than 90% monomer were obtained with either linker as shown in Table 1. The level of unconjugated drug was measured by reverse phase HPLC analysis of the conjugate sample. The percent free drug for either reaction was less than 2%. In addition, shorter conjugation reaction times are possible with SSNPP compared with SPP (U.S. Pat. No. 6,913,748), which may decrease loss of some antibodies that are sensitive to prolonged exposure to organic solvent required in the conjugation reaction. Shorter reaction times should also decrease drug loss due to DM1 dimerization, which is a competing side reaction during conjugation. The resulting increases in yield and reduced side reactions should further contribute to reduced DM1 requirements.

The enhanced rate and efficiency of conjugation when using SSNPP was also observed when conjugating a different drug to the antibody demonstrating the broad applicability of this new linker reagent. A comparison of conjugation efficiencies using SSNPP and SPP when conjugating the N901 antibody with the DNA-alkylating drug, DC4, a CC-1065 analogue, is shown, for example, in Table 3. By 2 hours the reaction using the SSNPP cross-linking reagent was complete whereas the reaction using the SPP reagent showed only 73% completeness by 2 hours and significant incorporation of drug beyond 2 hours (91% after 18 hours). Only much prolonged reaction times may lead to 100% completeness.

Example 3

In Vitro Cytotoxicity Evaluation of Maytansinoid Conjugates of Antibodies with Thioether (Non-Cleavable) and Disulfide Linkers Containing Sulfonate Group The cytotoxic effects of the antibody-maytansinoid conjugates with thioether and disulfide linkers containing a sulfonate group were typically evaluated using a WST-8 cell-viability assay after a 4-5 day continuous incubation of the cancer cells with the conjugates. The antigen-expressing cancer cells (~1000-5000 cells per well) were incubated in 96-well plates in regular growth medium containing fetal bovine serum with various concentrations of the antibody-maytansinoid conjugates for about 5 days. The WST-8 reagent was then added and the plate absorbance was measured at 450 nm after ~2-5 h. The survival fraction was plotted versus conjugate concentration to determine the $IC_{50}$ value (50% cell killing concentration) of the conjugate.

Figure 60:
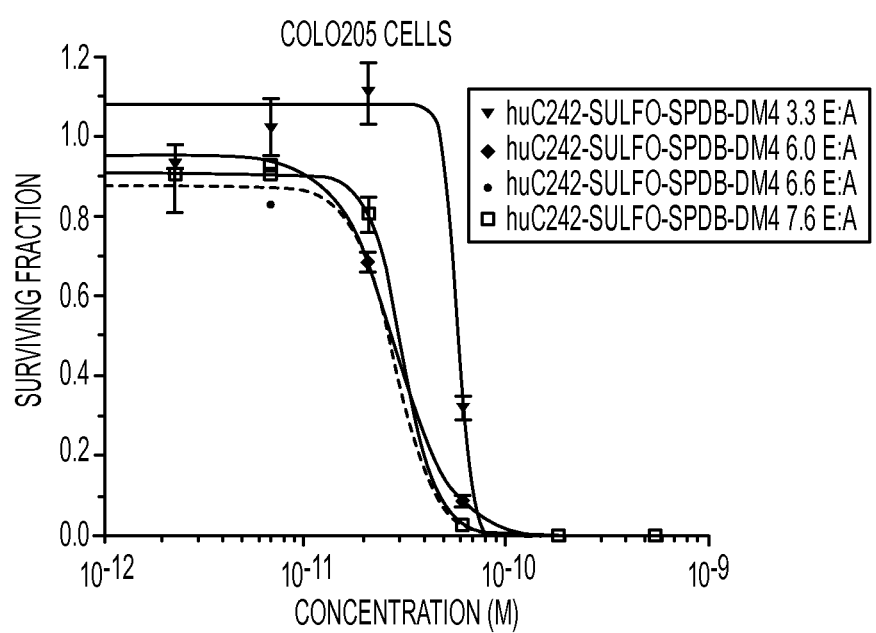
FIG. 60 shows the cytotoxicity of Anti-CanAg (huC242)-sulfonate linker-maytansinoid conjugates with increasing maytansinoids load (E:A) toward COLO205 cells.
Figure 61:
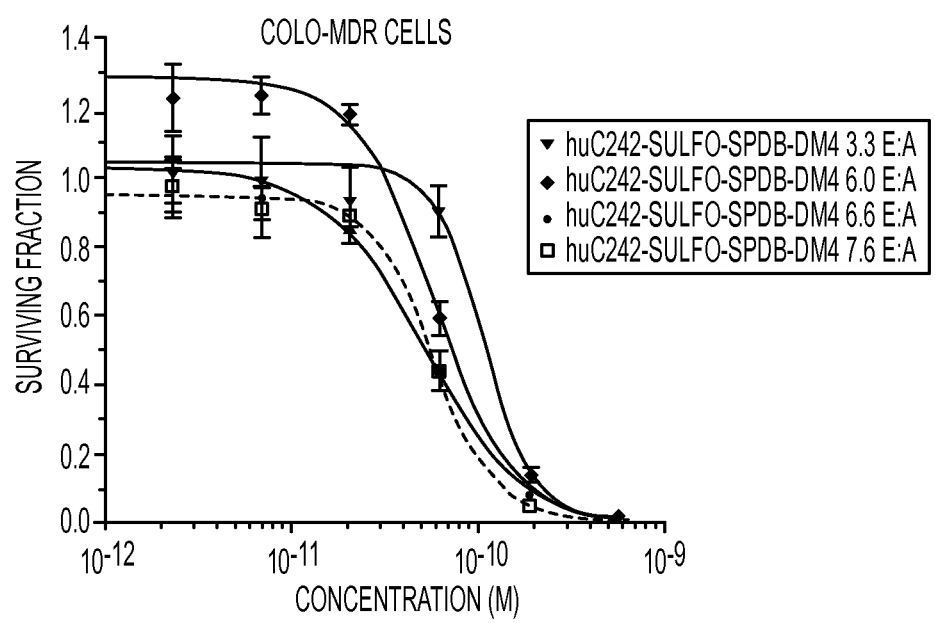
FIG. 61 shows the cytotoxicity of Anti-CanAg (huC242)-sulfonate linker-maytansinoid conjugates with increasing maytansinoids load (E:A) toward multi-drug resistant COLO205-MDR cells.
Figure 62:
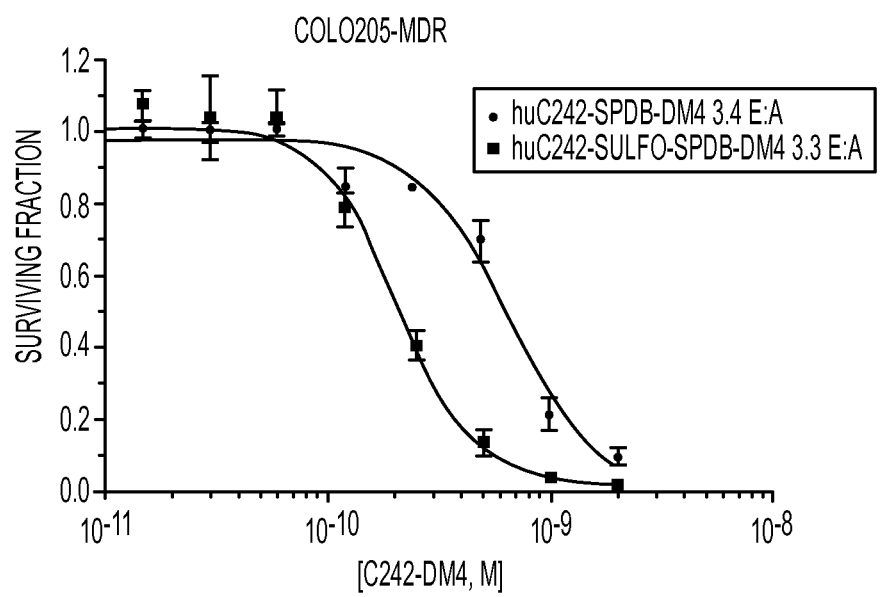
FIG. 62 compares cytotoxicity of Anti-CanAg (huC242)-maytansinoid conjugates with or without sulfonate group in the linker toward multi-drug resistant COLO205-MDR cells.

FIGS. 60 and 61 show the enhancement in cytotoxicities of Anti-CanAg (huC242)-maytansinoid conjugates with the sulfonate-containing disulfide-bonded linker (huC242-Sulfo-SPDB-DM4) bearing 6.0 to 7.6 maytansinoid/Ab compared to the conjugate with 3.3 maytansinoid/Ab toward CanAg-positive COLO205 and COLO205-MDR cells. The potency of the conjugates with high maytansinoids loads indicate that the decoration of the antibody with up to 8 maytansinoid molecules did not affect the conjugate binding to the target COLO205 cells.

Figure 64:
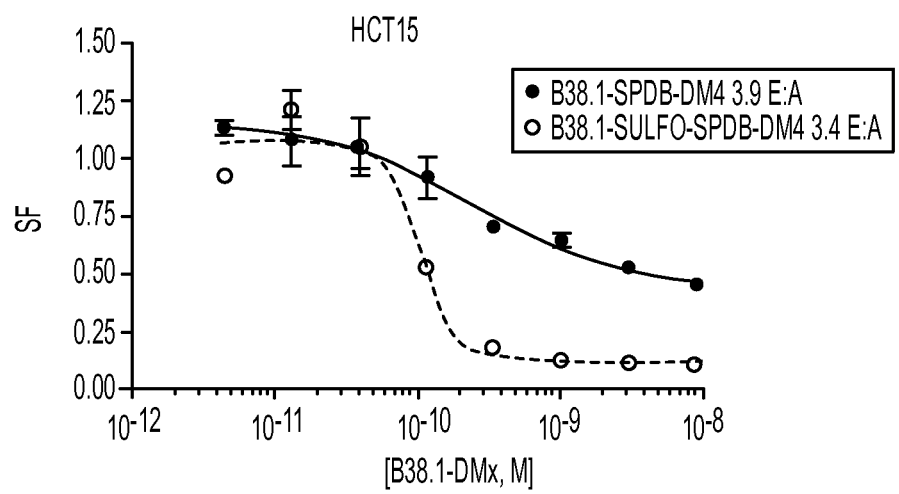
FIG. 64 compares the cytotoxicity of Anti-EpCAM (B38.1)-maytansinoid conjugates with or without sulfonate group in linker toward multi-drug resistant HCT15 cells.

FIG. 64 shows the cytotoxic activities of anti-CanAg Ab-maytansinoid conjugates with similar maytansinoid load against CanAg antigen-positive COLO205-MDR cells. The presence of sulfonate group in disulfide linker significantly enhanced conjugate potency toward these multiple drug resistant cells. The enhanced potency of the sulfonate-linked conjugate is a novel finding and potentially very promising for therapeutic applications.

Figure 63:
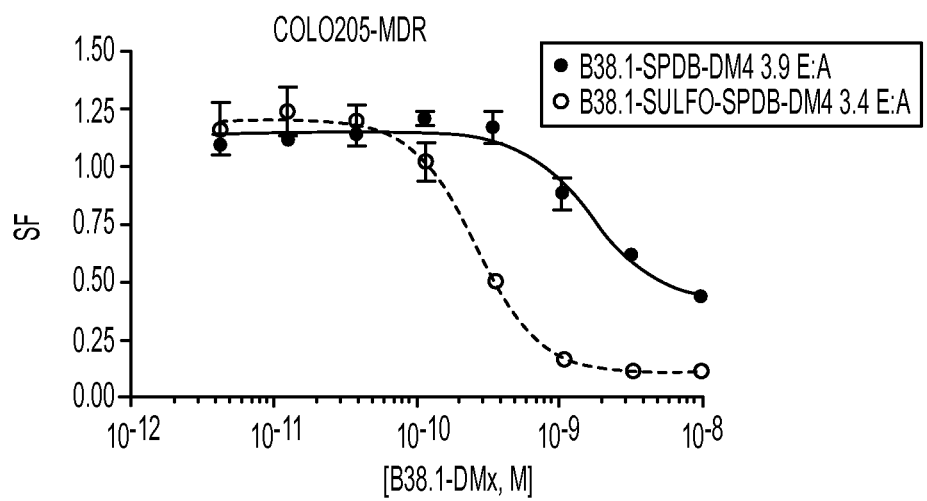
FIG. 63 compares the cytotoxicity of Anti-EpCAM (B38.1)-maytansinoid conjugates with or without sulfonate group in linker toward multi-drug resistant COLO205-MDR cells.

FIG. 63 shows the cytotoxic activities of anti-EpCAM Ab-maytansinoid conjugates with similar maytansinoid load against EpCAM antigen-positive COLO205-MDR cells. The presence of a sulfonate group in disulfide linker significantly enhanced conjugate potency toward these multiple drug resistant cells. The enhanced potency of the sulfonate-linked conjugate is a novel finding and potentially very promising for therapeutic applications.

FIG. 64 shows the cytotoxic activities of anti-EpCAM Ab-maytansinoid conjugates with similar maytansinoid load against EpCAM antigen-positive HCT cells. The presence of a sulfonate group in the disulfide linker significantly enhanced conjugate potency toward these multiple drug resistant cells. The enhanced potency of the sulfonate-linked conjugate is a novel finding and potentially very promising for therapeutic applications.

Figure 65:
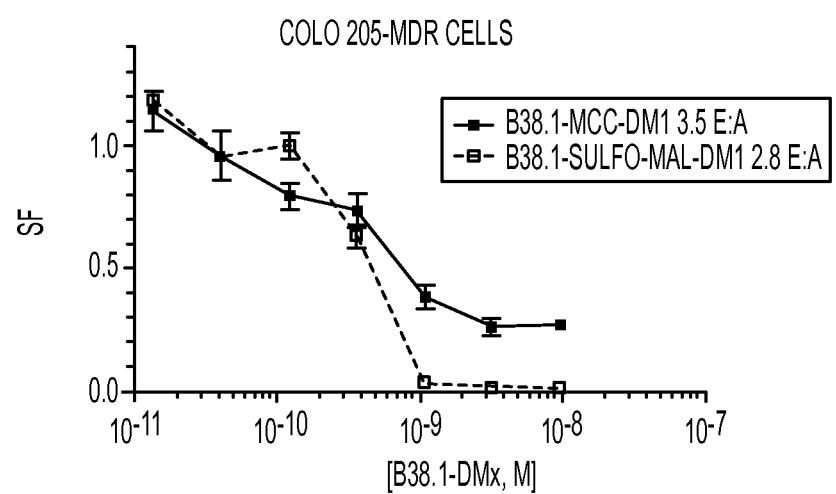
FIG. 65 compares the cytotoxicity of Anti-EpCAM (B38.1)-maytansinoid conjugates with or without sulfonate group in linker toward multi-drug resistant COLO205-MDR cells.

FIG. 65 shows the cytotoxic activities of anti-EpCAM Ab-maytansinoid conjugates with similar maytansinoid load against EpCAM antigen-positive COLO205-MDR cells. The presence of a sulfonate group in the thioether linker significantly enhanced conjugate potency toward these multiple drug resistant cells. The enhanced potency of the sulfonate-linked conjugate is a novel finding and potentially very promising for therapeutic applications.

Example 4

Comparison of In Vivo Anti-Tumor Activity of the Anti-EpCAM-Maytansinoid Conjugates, B38.1-SPDB-DM4 and B38.1-sulfo-SPDB-DM4, on Colon Cancer, COLO205 and COLO205-MDR, Xenografts The anti-tumor effect of B38.1-SPDB-DM4 and B38.1-sulfo-SPDB-DM4 conjugates was evaluated in a xenograft model of human colon carcinoma, COLO205 and COLO205-MDR, which was engineered to overexpress P-glycoprotein. The cells were injected subcutaneously in the area under the right shoulder of SCID mice. When the tumor's volume reached approximately 200 mm$^3$ in size, the mice were randomized by tumor volume and divided into three groups. Each group was treated with a single i.v. bolus of either B38.1-SPDB-DM4 (10 mg conjugate protein/kg), B38.1-sulfo-SPDB-DM4 (10 mg conjugate protein/kg) or phosphate-buffered saline (vehicle control). Tumor growth was monitored by measuring tumor size twice per week. Tumor size was calculated with the formula: length×width×height×½.

Figure 66:
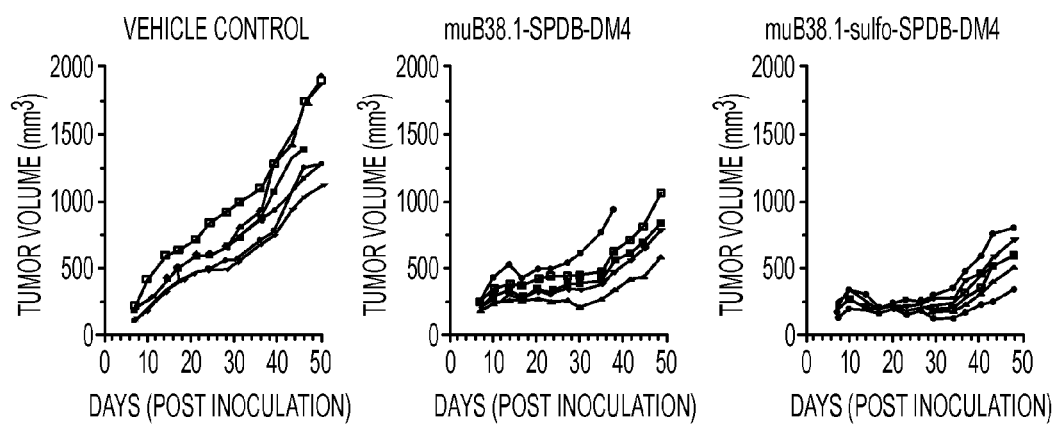
FIG. 66 shows the in vivo anti-tumor activity of anti-Ep-CAM antibody-maytansinoid conjugates on COLO205 mdr xenografts (individual tumors).

The changes in volumes of individual COLO205-MDR tumors are shown in FIG. 66. Treatment with either conjugate resulted in significant tumor growth delay. B38.1-sulfo-SPDB-DM4 was more efficacious than B38.1-sulfo-SPDB-DM4 in this human colon cancer xenograft model.

Figure 67:
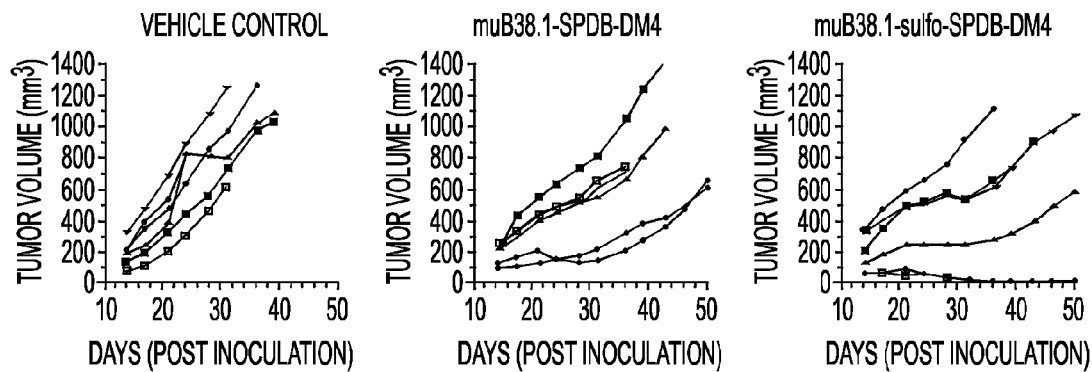
FIG. 67 shows the in vivo anti-tumor activity of anti-Ep-CAM antibody-maytansinoid conjugates on COLO205 xenografts (individual tumors).
Figure 68:
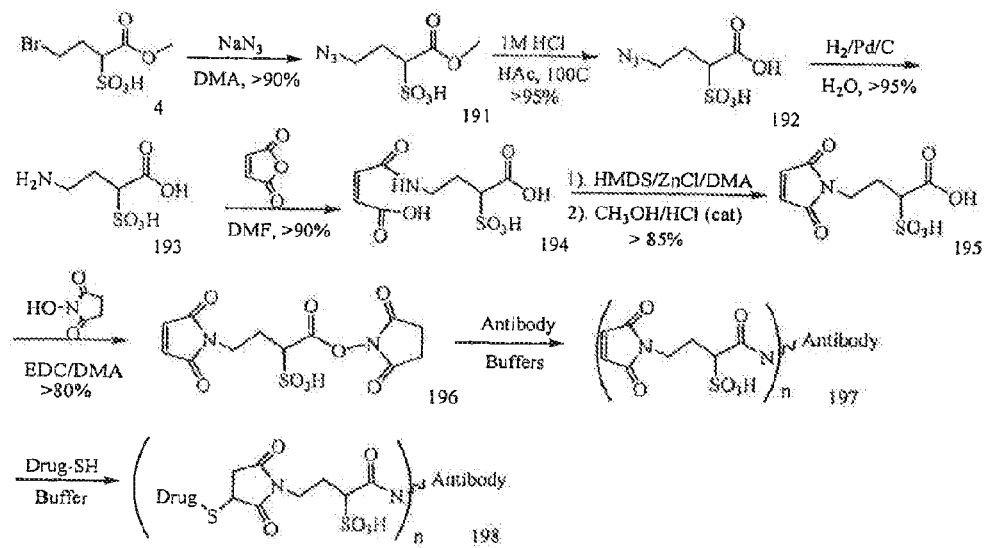
FIGS. 68-70 show the methods of synthesis of sulfonic acid-containing cross-linking reagents. These reagents bear a reactive carboxylic acid ester and a maleimido group that allows for linkage via thioether bonds.
Figure 69:
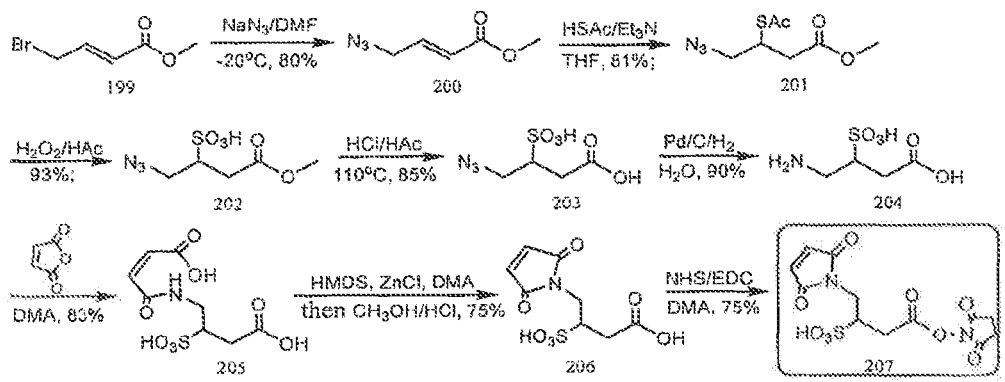
Figure 70:
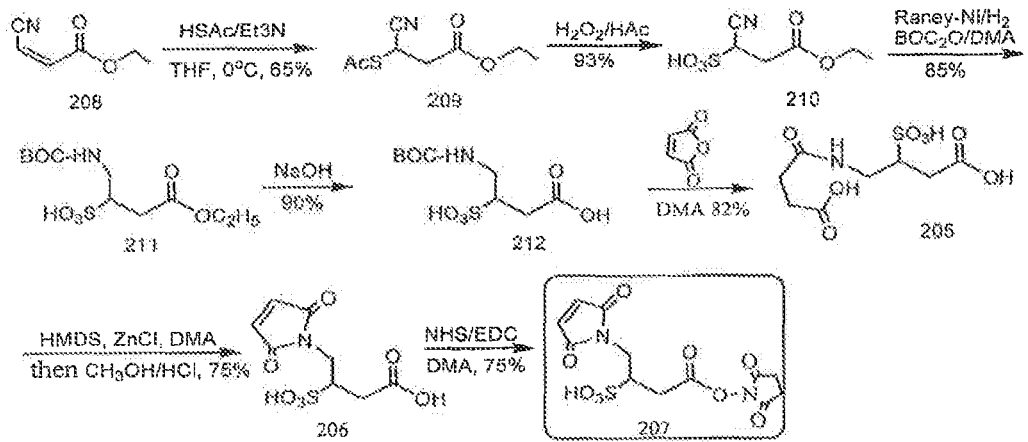

The changes in volumes of individual COLO205 tumors are shown in FIG. 67. Treatment with either conjugated resulted in significant tumor growth delay. Two of six animals treated with B38.1-sulfo-SPDB-DM4 had complete tumor regressions. Thus, B38.1-sulfo-SPDB-DM4 was significantly more efficacious than B38.1-sulfo-SPDB-DM4 in this model.

Example 5

Synthesis of Procharged Linkers (CX1-1): Z-Gly-Gly-Gly-β-Ala-OtBu

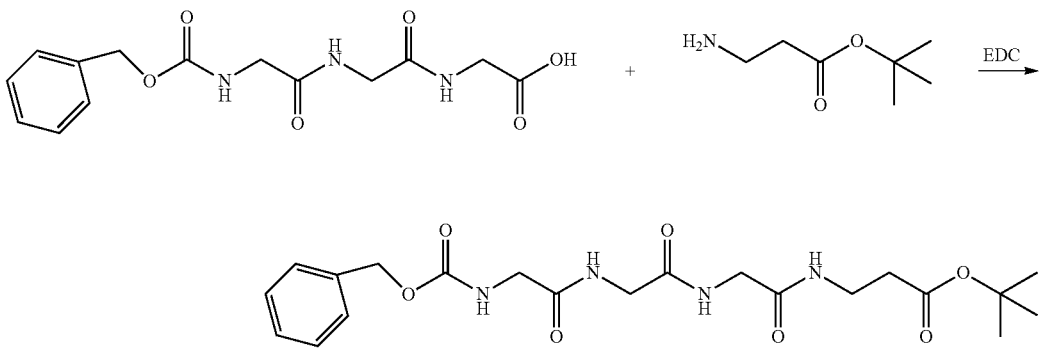

1.3 g (4.0 mmol) of Z-Gly-Gly-Gly-OH, 0.583 g (4.0 mmol) of tert-butyl-3-aminopropionate 0.651 g (4.25 mmol) of hydroxybenzotriazole and 0.81 g (4.23 mmol) of N-(3-dimethylaminopropyl)-N'-ethylcarbodiimide hydrochloride were weighed into a 50 mL flask then dissolved in 20 mL of dimethylformamide with magnetic stirring under a nitrogen atmosphere. After 3 hours the reaction mixture was purified in 5 mL portions by reverse phase HPLC using a 5.0 cm×25 cm C18 column. The column was run at 100 mL/min with deionized water containing 0.3% formic acid 5% acetonitrile for 10 min followed by a 15 min linear gradient from 5% acetonitrile to 90% acetonitrile. Product fractions (retention time of 19 min) were combined and solvent was removed by rotary evaporation under vacuum to give 1.35 g (75%) of the title compound. $^1$H NMR (d$_6$-DMSO) 8.16 (t, J=5.2 Hz, 1H), 8.10 (t, J=5.2 Hz, 1H), 7.82 (t, J=5.2 Hz, 1H), 7.25-7.4 (m, 5H), 5.04 (s, 2H), 3.74 (d, J=5.6 Hz, 2H), 3.67 (t, J=6.4 Hz, 4H), 3.25 (q, J=6.1 Hz, 2H), 2.35 (t, J=6.8 Hz, 2H), 1.39 (s, 9H). $^{13}$C NMR (d$_6$-DMSO) 170.45, 169.61, 169.00, 168.63, 156.49, 136.94, 128.30, 127.76, 127.69, 79.89, 65.51, 43.56, 42.10, 41.90, 34.89, 34.78, 27.70. HRMS (M+Na$^+$) Calc. 473.2012 found 473.1995.

H-Gly-Gly-Gly-β-Ala-OtBu

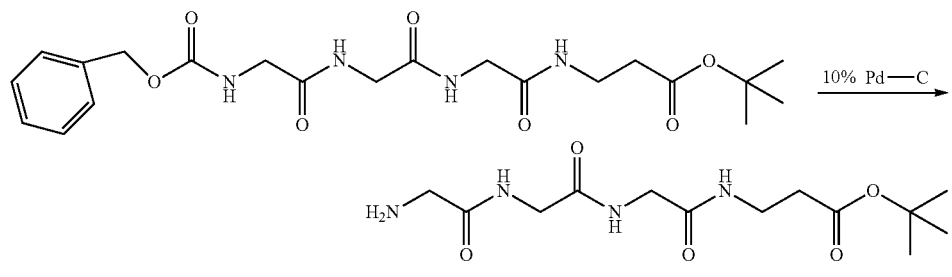

1.3 g (2.89 mmol) of Z-Gly-Gly-Gly-β-Ala-OtBu was dissolved in 80 mL of 95:5 methanol:deionized water in a 250 mL parr shaker flask to which was added 0.12 g of 10% palladium on carbon. The flask was shaken under a hydrogen atmosphere (42 PSI) for 7 hours. The mixture was vacuum filtered through celite filter aid and the filtrate was concentrated by rotary evaporation under vacuum to give 0.88 g (96%) of the title compound. $^1$H NMR (d$_6$-DMSO) 8.12 (t, J=1.6 Hz 2H), 8.08 (t, J=1.6 Hz, 1H), 3.75 (s, 2H), 3.64 (d, J=5.9 2H), 3.28 (bs, 2H), 3.24 (q, J=6.0 Hz, 2H), 3.13 (s, 2H), 2.35 (t, J=6.8 Hz, 2H), 1.39 (s, 9H). $^{13}$C NMR (d$_6$-DMSO) 173.38, 170.46, 169.18, 168.70, 79.89, 44.65, 41.95, 34.88, 34.78, 27.71. HRMS (M+H$^+$) Calc. 317.1825. found 317.1801

Mal-Gaba-Gly-Gly-Gly-β-Ala-OtBu

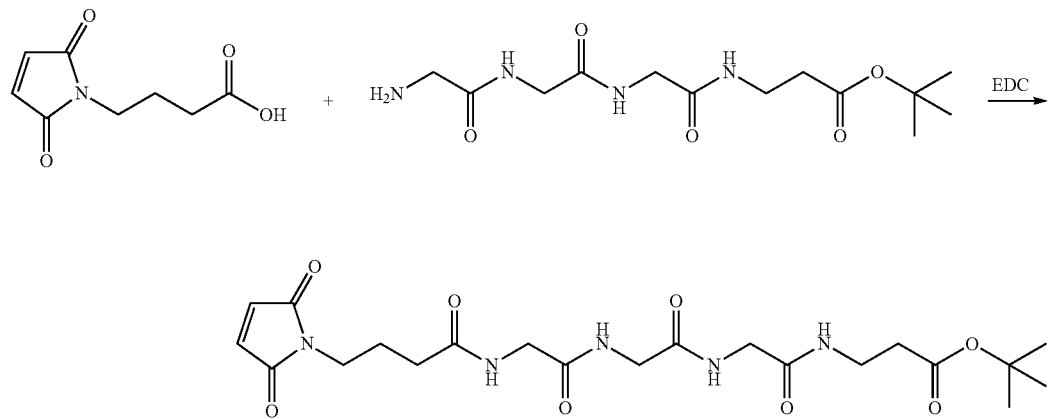

513 mg (2.8 mmol) of 4-(2,5-dioxo-2,5-dihydro-1H-pyrrol-1-yl)butanoic acid, 800 mg (0.2.8 mmol) tert-butyl 3-(2-(2-(2-aminoacetamido)acetamido)acetamido)propanoate and 583 mg (3.0 mmol) N-(3-dimethylaminopropyl)-N'-ethylcarbodiimide hydrochloride were dissolved in 12 mL of dimethyl formamide and stirred for 3 hours. The reaction mixture was purified in four equal portions by reverse phase HPLC using a 5.0 cm×25 cm C18 column. The column was eluted at 100 mL/min with deionized water containing 0.3% formic acid and 5% acetonitrile for 10 min followed by a 13 min linear gradient from 5% acetonitrile to 33% acetonitrile. Product fractions (retention time of 21 min) were combined and solvent was removed by rotary evaporation under vacuum to give 832 mg (62%) of the title compound. $^1$H NMR (d$_6$-DMSO) 8.10-8.16 (m, 2H), 8.07 (t, J=4.8 Hz, 1H), 7.0-7.15 (m, 1H), 3.747 (t, J=6.0 Hz, 3H), 3.64 (d, J=5.6 Hz, 2H), 3.41 (t, J=6.8, 2H), 3.1-3.33 (m, 1H), 3.19-3.26 (m, 2H), 2.348 (t, J=6.8, 2H), 2.132 (t, J=7.2 Hz, 2H), 1.67-1.76 (m, 2H), 1.39 (s, 9H). $^{13}$C NMR (d$_6$-DMSO) 171.80, 170.98, 170.39, 169.48, 168.96, 168.56, 134.37, 79.83, 42.05, 41.83, 37.38, 34.82, 34.71, 32.26, 27.83, 23.95. HRMS (M+Na$^+$) Calc. 504.2070 found 504.2046

Mal-Gaba-Gly-Gly-Gly-β-Ala-OH

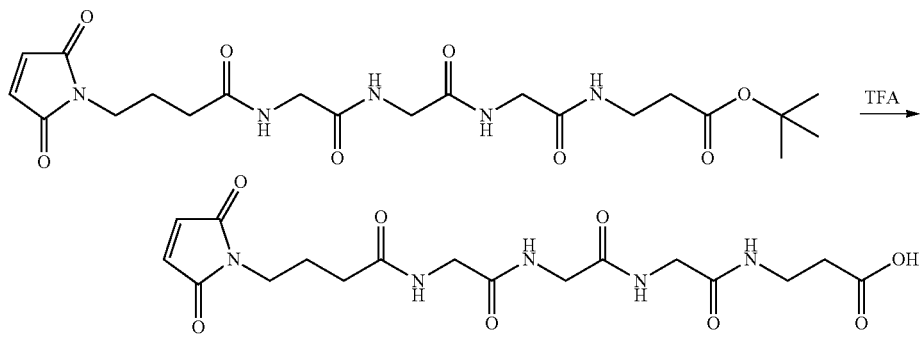

820 mg (1.7 mmol) of Mal-Gaba-Gly-Gly-Gly-β-Ala-OtBu was dissolved in 9.0 mL of 95:5 trifluoroacetic acid: deionized water and magnetically stirred for 3 hours. Solvent was removed by rotary evaporation under vacuum to give 730 mg (100%) of the title compound. $^1$H NMR (d$_6$-DMSO) 12.1 (bs, 1H), 8.05-8.20 (m, 3H), 7.82 (t, J=6.0 Hz, 1H), 7.00 (s, 2H), 3.71 (t, J=6.0 Hz, 4H), 3.65 (d, J=6.0 Hz, 2H), 3.41 (t, J=7.2 Hz, 2H), 3.26 (q, J=5.6 Hz, 2H), 2.38 (t, J=7.2 Hz, 2H,), 2.14 (q, J=8.0 Hz, 2H), 1.67-1.77 (m, 2H). $^{13}$C NMR (d$_6$-DMSO) 172.70, 171.83, 171.01, 169.50, 168.99, 168.51, 134.38, 42.07, 41.84, 36.75, 34.70, 33.69, 32.28, 23.97 HRMS (M+Na$^+$) Calc. 448.1444 found 448.1465

Mal-Gaba-Gly-Gly-Gly-β-Ala-ONHS (CX1-1)

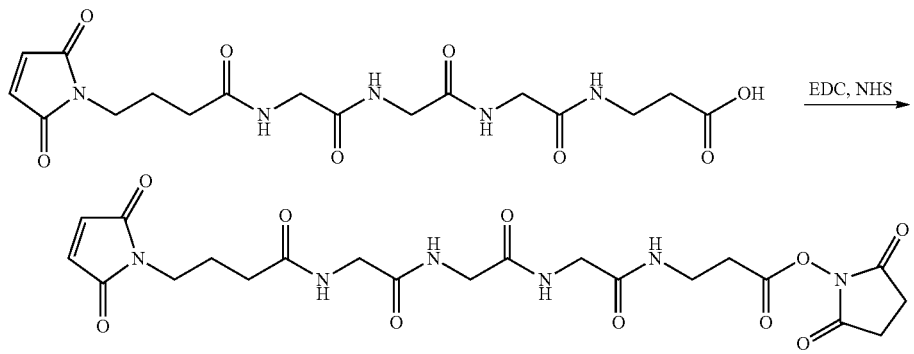

76 mg (0.18 mmol) of Mal-Gaba-Gly-Gly-Gly-β-Ala-OH, 72 mg, (0.376 mmol) of N-(3-dimethylaminopropyl)-N'-ethylcarbodiimide hydrochloride and 66 mg (0.575 mmol) of N-hydroxysuccinimide were dissolved in 1.0 mL of dimethylformamide with magnetic stirring. After 2 hours the reaction mixture was purified in two equal portions by reverse phase HPLC using a 1.9 cm×10 cm C8 column. The column was eluted at 18 mL/min with deionized water containing 0.3% formic acid and 5% 1,4-dioxane for 3 min followed by a 15 min linear gradient from 5% 1,4-dioxane to 30% 1,4-dioxane. Product fractions (retention time 6.5 min) were collected in a flask and immediately frozen in a dry ice acetone bath. Solvent was removed by lyophilization at ambient temperature to give 40 mg (42%) of the title compound. $^1$H NMR (d$_6$-DMSO) 8.08-8.11 (m, 3H), 7.99 (t, J=6.4 Hz, 1H), 7.00 (s, 2H), 3.6-3.75 (m, 6H), 3.0-3.2 (m, 4H), 2.84 (s, 4H), 2.13 (t, J=7.6 Hz), 1.83-1.93 (m, 2H), 1.69-1.72 (m, 2H). HRMS (M+Na$^+$) calc. 545.1608 found 545.1638

Z-Glu(OtBu)-Gly_Gly-NH$_2$

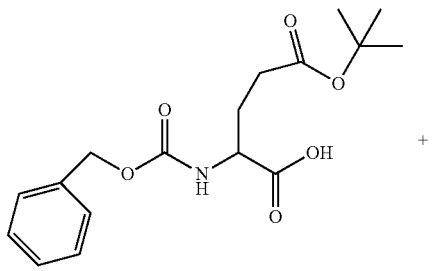

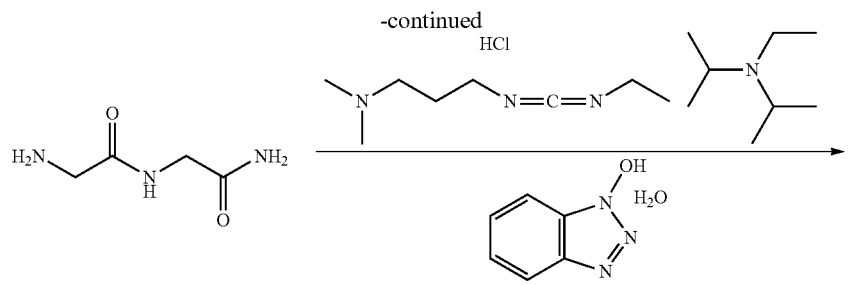

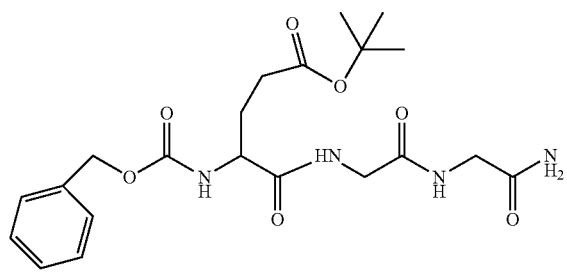

40 mL of Dimethyl formamide was added to 2.52 g (7.47 mmol) of Z-Glu(OtBu)-OH, 1.3 g (8.49 mmol) of hydroxybenzotriazole, 1.3 g (7.76 mmol) of H-Gly-GlyNH2, and 1.52 g (7.93 mmol) of N-(3-dimethylaminopropyl)-N'-ethylcarbodiimide hydrochloride. 2.5 mL (14.3 mmol) of diisopropyl ethyl amine was added and the reaction was stirred over night. The reaction mixture was purified in three equal portions by direct injection on a preparative 5 cm×25 cm C18 HPLC column. The column was run at 100 mL/min with deionized water containing 0.3% formic acid with 5% acetonitrile for 10 min followed by a 15 min linear gradient from 5% acetonitrile to 90% acetonitrile. Product fractions (retention time 18-20 min) were combined and solvent was removed by rotary evaporation under vacuum to give 2.9 g (83%) of the title compound. $^1$H NMR (400 MHz, CDCl$_3$) δ 7.79-7.68 (m, 1H), 7.64 (s, 1H), 7.27 (q, J=4.9, 5H), 6.90 (s, 1H), 6.42 (s, 1H), 6.35 (d, J=6.8, 1H), 5.08 (d, J=12.0, 1H), 4.98 (d, J=12.2, 1H), 4.20 (dd, J=12.9, 7.6, 1H), 3.84-3.95 (m, 2H), 3.83 (d, J=5.0, 2H), 2.42-2.19 (m, 2H), 2.07 (d, J=6.9, 1H), 1.96-1.83 (m, 1H), 1.39 (s, 9H). $^{13}$C NMR (101 MHz, DMSO) δ 171.79, 171.65, 170.82, 168.87, 163.04, 156.08, 136.86, 128.31, 127.74, 79.64, 65.58, 53.96, 42.17, 41.81, 31.25, 27.73, 27.01.

H-Glu(OtBu)-Gly-Gly-NH$_2$ 940 mg (2.09 mmol) of Z-Glu(OtBu)-Gly-GlyNH2 was dissolved in 40 mL of 95:5 methanol:de-ionized water in a 250 mL glass PARR hydrogenation shaker flak. 222 mg of 10% palladium on carbon was added to the flask and the contents were hydrogenated with shaking under hydrogen (40 PSI) for 4 hours. The mixture was vacuum filtered though celite filter aid and solvent was removed from the filtrate by rotary evaporation to give 640 mg (94%) of the title compound. $^1$H NMR (400 MHz, DMSO) δ 4.03 (s, 1H), 3.75 (d, J=3.3, 2H), 3.63 (s, 2H), 3.30-3.22 (m, J=3.6, 1H), 3.14-3.10 (m, 1H), 2.27 (t, J=7.9, 2H), 1.84 (td, J=13.6, 7.4, 1H), 1.63 (td, J=15.0, 7.5, 1H), 1.39 (s, 9H). $^{13}$C NMR (101 MHz, MeOD) δ 176.53, 174.24, 172.00, 170.32, 81.82, 55.21, 43.64, 43.16, 40.44, 32.31, 30.45, 28.41. HRMS (M+H$^+$) Calc. 317.1825 found 317.1800.

E001008-28 Mal-Gaba-Glu(OtBu)-Gly-Gly-NH$_2$

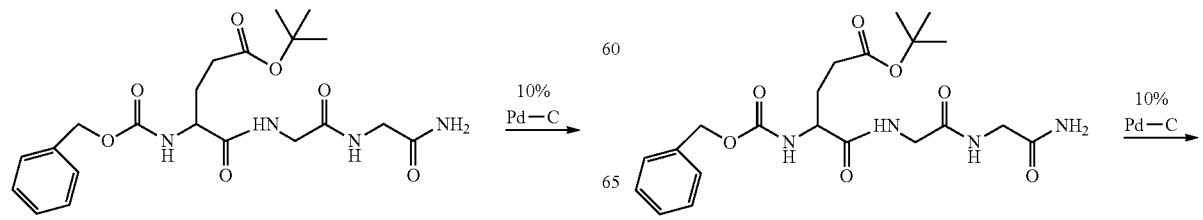

-continued

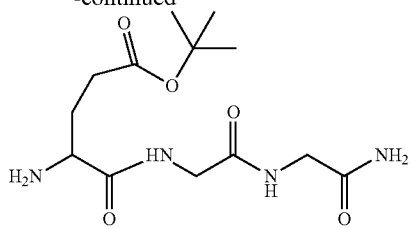

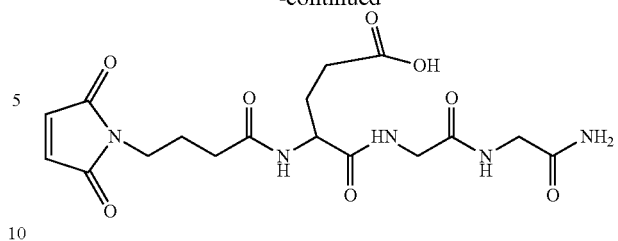

603 mg (1.9 mmol) of H-Glu(OtBu)-Gly-Gly-NH2, 372 mg (2.03 mmol) of Mal-Gaba-OH and 430 mg (2.24 mmol) of N-(3-dimethylaminopropyl)-N'-ethylcarbodiimide hydrochloride were dissolved in 4.5 mL of dimethyl formamide and 800 μL of dichloromethane. The reaction was stirred for 3 hours at ambient temperature. The reaction mixture was purified in two equal portions by direct injection on a preparative 5 cm×25 cm C18 HPLC column. The column was run at 100 mL/min with deionized water containing 0.3% formic acid 5% acetonitrile for 10 min followed by a 15 min linear gradient from 5% acetonitrile to 90% acetonitrile. Product fractions (retention time 17.4-19.2 min) were combined and solvent was removed by rotary evaporation under vacuum to give 2.9 g (83%) of the title compound. $^1$H NMR (400 MHz, CDCl$_3$) δ 8.16 (t, J=5.7, 1H), 8.06 (d, J=7.4, 1H), 7.99 (t, 105 mg (0.218 mmol) of Mal-Gaba-Glu(OtBu)-Gly-Gly-NH2 was dissolved in 5 mL of 95:5 trifluoroacetic acid:deionized water and magnetically stirred for 2 hours. Solvent was removed by rotary evaporation and residue was taken up in 6 mL acetonitrile+1.5 mL toluene to give a suspension. Solvent was evaporated from the suspension by rotary evaporation under vacuum to give 92 mg (100%) of the title compound. $^1$H NMR (400 MHz, DMSO) δ 6.99 (s, 2H), 4.18 (dd, J=8.2, 5.7, 1H), 3.70 (s, 2H), 3.61 (s, 2H), 3.40 (t, J=6.8, 2H), 2.26 (t, J=7.8, 2H), 2.19-2.05 (m, 2H), 1.90 (dt, J=13.7, 7.4, 1H), 1.73 (dt, J=14.2, 7.5, 3H). $^{13}$C NMR (101 MHz, DMSO) δ 173.76, 171.72, 170.99, 170.70, 168.81, 134.37, 52.00, 41.97, 41.63, 36.75, 32.19, 29.95, 26.79, 23.93.

Mal-Gaba-Glu(ONHS)-Gly-Gly-NH$_2$

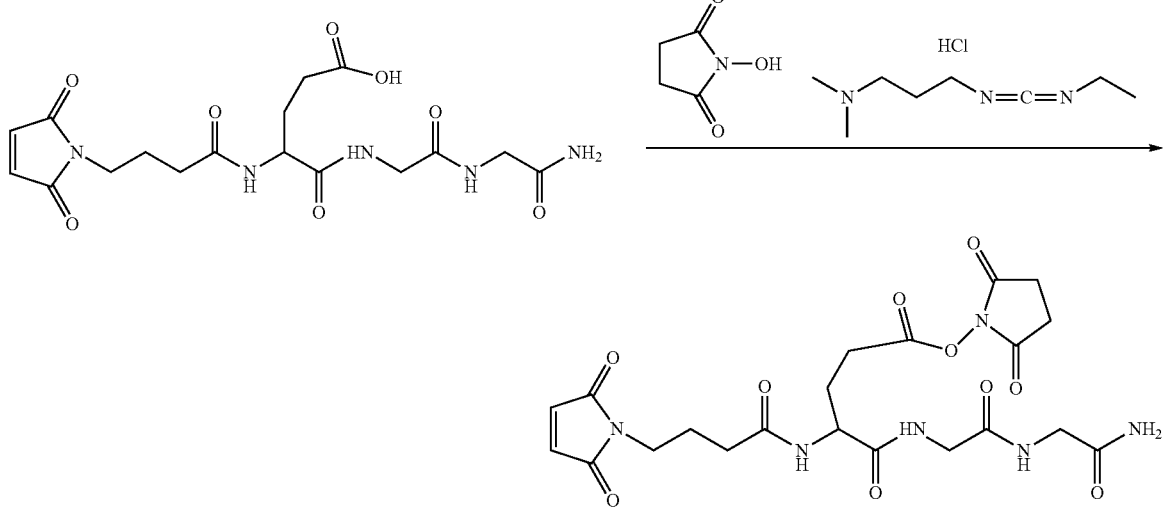

J=5.8, 1H), 7.19 (s, 1H), 7.06 (s, 2H), 4.18 (dd, J=13.4, 7.9, 1H), 3.70 (d, J=5.7, 2H), 3.62 (d, J=5.8, 2H), 3.42-3.37 (m, 2H), 2.23 (t, J=8.0, 2H), 2.12 (dd, J=8.1, 6.4, 2H), 1.87 (dt, J=14.2, 7.9, 1H), 1.70 (dt, J=13.7, 6.8, 2H), 1.38 (s, 9H). $^{13}$C NMR (101 MHz, DMSO) δ 173.12, 171.77, 171.65, 171.03, 170.79, 168.89, 134.43, 79.62, 52.02, 42.14, 41.81, 36.80, 32.29, 31.22, 27.73, 26.95, 24.02. HRMS (M+Na$^+$) Calc. 504.2070 found 504.2053.

Mal-Gaba-Glu(OH)-Gly-Gly-NH$_2$

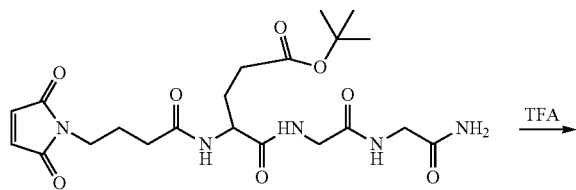

94 mg (0.22 mmol) of Mal-Gaba-Glu(OH)-Gly-Gly-NH$_2$, 75 mg (0.65 mmol) N-hydroxysuccinimide and 110 mg (0.57 mmol) of N-(3-dimethylaminopropyl)-N'-ethylcarbodiimide hydrochloride were magnetically stirred in 1 mL of dimethyl formamide for 3 hours. The crude reaction mixture was purified in three equal portions by direct injection on a 1.9 cm×10 cm C8 column. The column was run at 18 mL/min with deionized water containing 0.3% formic acid and 5% 1,4-dioxane for 3 min followed by an 18 min linear gradient from 5% 1,4-dioxane to 30% 1,4-dioxane. Product fractions (retention time 7.3 min) were collected in a flask and immediately frozen in a dry ice/acetone bath. The combined frozen material was lyophilized to give 80 mg (70%) of the title compound. $^1$H NMR (400 MHz, DMSO) δ 8.20 (t, J=5.4, 1H), 8.13 (d, J=7.3, 1H), 8.03 (t, J=5.6, 1H), 7.21 (s, 1H), 7.06 (s, 1H), 7.01 (s, 2H), 4.29 (dd, J=13.7, 6.5, 1H), 3.84-3.69 (m, 2H), 3.63 (d, J=5.7, 2H), 3.57 (s, 2H), 3.41 (t, J=6.8, 2H), 2.81 (s, 3H), 2.78-2.69 (m, 2H), 2.15 (dd, J=9.1, 6.2, 1H), 2.10-

1.95 (m, 1H), 1.88 (dt, J=17.0, 7.5, 1H), 1.73 (dd, J=14.0, 6.9, 2H). HRMS (M+Na+) Calc. 545.1608 found 545.1627.

Example 6

Synthesis of Positively Charged Linker

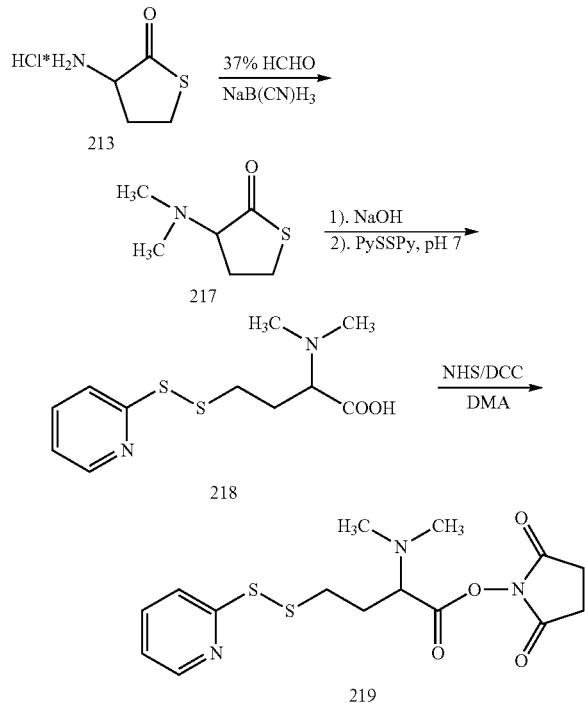

3-(Dimethylamino)dihydrothiophen-2(3H)-one (217)

3-aminodihydrothiophen-2(3H)-one hydrochloride (213) (1.0 g, 6.51 mmol) and formaldehyde (3 ml, 40.3 mmol) in methanol was added sodium cynoboronhydride (0.409 g, 6.51 mmol) in five portions in 1 h. After being stirred for 2 h, the mixture was evaporated, redissolved in EtAc, washed with 1 M $NaH_2PO_4$, dried over $MgSO_4$, filtered, concentrated and purified by $SiO_2$ column eluted with MeOH/DCM (1:30) to afford 0.812 g (86%) of the title compound. 1H NMR ($CDCl_3$) 3.49 (dd, 1H, J=6.3, 12.1 Hz), 3.24 (m, 2H), 2.42 (s, 6H), 2.38 (m, 1H), 2.21 (m, 1H); 13C NMR 206.58, 73.24, 41.62, 27.47, 25.51; ESI MS m/z+146.0 (M+H), 168.0 (M+Na).

2-(dimethylamino)-4-(pyridin-2-yldisulfanyl)butanoic acid (218)

3-(dimethylamino)dihydrothiophen-2(3H)-one (217) (0.95 g, 6.54 mmol) was stirred in 15 ml of 0.5 M NaOH and 10 ml of methanol solution for 30 min, neutralized with $H_3PO_4$ to pH 7.2, and 1,2-di(pyridin-2-yl)disulfane (5.76 g, 26.2 mmol) in 50 ml of methanol was added. The mixture was stirred overnight, concentrated, washed with EtAc and the aqueous solution was loaded on C-18 column, eluted from 5% methanol in 0.01% formic acid to 30% methanol in 0.01% formic acid to afford the title product (368 mg, 20.65% yield). $^1$H NMR ($CDl_3OD$) 8.31 (dd, 1H, J=0.7, 4.7 Hz), 7.77 (m, 2H), 7.15 (dd, 1H, J=0.8, 5.8 Hz), 3.22 (m, 1H), 2.85 (m, 2H), 2.51 (s, 6H), 2.05 (m, 2H); $^{13}$C NMR 175.00, 161.28, 150.46, 139.40, 122.60, 121.49, 71.20, 42.46, 36.29, 29.88; ESI MS m/z+ 272.9 (M+H), 295.0 (M+Na).

2,5-dioxopyrrolidin-1-yl 2-(dimethylamino)-4-(pyridin-2-yldisulfanyl)butanoate (219)

2-(dimethylamino)-4-(pyridin-2-yldisulfanyl)butanoic acid (218) (92 mg, 0.338 mmol), 1-hydroxypyrrolidine-2,5-dione (65 mg, 0.565 mmol) and EDC (185 mg, 0.965 mmol) was stirred in 3 ml of DMA at 50° C. overnight. The mixture was evaporated and purified on a $SiO_2$ column eluted with from 1:10 to 1:4 of methanol/$CH_2Cl_2$ to afford 43 mg (35%) of the title product. $^1$H NMR ($CDl_3OD$) 8.40 (m, 1H), 7.83 (m, 2H), 7.22 (m, 1H), 3.34 (m, 1H), 2.82 (m, 2H), 2.75 (s, 4H), 2.66 (s, 6H), 1.98 (m, 2H); $^{13}$C NMR 177.21, 161.78, 161.12, 150.68, 139.37, 122.70, 121.66, 70.80, 44.16, 43.15, 36.06, 27.38; ESI MS m/z+ 369.2 (M+H).

Example 7

Preparation of huMy9-6-CX1-1-DM1 Procharged Linker Conjugates

The following stock solutions were used: 39.6 mM DM1 in DMA; (2) 17.8 mM solution of CX1-1 linker in DMA; (3) 200 mM succinate buffer pH 5.0 with 2 mM EDTA. The reaction mixture containing between 8, 12 or 16 equivalents of linker to antibody were added to a solution of the antibody at 4 mg/ml in 90% phosphate buffer pH 6.5)/10% DMA and allowed to react for 2 h at 25° C. pH 5.0, followed by reaction with DM1.

The Ab conjugate was separated from excess small molecule reactants using a G25 column equilibrated in PBS pH 7.4. The purified conjugate was allowed to hold for 2 d at 25'C to allow any labile drug linkages to hydrolyze and then the conjugate was further purified from free drug by dialysis in PBS overnight, and then 10 mM histidine/130 mM glycine buffer pH 5.5 (1× o/n). The dialyzed conjugate was filtered using a 0.2 um filter and assayed by UV/Vis to calculate number of maytansinoids per Ab using known extinction coefficients for maytansinoid and antibody at 252 and 280 nm. The recovery was ~70% and number of maytansinoids/antibody measured for each conjugate ranged from 3.7 to 6.8 depending on the linker excess used.

Example 8

In Vivo Pharmacokinetics

Figure 38:
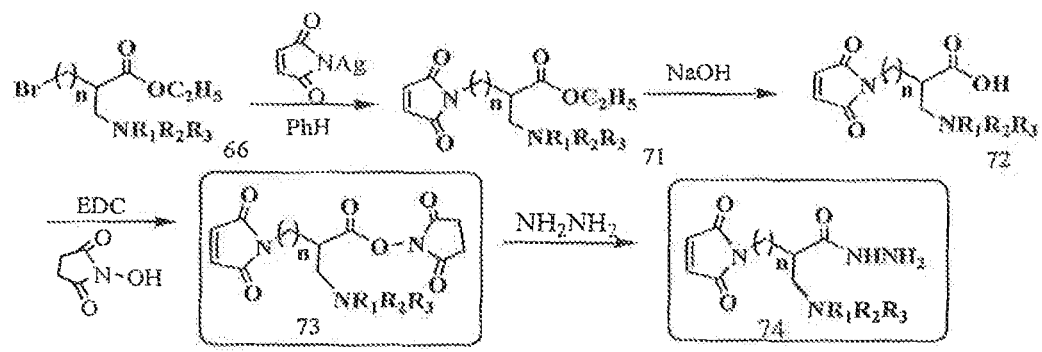
Figure 39:
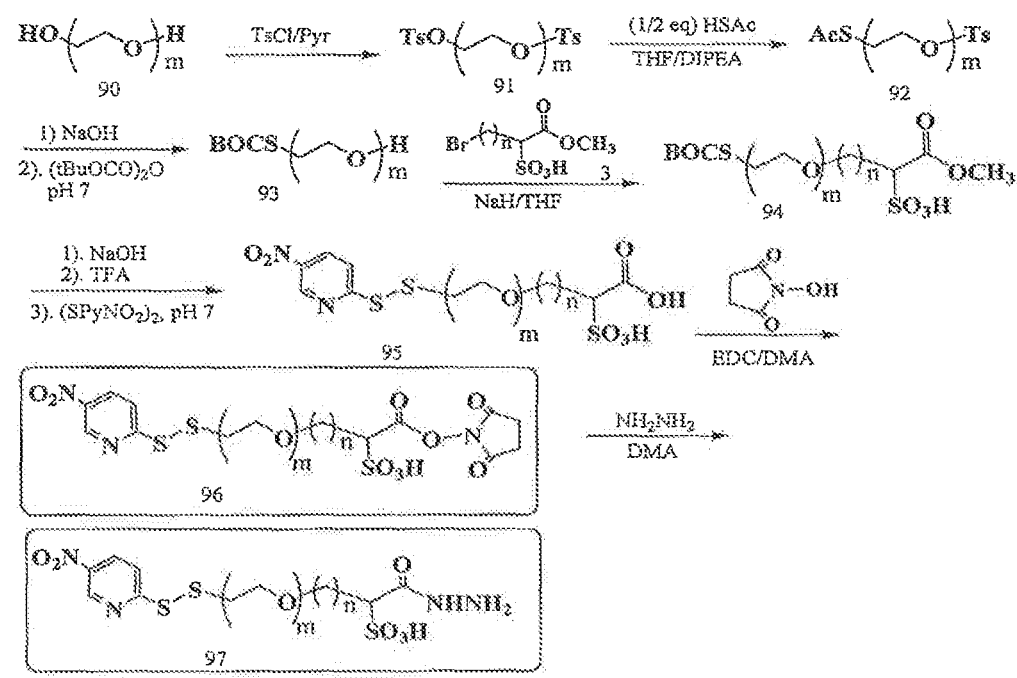
FIGS. 39-42 show the synthesis of charged cross-linking reagents that also incorporate a polyethyleneglycol (PEG) moiety.
Figure 40:
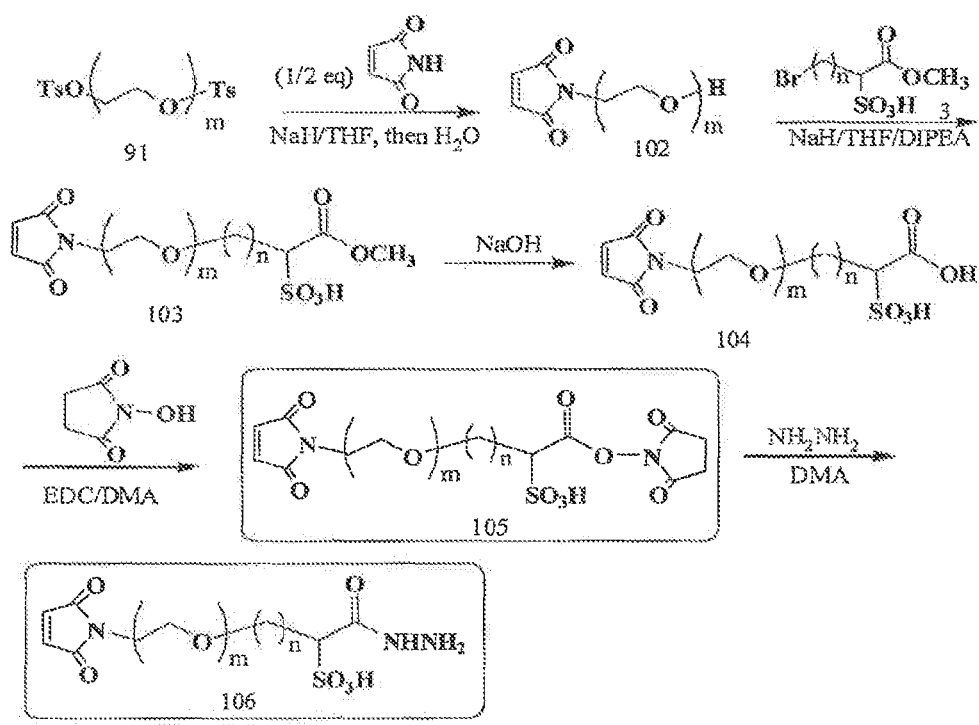
Figure 41:
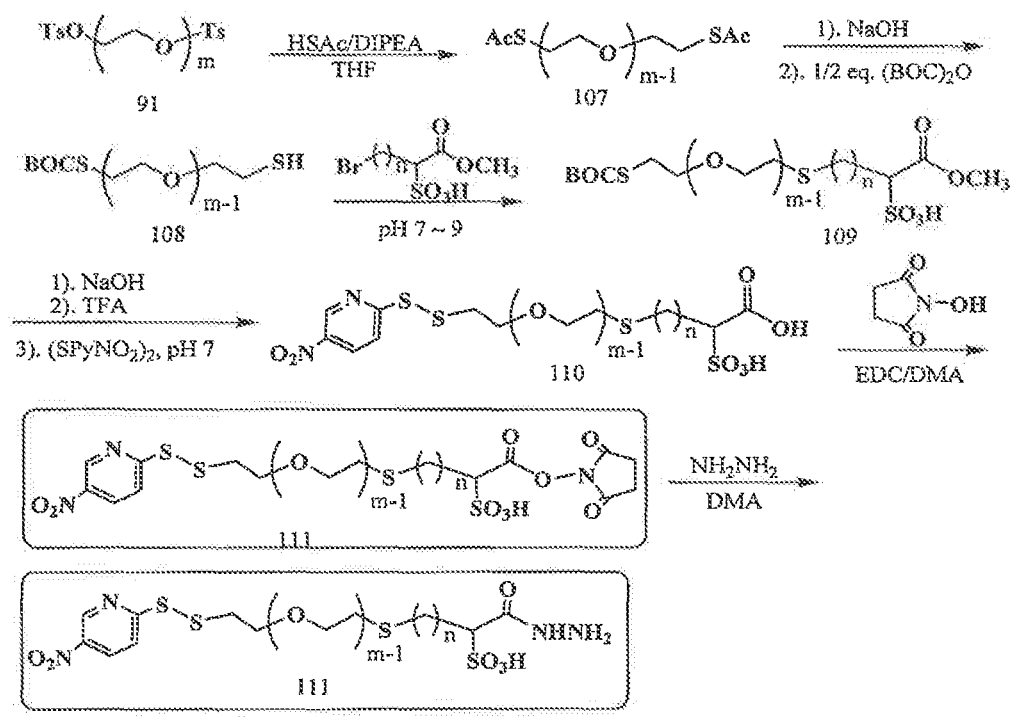
Figure 42:
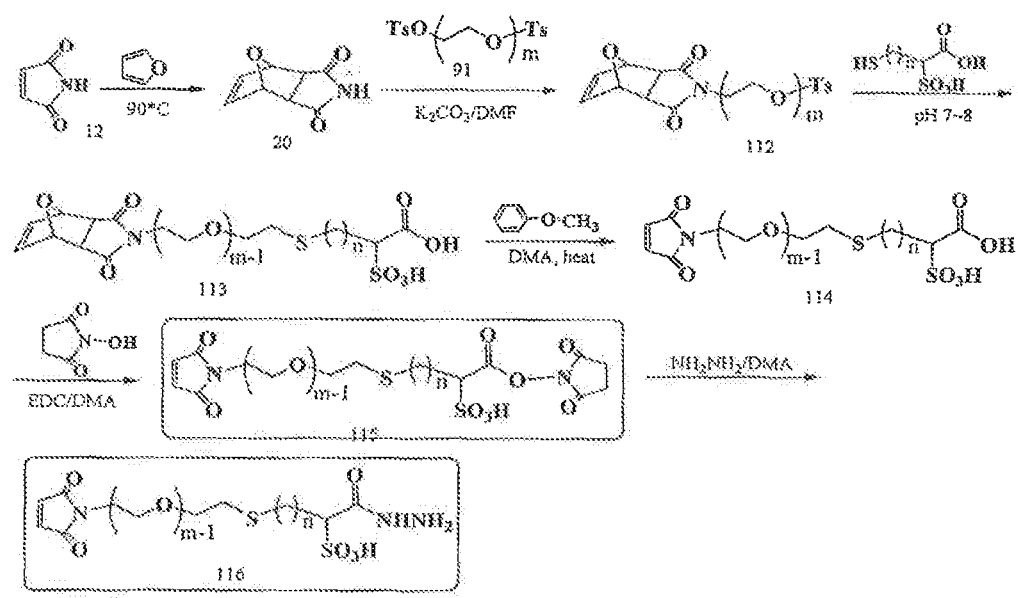
Figure 43:
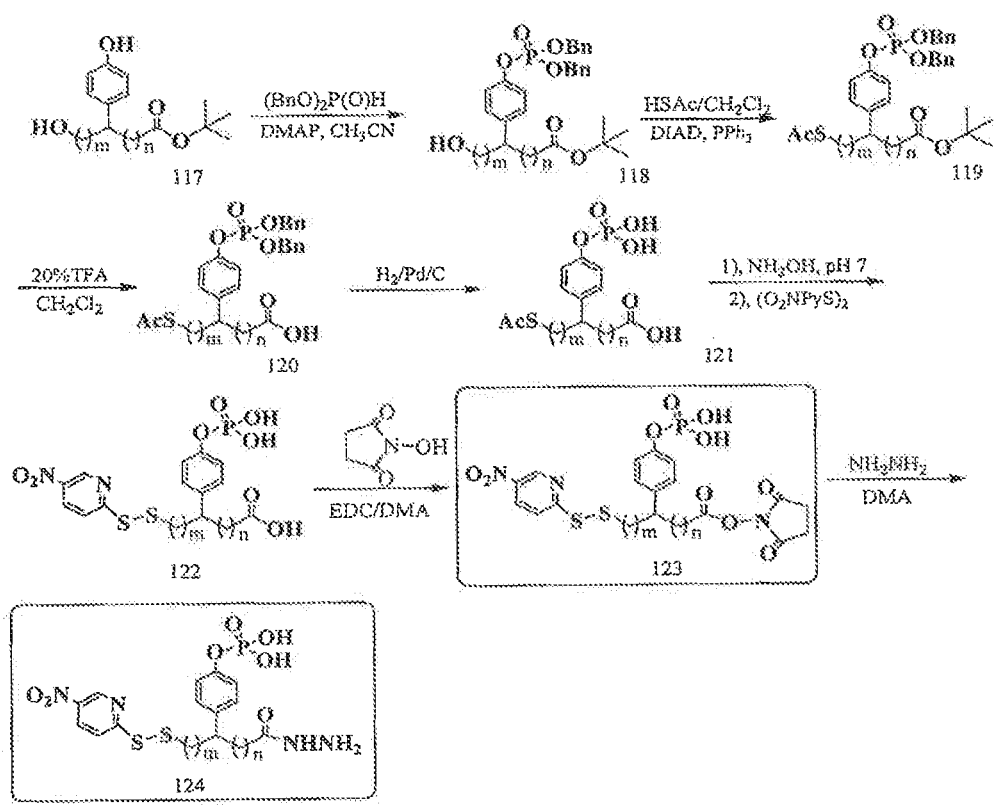
FIGS. 43-44 show the synthesis of phosphate-containing cross-linking reagents, where the phosphate substituent is attached to an aromatic residue or to an alkyl group. These reagents also bear a reactive carboxylic acid ester and a nitropyridyldithio group that allows for linkage via disulfide bonds.
Figure 44:
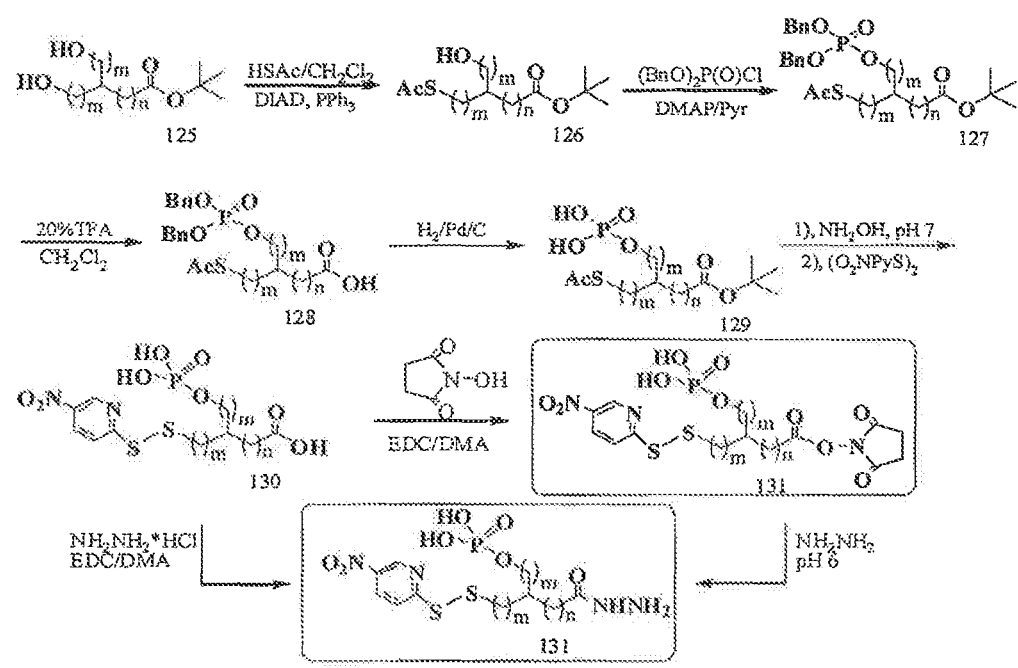
Figure 45:
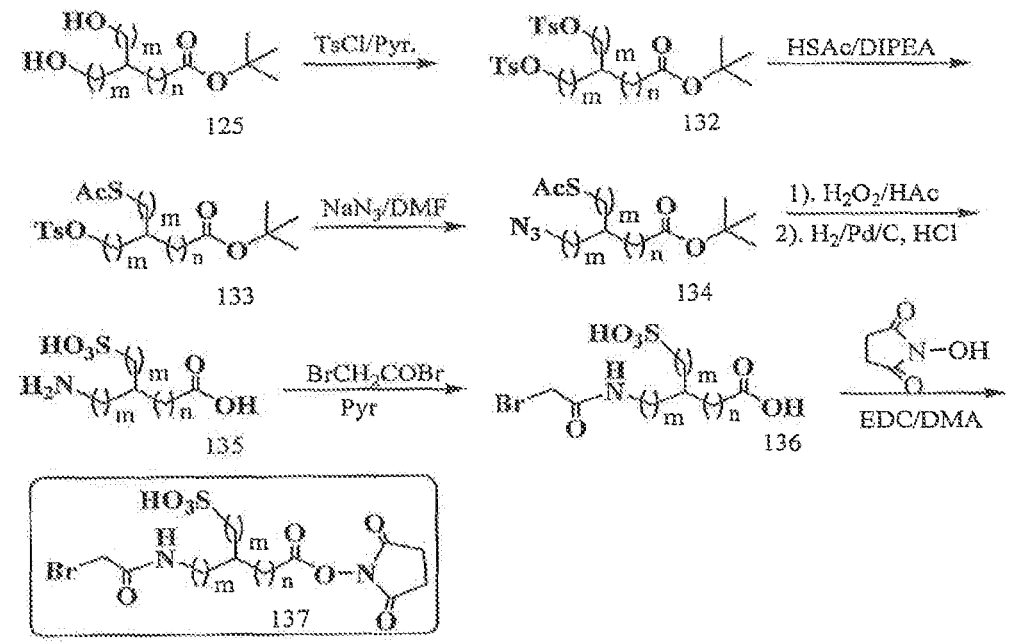
FIGS. 45-49 show the synthesis of charged cross-linking agents bearing reactive carboxylic acid ester and a haloacetyl substituent, enabling linkage via thioether bonds.
Figure 46:
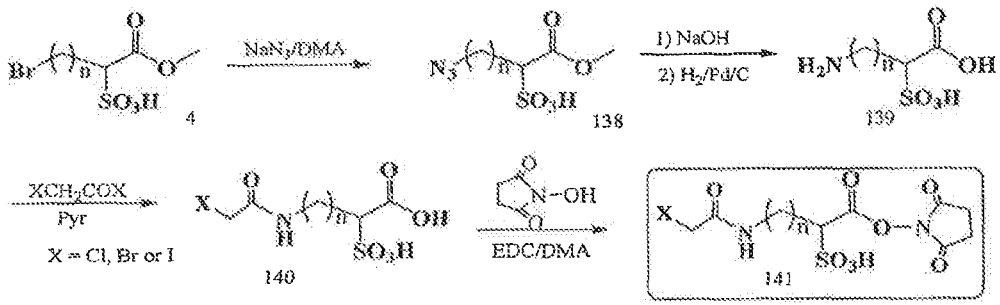
Figure 47:
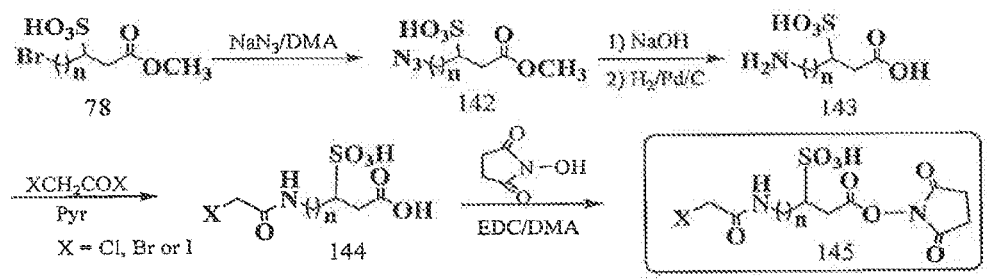
Figure 48:
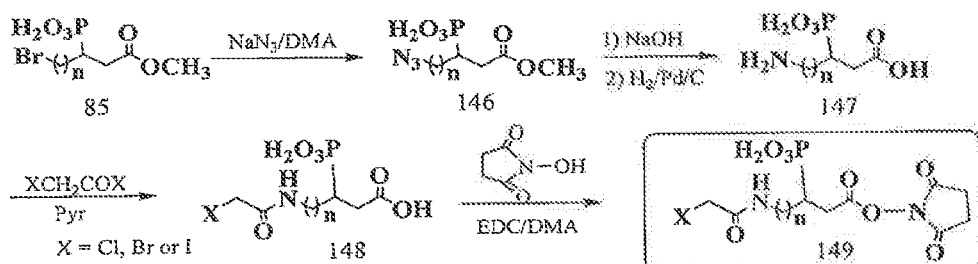
Figure 49:
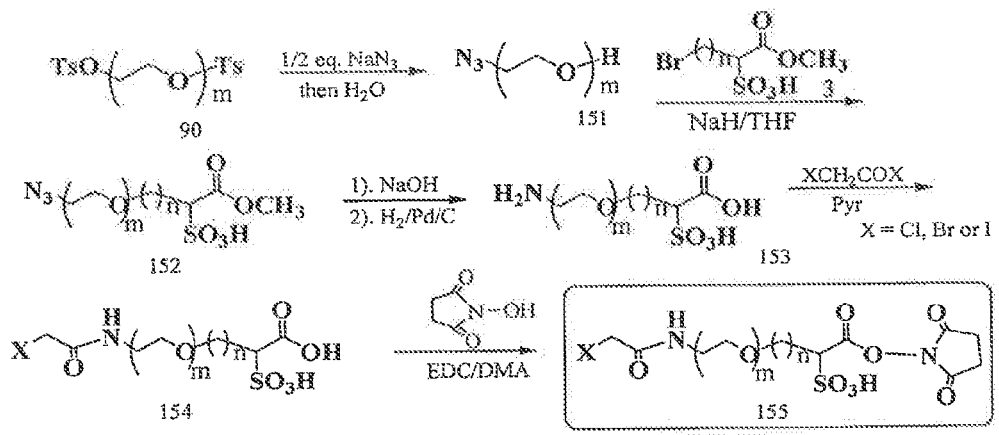
Figure 72A:
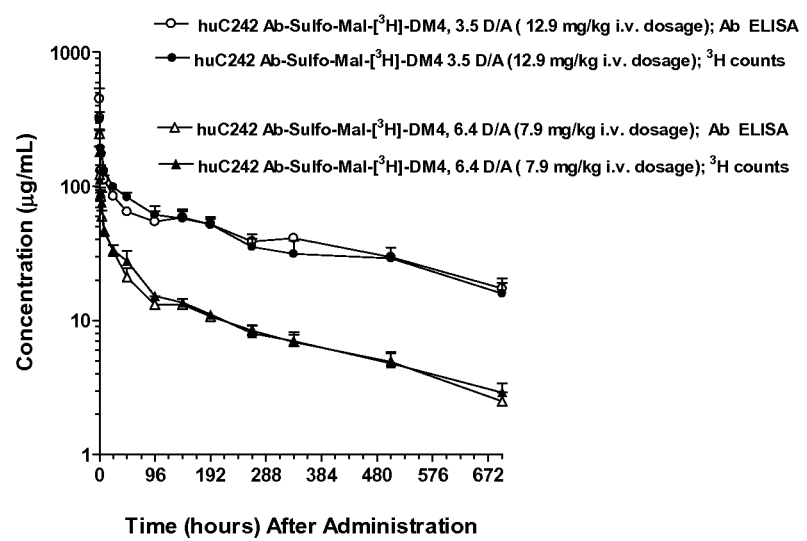
FIGS. 72(A) and (B) show Plasma pharmacokinetics of huC242 Antibody-Sulfo-Mal-[$^3$H-labeled]-DM4 conjugates with 3.5 DM4/Ab or 6.4 DM4/Ab dosed at 12.9 mg/kg and 7.9 mg/kg (i.v.) respectively in CD-1 mice. A. Ab concentrations (measured by ELISA or by 3H counts) versus time after administration. B. Maytansinoid (DM4)/Antibody (Ab) ratio versus time after administration.
Figure 72:
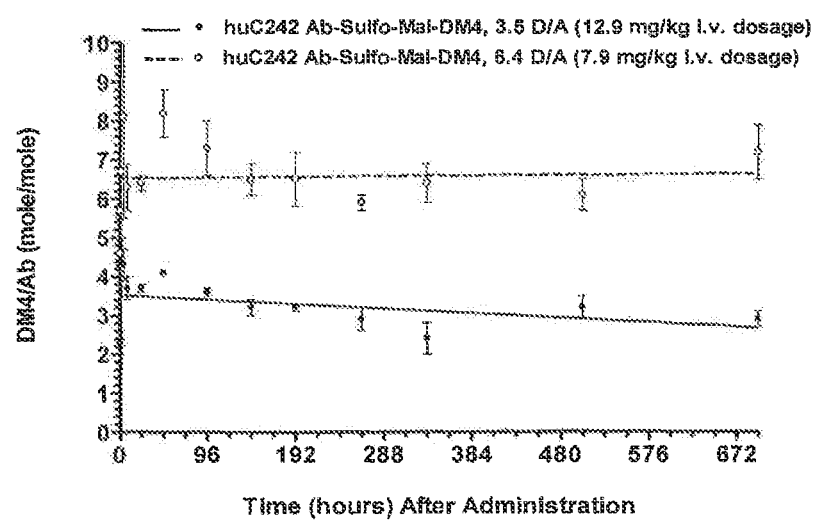

The plasma pharmacokinetics of charged Sulfo-Mal linker conjugates of a humanized antibody C242 with $^3$H-labeled-DM4 (3.5 and 6.4 DM4/Ab) in CD-1 mice were analyzed by antibody ELISA and by $^3$H-counting (FIG. 72). The Ab-Sulfo-Mal-[$^3$H]-DM4 conjugates bearing 3.5 and 6.4 D/A were dosed i.v. at 12.9 and 7.9 mg/kg (antibody dose) respectively. The antibody values of plasma samples were measured by ELISA (based on capture using goat-anti-huIgG antibody and detection using donkey-anti-huIgG antibody-horseradish peroxidase conjugate) and by $^3$H-counting (scintillation counting). FIG. 72 A shows that these two measurements of conjugate concentrations by ELISA and by $^3$H-counting showed similar values for each conjugate. Both the 3.5 and 6.4 D/A Antibody-Sulfo-Mal-DM4 conjugates showed good plasma stability over 4 weeks with half-life of approximately 14.9 days and 9.7 days respectively, which are similar to the half-life of approximately 11.8 days for the unconjugated antibody. The DM4/Ab ratio of the two Ab-Sulfo-Mal-DM4 conjugates (initially 3.5 and 6.4 D/A) were also stable over 4 weeks in plasma circulation, importantly even at the relatively high 6.4 D/A load (FIG. 72 B). The half life of Sulfo-Mal-linked huC242 Ab-Sulfo-Mal-DM4 conjugate with 3.5 D/A load dosed at 12.9 mg/kg was 14.9 days (AUC=38449 hr·μg/mL), compared to a half life of 12.6 days (AUC=25910 hr·μg/mL) for SMCC-linked huC242 Ab-SMCC-DM1 conjugate with a similar 4.2 D/A load dosed at 12 mg/kg, and thus was much improved over that of the SMCC conjugate (FIG. 38 B).

TABLE 1

Comparison of SSNPP and SPP linker in the conjugation of N901 antibody with DM1. Conjugation was conducted for 2 hours at the indicated pH using a 1.7-fold molar excess of DM1 per linker.

| Linker | pH | Linker/Ab | DM1/Ab | % Efficiency | % free drug | SEC Analysis |  |  |  |
|---|---|---|---|---|---|---|---|---|---|
|  |  |  |  |  |  | Monomer | Dimer | Trimer | HMW |
| SSNPP | 7.4 | 4.1 | 3.8 | 93 | 0.8 | 91.9 | 6.3 | 0.6 | 0.1 |
| SPP | 7.4 | 5.6 | 4.3 | 77 | 1.8 | 93.6 | 4.9 | 0.4 | 0.2 |
| SSNPP | 6.5 | 4.0 | 3.7 | 93 | 0.9 | — | — | — | — |
| SPP | 6.5 | 6.6 | 4.6 | 70 | 1.9 | — | — | — | — |

TABLE 2

Reduced linker to antibody ratio required to reach target DM1 to antibody ratio with SSNPP as linker. Conjugation was conducted for 2 hours at pH 7.4 using a 1.1-fold molar excess of DM1 per linker.

| Linker | Linker/Ab | DM1/Ab |
|---|---|---|
| SSNPP | 4.2 | 4.3 |
| SPP | 5.6 | 4.3 |

TABLE 3

Comparison of SSNPP and SPP linker in the conjugation of N901 antibody with DC4. Conjugation was conducted for the indicated time at pH 7.4 using a 1.4-fold molar excess of DC4 per linker.

| Linker | Time, h | Linker/Ab | DC4/Ab | % efficiency |
|---|---|---|---|---|
| SSNPP | 2 | 4.2 | 4.3 | 102 |
| SSNPP | 18 | 4.2 | 4.1 | 98 |
| SPP | 2 | 5.6 | 4.1 | 73 |
| SPP | 18 | 5.6 | 5.1 | 91 |

What is claimed is:

1. A cell-binding agent-drug conjugate of formula (II)

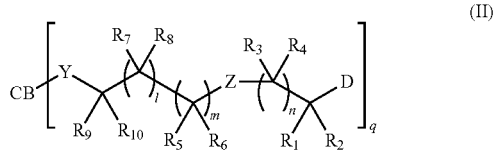

(II)

wherein:
CB represents a cell-binding agent;
D represents a cytotoxic drug linked to the cell-binding agent by a disulfide, thioether, thioester, peptide, hydrazone, ester, ether, carbamate, or amide bond;
$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, a charged substituent selected from anions selected from $SO_3^-$, $X-SO_3^-$, $OPO_3^{2-}$, $X-OPO_3^{2-}$, $PO_3^{2-}$, $X-PO_3^{2-}$, and cations selected from a nitrogen containing heterocycle, $N^+R_{11}R_{12}R_{13}$ and $X-N^+R_{11}R_{12}R_{13}$, or a phenyl; wherein:
$R_{11}$, $R_{12}$, and $R_{13}$ are the same or different and are linear alkyl having from 1 to 6 carbon atoms, branched or cyclic alkyl having from 3 to 6 carbon atoms and X represents phenyl or a linear alkyl from 1 to 6 carbon atoms, or branched or cyclic alkyl having from 3 to 6 carbon atoms;
l, m and n are 0 or an integer from 1 to 4;
Z is an optional polyethyleneoxy unit of formula $(OCH_2CH_2)_p$, wherein p is 0 or an integer from 2 to about 1000;
Y represents a carbonyl, thioether, amide, disulfide, or hydrazone group; and
q represents an integer from 1 to 20;
wherein at least one of $R_1$, $R_2$, $R_3$, $R_4$, $R_5$, $R_6$, $R_7$, $R_8$, $R_9$, and $R_{10}$ is a charged substituent.

2. The conjugate of claim 1, wherein the cytotoxic drug is selected from thiotepa; cyclophosphamide; alkyl sulfonates selected from busulfan, improsulfan and piposulfan; aziridines selected from benzodopa, carboquone, meturedopa, and uredopa; ethylenimines; methylamelamines; acetogenins selected from bullatacin and bullatacinone; camptothecin; bryostatin; callystatin; CC-1065; adozelesin, carzelesin or bizelesin synthetic analogues of CC-1065; cryptophycins; dolastatin; duocarmycin; KW-2189 or CBI-TMI synthetic analogues of duocarmycin; eleutherobin; pancratistatin; sarcodictyin; spongistatin; nitrogen mustards selected from chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas selected from: carmustine, chlorozotocin, fotemustine, lomustine, nimustine, ranimustine; antibiotics selected from: the enediyne antibiotics, calicheamicin, calicheamicin gammal and calicheamicin theta I; dynemicin, including dynemicin A; esperamicin; neocarzinostatin chromophore and related chromoprotein enediyne antiobiotic chromomophores, aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites selected from methotrexate and 5-fluorouracil (5-FU); folic acid analogues selected from denopterin, methotrexate, pteropterin, trimetrexate; purine analogs selected from fludarabine, 6-mercaptopurine, thiamiprine, thioguanine; pyrimnidine analogs selected from ancitabine, azacitidine, 6-azauridine, carmofur, cytarabine, dideoxyuridine, doxifluridine, enocitabine, floxuridine; androgens selected from calusterone, dromostanolone propionate, epitiostanol, mepitiostane, testolactone; anti-adrenals selected from: aminoglutethimide, mitotane, trilostane; folic acid replenisher selected from frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etoglucid; gallium nitrate; hydroxyurea; lentinan; lonidamine; maytansinoids selected from maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2''-trichlorotriethylamine; trichothecenes selected from T-2 toxin, verracurin A, roridin A and anguidine; urethan; vindesine; dacarbazine; mannomustine; mitobronitol; mitolactol; pipobroman; gacytosine; arabinoside ("Ara-C"); cyclophosphamide; thiotepa; taxanes; chlorambucil; gemcitabine; 6-thioguanine; mercaptopurine; methotrexate; platinum analogs selected from cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; anti-hormonal agents selected from anti-estrogens including tamoxifen, raloxifene, aromatase inhibiting 4(5)-imidazoles, 4-hydroxytamoxifen, trioxifene, keoxifene, LY117018, onapristone, and toremifene (Fareston); and antiandrogens selected from flutamide, nilutamide, bicalutamide, leuprolide, and goserelin, siRNA or a combination thereof; and pharmaceutically acceptable salts, acids or derivatives of any of the above.

3. The conjugate of claim 1, wherein the cytotoxic drug is selected from maytansinoids, CC-1065 analogs, morpholino doxorubicin, taxanes, calicheamicins, auristatins, pyrrolobenzodiazepine dimmer, siRNA or a combination thereof, and pharmaceutically acceptable salts, acids or derivatives of any of the above.

4. The conjugate of claim 1, wherein the cell-binding agent binds to target cells selected from tumor cells, virus infected cells, microorganism infected cells, parasite infected cells, autoimmune cells, activated cells, myeloid cells, activated T-cells, B cells, or melanocytes, cells expressing one or more of IGF-IR, CanAg, EGFR, EphA2 receptor, MUC1, MUC16, VEGF, TF, MY9, anti-B4, EpCAM, CD2, CD3, CD4, CD5, CD6, CD11, CD11a, CD18, CD19, CD20, CD22, CD26, CD30, CD33, CD37, CD38, CD40, CD44, CD56, CD79, CD105, CD138, EphA receptors, EphB receptors, EGFr, EGFRvIII, HER2/neu, HER3, mesothelin, cripto, alpha$_v$-beta$_3$, integrin, alpha$_v$beta$_5$ integrin, alpha$_v$beta$_6$ integrin, Apo2, and C242 antigens; and cells expressing insulin growth factor receptor, epidermal growth factor receptor, or folate receptor.

5. The conjugate of claim 1, wherein the cell-binding agent is an antibody, a single chain antibody, an antibody fragment that binds to the target cell, a monoclonal antibody, a single chain monoclonal antibody, or a monoclonal antibody fragment that binds the target cell, a chimeric antibody, a chimeric antibody fragment that binds to the target cell, a domain antibody, a domain antibody fragment that binds to the target cell, adnectins that mimic antibodies, DARPins, a lymphokine, a hormone, a vitamin, a growth factor, a colony stimulating factor, or a nutrient-transport molecule.

6. The conjugate of claim 5, wherein the antibody is a resurfaced antibody, a resurfaced single chain antibody, or a resurfaced antibody fragment thereof.

7. The conjugate of claim 5, wherein the antibody is a monoclonal antibody, a single chain monoclonal antibody, or a monoclonal antibody fragment thereof.

8. The conjugate of claim 5, wherein the antibody is a human antibody, a humanized antibody or a resurfaced antibody, a humanized single chain antibody, or a humanized antibody fragment thereof.

9. The conjugate of claim 5, wherein the antibody is a chimeric antibody, a chimeric antibody fragment, a domain antibody, or a domain antibody fragment thereof.

10. The conjugate of claim 8, wherein the antibody is My9-6, B4, C242, N901, DS6, EpCAM, EphA2 receptor, CD38, IGF-IR, CNTO 95, B-B4, trastuzumab, pertuzumab, bivatuzumab, sibrotuzumab, pertuzumab, or rituximab.

11. The conjugate of claim 4, wherein the tumor cells are selected from breast cancer cells, prostate cancer cells, ovarian cancer cells, colorectal cancer cells, gastric cancer cells, squamous cancer cells, small-cell lung cancer cells, and testicular cancer cells.

12. A method of treating a tumor comprising administering to a subject in need of treatment a therapeutically effective amount of a conjugate of claim 1.

13. A compound of formula (III):

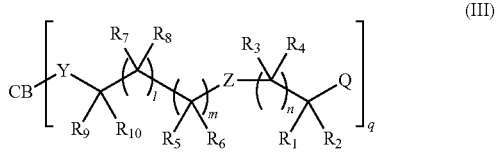

wherein:
CB represents a cell-binding agent;
Q represents a functional group that enables linkage of a cytotoxic drug via a disulfide, thioether, thioester, peptide, hydrazone, ester, ether, carbamate or amide bond;
$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, a charged substituent selected from anions selected from $SO_3^-$, $X-SO_3^-$, $OPO_3^{2-}$, $X-OPO_3^{2-}$, $PO_3^{2-}$, $X-PO_3^{2-}$, and cations selected from a nitrogen containing heterocycle, $N^+R_{11}R_{12}R_{13}$ and $X-N^+R_{11}R_{12}R_{13}$, or a phenyl, wherein:
$R_{11}$, $R_{12}$, and $R_{13}$ are the same or different and are linear alkyl having from 1 to 6 carbon atoms, or branched or cyclic alkyl having from 3 to 6 carbon atoms and X represents phenyl or a linear alkyl having from 1 to 6 carbon atoms, or branched or cyclic alkyl having from 3 to 6 carbon atoms;
l, m and n are 0 or an integer from 1 to 4;
Z is an optional polyethyleneoxy unit of formula $(OCH_2CH_2)_p$, wherein p is 0 or an integer from 2 to about 1000; and Y represents a carbonyl, thioether, amide, disulfide, or hydrazone group; and q represents an integer from 1 to 20;

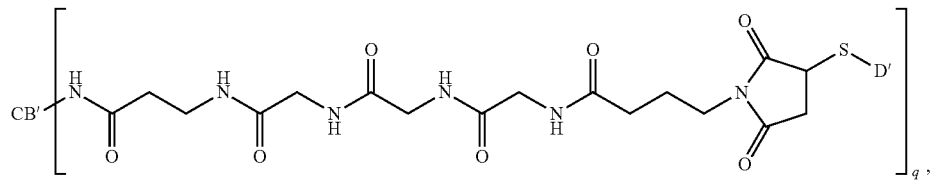

wherein at least one of $R_1$, $R_2$, $R_3$, $R_4$, $R_5$, $R_6$, $R_7$, $R_8$, $R_9$, and $R_{10}$ is a charged substituent.

14. A compound of formula (IV):

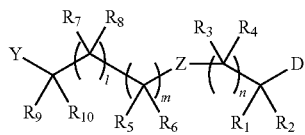

wherein:
Y' represents a functional group that enables reaction with a cell-binding agent;
D represents a cytotoxic drug linked to the cell-binding agent by a disulfide, thioether, thioester, peptide, hydrazone, ester, ether, carbamate, or amide bond;
$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, a charged substituent selected from anions selected from $SO_3^-$, $X$—$SO_3^-$, $OPO_3^{2-}$, $X$—$OPO_3^{2-}$, $PO_3^{2-}$, $X$—$PO_3^{2-}$, and cations selected from a nitrogen containing heterocycle, $N^+R_{11}R_{12}R_{13}$ and $X$—$N^+R_{11}R_{12}R_{13}$, or a phenyl, wherein:
$R_{11}$, $R_{12}$, and $R_{13}$ are the same or different and are linear alkyl having from 1 to 6 carbon atoms, or branched or cyclic alkyl having from 3 to 6 carbon atoms and X represents phenyl or a linear alkyl having from 1 to 6 carbon atoms, or branched or cyclic alkyl having from 3 to 6 carbon atoms;
l, m and n are 0 or an integer from 1 to 4;
Z is an optional polyethyleneoxy unit of formula $(OCH_2CH_2)_p$, wherein p is 0 or an integer from 2 to about 1000,
wherein at least one of $R_1$, $R_2$, $R_3$, $R_4$, $R_5$, $R_6$, $R_7$, $R_8$, $R_9$, and $R_{10}$ is a charged substituent.

15. A pharmaceutical composition comprising an effective amount of the conjugate of claim 1, a pharmaceutically acceptable salt or solvate thereof, and a pharmaceutically acceptable carrier, diluent or excipient.

16. The conjugate of claim 1, wherein one of $R_1$, $R_2$, $R_3$, $R_4$, $R_9$, and $R_{10}$ is a charged substituent selected from $SO_3^-$, $X$—$SO_3^-$, $OPO_3^{2-}$, $X$—$OPO_3^{2-}$, $N^+R_{11}R_{12}R_{13}$ and $X$—$N^+R_{11}R_{12}R_{13}$, and the rest are H; l, g and m are each 0; and n is 1.

17. The conjugate of claim 16, wherein one of $R_1$, $R_2$, $R_3$, $R_4$, $R_9$, and $R_{10}$ is $SO_3^-$ or $X$—$SO_3^-$, the rest are H; l, g and m are each 0; and n is 1.

18. The conjugate of claim 16, wherein Z is absent.

19. A cell-binding agent-drug conjugate represented by the following formula:

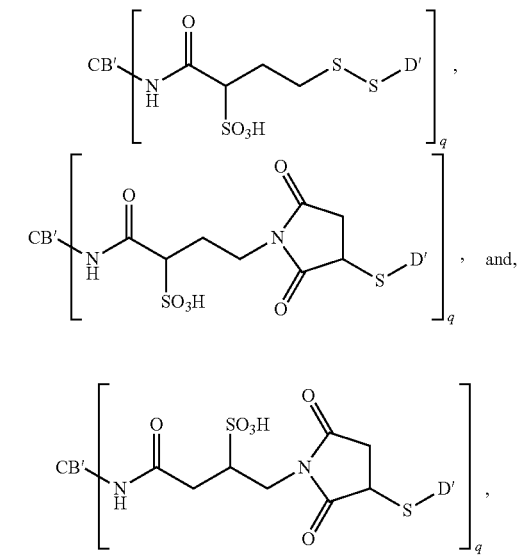

wherein D' is a cytotoxic drug, q represents an integer from 1 to 20, and CB'— represents a cell-binding agent.

20. The conjugate of claim 1, which is represented by one of the following formulae:

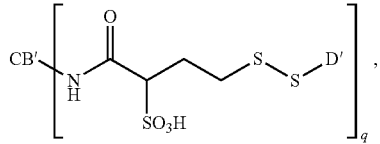

wherein D' is the cytotoxic drug, and CB'—NH— represents the cell-binding agent linked to Y.

21. The conjugate of claim 20, which is represented by the following formula:

22. The conjugate of claim 20, wherein the cytotoxic drug is a maytansinoid.

23. The conjugate of claim 20, wherein the cytotoxic drug is DM1 or DM4.

24. The conjugate of claim 21, wherein the cytotoxic drug is DM4.

25. The conjugate of claim 24, wherein the cell-binding agent is an antibody that binds to a folate receptor.

26. The conjugate of claim 25, wherein the folate receptor is FOLR1 (folate receptor 1).

* * * * *

UNITED STATES PATENT AND TRADEMARK OFFICE
CERTIFICATE OF CORRECTION

PATENT NO. : 8,613,930 B2  
APPLICATION NO. : 13/542126  
DATED : December 24, 2013  
INVENTOR(S) : Ravi V. J. Chari et al.

Page 1 of 1

It is certified that error appears in the above-identified patent and that said Letters Patent is hereby corrected as shown below:

In the Claims

Claim 14, Column 69, line 20, replace the structure

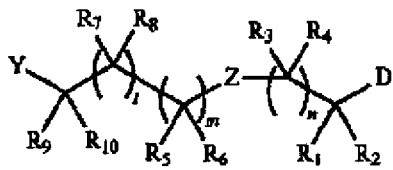

with the structure

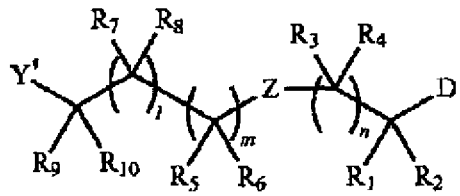

Signed and Sealed this  
Twenty-third Day of December, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,613,930 B2
APPLICATION NO. : 13/542126
DATED : December 24, 2013
INVENTOR(S) : Ravi V. J. Chari et al.

It is certified that error appears in the above-identified patent and that said Letters Patent is hereby corrected as shown below:

In the Claims

In Column 69, Line 63 in Claim 16, Replace "l, g and m are each 0" with "l and m are each 0"

In Column 69, Lines 66-67 in Claim 17, Replace "l, g and m are each 0" with "l and m are each 0"

Signed and Sealed this
Thirty-first Day of January, 2023

Katherine Kelly Vidal
*Director of the United States Patent and Trademark Office*